US007676263B2

(12) United States Patent
Harris et al.

(10) Patent No.: US 7,676,263 B2
(45) Date of Patent: Mar. 9, 2010

(54) MINIMALLY INVASIVE SYSTEM FOR SELECTING PATIENT-SPECIFIC THERAPY PARAMETERS

(75) Inventors: John F. Harris, Bellevue, WA (US); Kent W. Leyde, Sammamish, WA (US); Jaideep Mavoori, Bellevue, WA (US)

(73) Assignee: NeuroVista Corporation, Seattle, WA (US)

( * ) Notice: Subject to any disclaimer, the term of this patent is extended or adjusted under 35 U.S.C. 154(b) by 0 days.

(21) Appl. No.: 11/766,760

(22) Filed: Jun. 21, 2007

(65) Prior Publication Data
US 2008/0033502 A1 Feb. 7, 2008

Related U.S. Application Data

(60) Provisional application No. 60/805,710, filed on Jun. 23, 2006.

(51) Int. Cl.
*A61B 5/00* (2006.01)
(52) U.S. Cl. ...................................... 600/544
(58) Field of Classification Search ................ 600/544, 600/378; 607/2, 45
See application file for complete search history.

(56) References Cited

U.S. PATENT DOCUMENTS

| | | | |
|---|---|---|---|
| 3,218,638 A | 11/1965 | Honig | |
| 3,498,287 A | 3/1970 | Ertl | |
| 3,522,811 A | 8/1970 | Schwartz | |
| 3,575,162 A | 4/1971 | Gaarder | |
| 3,837,331 A | 9/1974 | Ross | |
| 3,850,161 A | 11/1974 | Liss | |
| 3,863,625 A | 2/1975 | Viglione et al. | |
| 3,882,850 A | 5/1975 | Bailin et al. | |
| 3,918,461 A | 11/1975 | Cooper | |
| 3,967,616 A | 7/1976 | Ross | |
| 3,993,046 A | 11/1976 | Fernandez | |
| 4,201,224 A | 5/1980 | John | |
| 4,214,591 A | 7/1980 | Sato et al. | |
| 4,279,258 A | 7/1981 | John | |
| 4,305,402 A | 12/1981 | Katims | |
| 4,334,545 A | 6/1982 | Shiga | |
| 4,407,299 A | 10/1983 | Culver | |

(Continued)

FOREIGN PATENT DOCUMENTS

CA 2251852 4/1999

(Continued)

OTHER PUBLICATIONS

Schelter et al.; Testing statistical significance of multivariate time series analysis techniques for epileptic seizure prediction; Chaos vol. 16, 2006, pp. 013108-1-013108-10.*

(Continued)

*Primary Examiner*—Robert L Nasser
(74) *Attorney, Agent, or Firm*—Shay Glenn LLP

(57) ABSTRACT

The present invention provides systems and methods for ambulatory, long term monitoring of a physiological signal from a patient. At least a portion of the systems of the present invention may be implanted within the patient in a minimally invasive manner. In preferred embodiments, brain activity signals are sampled from the patient and are transmitted to a handheld patient communication device for further processing.

33 Claims, 17 Drawing Sheets

U.S. PATENT DOCUMENTS

| | | | |
|---|---|---|---|
| 4,408,616 A | 10/1983 | Duffy et al. | |
| 4,421,122 A | 12/1983 | Duffy | |
| 4,471,786 A | 9/1984 | Inagaki | |
| 4,494,950 A | 1/1985 | Fischell | |
| 4,505,275 A | 3/1985 | Chen | |
| 4,545,388 A | 10/1985 | John | |
| 4,566,464 A | 1/1986 | Piccone et al. | |
| 4,573,481 A | 3/1986 | Bullara | |
| 4,579,125 A | 4/1986 | Strobl et al. | |
| 4,590,946 A | 5/1986 | Loeb | |
| 4,612,934 A | 9/1986 | Borkan | |
| 4,679,144 A | 7/1987 | Cox et al. | |
| 4,702,254 A | 10/1987 | Zabara | |
| 4,768,176 A | 8/1988 | Kehr et al. | |
| 4,768,177 A | 8/1988 | Kehr et al. | |
| 4,785,827 A | 11/1988 | Fischer | |
| 4,793,353 A | 12/1988 | Borkam | |
| 4,817,628 A | 4/1989 | Zealear | |
| 4,838,272 A | 6/1989 | Lieber | |
| 4,844,075 A | 7/1989 | Liss et al. | |
| 4,852,573 A | 8/1989 | Kennedy | |
| 4,867,164 A | 9/1989 | Zabara | |
| 4,873,981 A | 10/1989 | Abrams et al. | |
| 4,878,498 A | 11/1989 | Abrams et al. | |
| 4,920,979 A | 5/1990 | Bullara | |
| 4,926,865 A | 5/1990 | Oman | |
| 4,955,380 A | 9/1990 | Edell | |
| 4,978,680 A | 12/1990 | Sofia | |
| 4,979,511 A | 12/1990 | Terry | |
| 4,991,582 A | 2/1991 | Byers et al. | |
| 5,010,891 A | 4/1991 | Chamoun | |
| 5,016,635 A | 5/1991 | Graupe | |
| 5,025,807 A | 6/1991 | Zabara | |
| 5,031,618 A | 7/1991 | Mullett | |
| 5,070,873 A | 12/1991 | Graupe et al. | |
| 5,082,861 A | 1/1992 | Sofia | |
| 5,097,835 A | 3/1992 | Putz | |
| RE34,015 E | 8/1992 | Duffy | |
| 5,154,172 A | 10/1992 | Terry | |
| 5,167,229 A | 12/1992 | Peckham et al. | |
| 5,179,950 A | 1/1993 | Stanislaw | |
| 5,181,520 A | 1/1993 | Wertheim et al. | |
| 5,186,170 A | 2/1993 | Varichio | |
| 5,188,104 A | 2/1993 | Wernicke | |
| 5,190,029 A | 3/1993 | Byron et al. | |
| 5,193,539 A | 3/1993 | Schulman et al. | |
| 5,193,540 A | 3/1993 | Schulman et al. | |
| 5,205,285 A | 4/1993 | Baker, Jr. | |
| 5,215,086 A | 6/1993 | Terry, Jr. et al. | |
| 5,215,088 A | 6/1993 | Normann | |
| 5,215,089 A | 6/1993 | Baker, Jr. | |
| 5,222,494 A | 6/1993 | Baker, Jr. | |
| 5,222,503 A | 6/1993 | Ives | |
| 5,231,988 A | 8/1993 | Wernicke et al. | |
| 5,235,980 A | 8/1993 | Varichio et al. | |
| 5,237,991 A | 8/1993 | Baker, Jr. | |
| 5,251,634 A | 10/1993 | Weinberg | |
| 5,263,480 A | 11/1993 | Wernicke et al. | |
| 5,265,619 A | 11/1993 | Comby et al. | |
| 5,269,302 A | 12/1993 | Swartz et al. | |
| 5,269,303 A | 12/1993 | Wernicke et al. | |
| 5,269,315 A | 12/1993 | Leuchter et al. | |
| 5,292,772 A | 3/1994 | Sofia | |
| 5,293,879 A | 3/1994 | Vonk | |
| 5,299,569 A | 4/1994 | Wernicke et al. | |
| 5,300,094 A | 4/1994 | Kallok et al. | |
| 5,304,206 A | 4/1994 | Baker, Jr. et al. | |
| 5,311,876 A | 5/1994 | Olsen et al. | |
| 5,312,439 A | 5/1994 | Loeb | |
| 5,314,458 A | 5/1994 | Najafi et al. | |
| 5,324,316 A | 6/1994 | Schulman et al. | |
| 5,330,515 A | 7/1994 | Rutecki et al. | |
| 5,335,657 A | 8/1994 | Terry et al. | |
| 5,342,408 A | 8/1994 | deCoriolis et al. | |
| 5,342,409 A | 8/1994 | Mullett | |
| 5,343,064 A | 8/1994 | Spangler et al. | |
| 5,349,962 A | 9/1994 | Lockard et al. | |
| 5,351,394 A | 10/1994 | Weinberg | |
| 5,361,760 A | 11/1994 | Normann | |
| 5,365,939 A | 11/1994 | Ochs | |
| 5,376,359 A | 12/1994 | Johnson | |
| 5,392,788 A | 2/1995 | Hudspeth | |
| 5,405,365 A | 4/1995 | Hoegnelid et al. | |
| 5,405,367 A | 4/1995 | Schulman et al. | |
| 5,411,540 A | 5/1995 | Edell et al. | |
| 5,458,117 A | 10/1995 | Chamoun | |
| 5,474,547 A | 12/1995 | Aebischer et al. | |
| 5,476,494 A | 12/1995 | Edell et al. | |
| 5,486,999 A | 1/1996 | Mebane | |
| 5,513,649 A | 5/1996 | Gevins | |
| 5,531,778 A | 7/1996 | Maschino et al. | |
| 5,540,730 A | 7/1996 | Terry | |
| 5,540,734 A | 7/1996 | Zabara | |
| 5,549,656 A | 8/1996 | Reiss | |
| 5,555,191 A | 9/1996 | Hripcsak | |
| 5,571,148 A | 11/1996 | Loeb et al. | |
| 5,571,150 A | 11/1996 | Wernicke | |
| 5,575,813 A | 11/1996 | Edell et al. | |
| 5,611,350 A * | 3/1997 | John | 600/378 |
| 5,626,145 A | 5/1997 | Clapp et al. | |
| 5,626,627 A * | 5/1997 | Krystal et al. | 607/45 |
| 5,638,826 A | 6/1997 | Wolpaw | |
| 5,649,068 A | 7/1997 | Boser et al. | |
| 5,683,422 A | 11/1997 | Rise | |
| 5,690,681 A | 11/1997 | Geddes et al. | |
| 5,697,369 A | 12/1997 | Long | |
| 5,700,282 A | 12/1997 | Zabara | |
| 5,707,400 A | 1/1998 | Terry et al. | |
| 5,711,316 A | 1/1998 | Elsberry et al. | |
| 5,713,923 A | 2/1998 | Ward et al. | |
| 5,715,821 A | 2/1998 | Faupel | |
| 5,716,377 A | 2/1998 | Rise et al. | |
| 5,720,294 A | 2/1998 | Skinner | |
| 5,735,814 A | 4/1998 | Elsberry et al. | |
| 5,743,860 A | 4/1998 | Hively et al. | |
| 5,752,979 A | 5/1998 | Benabid | |
| 5,769,778 A | 6/1998 | Abrams et al. | |
| 5,776,434 A | 7/1998 | Purewal et al. | |
| 5,782,798 A | 7/1998 | Rise | |
| 5,782,874 A | 7/1998 | Loos | |
| 5,792,186 A | 8/1998 | Rise | |
| 5,800,474 A | 9/1998 | Bernabid et al. | |
| 5,813,993 A | 9/1998 | Kaplan | |
| 5,814,014 A | 9/1998 | Elsberry et al. | |
| 5,815,413 A | 9/1998 | Hively et al. | |
| 5,816,247 A | 10/1998 | Maynard | |
| 5,824,021 A | 10/1998 | Rise | |
| 5,832,932 A | 11/1998 | Elsberry et al. | |
| 5,833,709 A | 11/1998 | Rise et al. | |
| 5,857,978 A | 1/1999 | Hively et al. | |
| 5,876,424 A | 3/1999 | O'Phelan et al. | |
| 5,899,922 A | 5/1999 | Loos | |
| 5,913,881 A | 6/1999 | Benz et al. | |
| 5,916,239 A | 6/1999 | Geddes et al. | |
| 5,917,429 A | 6/1999 | Otis, Jr. et al. | |
| 5,928,272 A | 7/1999 | Adkins | |
| 5,931,791 A | 8/1999 | Saltzstein et al. | |
| 5,938,689 A | 8/1999 | Fischell et al. | |
| 5,941,906 A | 8/1999 | Barreras et al. | |
| 5,950,632 A | 9/1999 | Reber et al. | |
| 5,957,861 A | 9/1999 | Combs et al. | |
| 5,971,594 A | 10/1999 | Sahai et al. | |
| 5,975,085 A | 11/1999 | Rise | |
| 5,978,702 A | 11/1999 | Ward et al. | |

| | | | | | | |
|---|---|---|---|---|---|---|
| 5,978,710 | A | 11/1999 | Prutchi et al. | 6,571,125 B2 | 5/2003 | Thompson |
| 5,995,868 | A | 11/1999 | Dorfmeister et al. | 6,572,528 B2 | 6/2003 | Rohan et al. |
| 6,006,124 | A | 12/1999 | Fischell et al. | 6,587,719 B1 | 7/2003 | Barrett et al. |
| 6,016,449 | A | 1/2000 | Fischell et al. | 6,591,132 B2 | 7/2003 | Gotman et al. |
| 6,018,682 | A | 1/2000 | Rise | 6,591,137 B1 | 7/2003 | Fischell et al. |
| 6,042,548 | A | 3/2000 | Giuffre | 6,591,138 B1 | 7/2003 | Fischell et al. |
| 6,042,579 | A | 3/2000 | Elsberry et al. | 6,597,954 B1 | 7/2003 | Pless et al. |
| 6,051,017 | A | 4/2000 | Loeb et al. | 6,600,956 B2 | 7/2003 | Maschino |
| 6,052,619 | A | 4/2000 | John | 6,609,025 B2 | 8/2003 | Barrett et al. |
| 6,061,593 | A | 5/2000 | Fischell et al. | 6,618,623 B1 | 9/2003 | Pless et al. |
| 6,066,163 | A | 5/2000 | John | 6,620,415 B2 | 9/2003 | Donovan |
| 6,081,744 | A | 6/2000 | Loos | 6,622,036 B1 | 9/2003 | Suffin |
| 6,094,598 | A | 7/2000 | Elsberry et al. | 6,622,038 B2 | 9/2003 | Barrett et al. |
| 6,109,269 | A | 8/2000 | Rise et al. | 6,622,041 B2 | 9/2003 | Terry et al. |
| 6,117,066 | A | 9/2000 | Abrams et al. | 6,622,047 B2 | 9/2003 | Barrett et al. |
| 6,128,537 | A | 10/2000 | Rise et al. | 6,658,287 B1 | 12/2003 | Litt et al. |
| 6,128,538 | A | 10/2000 | Fischell et al. | 6,665,562 B2 | 12/2003 | Gluckman et al. |
| 6,134,474 | A | 10/2000 | Fischell et al. | 6,668,191 B1 | 12/2003 | Boveja |
| 6,161,045 | A | 12/2000 | Fischell et al. | 6,671,555 B2 | 12/2003 | Gielen |
| 6,167,304 | A | 12/2000 | Loos | 6,678,548 B1 | 1/2004 | Echauz et al. |
| 6,171,239 | B1 | 1/2001 | Humphrey | 6,684,105 B2 | 1/2004 | Cohen et al. |
| 6,176,242 | B1 | 1/2001 | Rise | 6,687,538 B1 | 2/2004 | Hrdlicka et al. |
| 6,205,359 | B1 | 3/2001 | Boveja | 6,735,467 B2 | 5/2004 | Wilson |
| 6,221,011 | B1 | 4/2001 | Bardy | 6,760,626 B1 | 7/2004 | Boveja |
| 6,227,203 | B1 | 5/2001 | Rise et al. | 6,768,969 B1 | 7/2004 | Nikitin et al. |
| 6,230,049 | B1 | 5/2001 | Fischell et al. | 6,778,854 B2 | 8/2004 | Puskas |
| 6,248,126 | B1 | 6/2001 | Lesser et al. | 6,782,292 B2 | 8/2004 | Whitehurst |
| 6,249,703 | B1 | 6/2001 | Stanton | 6,879,859 B1 | 4/2005 | Boveja |
| 6,263,237 | B1 | 7/2001 | Rise | 6,893,395 B1 | 5/2005 | Kraus et al. |
| 6,280,198 | B1 * | 8/2001 | Calhoun et al. ............ 434/236 | 6,912,419 B2 | 6/2005 | Hill |
| 6,304,775 | B1 | 10/2001 | Iasemidis et al. | 6,921,538 B2 | 7/2005 | Donovan |
| 6,309,406 | B1 | 10/2001 | Jones et al. | 6,921,541 B2 | 7/2005 | Chasin et al. |
| 6,328,699 | B1 | 12/2001 | Eigler | 6,901,292 B2 | 8/2005 | Whitehurst |
| 6,337,997 | B1 | 1/2002 | Rise | 6,923,784 B2 | 8/2005 | Stein |
| 6,339,725 | B1 | 1/2002 | Naritoku | 6,931,274 B2 | 8/2005 | Williams |
| 6,341,236 | B1 | 1/2002 | Osorio et al. | 6,934,580 B1 | 8/2005 | Osorio |
| 6,343,226 | B1 | 1/2002 | Sunde et al. | 6,937,891 B2 | 8/2005 | Leinders et al. |
| 6,353,754 | B1 | 3/2002 | Fischell et al. | 6,944,501 B1 | 9/2005 | Pless |
| 6,354,299 | B1 | 3/2002 | Fischell et al. | 6,950,706 B2 | 9/2005 | Rodriquez |
| 6,356,784 | B1 | 3/2002 | Lozano et al. | 6,973,342 B1 | 12/2005 | Swanson |
| 6,356,788 | B2 | 3/2002 | Boveja | 7,010,351 B2 * | 3/2006 | Firlik et al. .................. 607/45 |
| 6,358,203 | B2 | 3/2002 | Bardy | 7,174,212 B1 | 2/2007 | Klehn et al. |
| 6,358,281 | B1 | 3/2002 | Berrang et al. | 7,177,701 B1 * | 2/2007 | Pianca ........................ 607/116 |
| 6,360,122 | B1 | 3/2002 | Fischell | 7,231,254 B2 | 6/2007 | DiLorenzo |
| 6,366,813 | B1 | 4/2002 | DiLorenzo | 7,463,917 B2 * | 12/2008 | Martinez .................... 600/395 |
| 6,366,814 | B1 | 4/2002 | Boveja | 2001/0051819 A1 | 12/2001 | Fischell et al. |
| 6,374,140 | B1 | 4/2002 | Rise | 2001/0056290 A1 | 12/2001 | Fischell et al. |
| 6,386,882 | B1 | 5/2002 | Linberg | 2002/0002390 A1 | 1/2002 | Fischell et al. |
| 6,402,678 | B1 | 6/2002 | Fischell et al. | 2002/0035338 A1 | 3/2002 | Dear et al. |
| 6,411,854 | B1 | 6/2002 | Tziviskos et al. | 2002/0054694 A1 | 5/2002 | Vachtsevanos et al. |
| 6,427,086 | B1 | 7/2002 | Fischell et al. | 2002/0072770 A1 | 6/2002 | Pless |
| 6,434,419 | B1 | 8/2002 | Gevins et al. | 2002/0072776 A1 | 6/2002 | Osorio et al. |
| 6,442,421 | B1 | 8/2002 | Le Van Quyen et al. | 2002/0072782 A1 | 6/2002 | Osorio et al. |
| 6,443,891 | B1 | 9/2002 | Grevious | 2002/0077670 A1 | 6/2002 | Archer et al. |
| 6,453,198 | B1 | 9/2002 | Torgerson | 2002/0095099 A1 | 7/2002 | Quyen et al. |
| 6,463,328 | B1 | 10/2002 | John | 2002/0099412 A1 | 7/2002 | Fischell et al. |
| 6,466,822 | B1 | 10/2002 | Pless | 2002/0103512 A1 | 8/2002 | Echauz et al. |
| 6,471,645 | B1 | 10/2002 | Warkentin et al. | 2002/0111542 A1 | 8/2002 | Warkentin et al. |
| 6,473,639 | B1 | 10/2002 | Fischell et al. | 2002/0116042 A1 | 8/2002 | Boling |
| 6,473,644 | B1 | 10/2002 | Terry et al. | 2002/0126036 A1 | 9/2002 | Flaherty et al. |
| 6,480,743 | B1 | 11/2002 | Kirkpatrick | 2002/0169485 A1 | 11/2002 | Pless et al. |
| 6,484,132 | B1 | 11/2002 | Hively et al. | 2002/0177882 A1 | 11/2002 | DiLorenzo |
| 6,488,617 | B1 | 12/2002 | Katz | 2002/0188330 A1 | 12/2002 | Gielen et al. |
| 6,496,724 | B1 | 12/2002 | Levendowski et al. | 2003/0004428 A1 | 1/2003 | Pless |
| 6,510,340 | B1 | 1/2003 | Jordan | 2003/0009207 A1 | 1/2003 | Paspa et al. |
| 6,511,424 | B1 | 1/2003 | Moore-Ede | 2003/0013981 A1 * | 1/2003 | Gevins et al. ................ 600/544 |
| 6,529,774 | B1 | 3/2003 | Greene | 2003/0018367 A1 | 1/2003 | DiLorenzo |
| 6,534,693 | B2 | 3/2003 | Fischell et al. | 2003/0028072 A1 | 2/2003 | Fischell et al. |
| 6,547,746 | B1 | 4/2003 | Marino | 2003/0050549 A1 | 3/2003 | Sochor |
| 6,549,804 | B1 | 4/2003 | Osorio et al. | 2003/0073917 A1 | 4/2003 | Echauz et al. |
| 6,553,262 | B1 | 4/2003 | Lang et al. | 2003/0074033 A1 | 4/2003 | Pless et al. |
| 6,560,486 | B1 | 5/2003 | Osorio et al. | 2003/0083716 A1 | 5/2003 | Nicolelis et al. |
| 6,571,123 | B2 | 5/2003 | Ives et al. | 2003/0114886 A1 | 6/2003 | Gluckman et al. |

| | | |
|---|---|---|
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fishcell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1* | 9/2004 | Whitehurst et al. ............ 607/45 |
| 2004/0176359 A1 | 9/2004 | Wermeling |
| 2004/0199212 A1 | 10/2004 | Fischell |
| 2004/0210269 A1* | 10/2004 | Shalev et al. .................. 607/45 |
| 2004/0267152 A1 | 12/2004 | Pineda et al. |
| 2005/0004621 A1 | 1/2005 | Boveja et al. |
| 2005/0010261 A1 | 1/2005 | Luders et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1* | 2/2005 | Devlin et al. .................. 607/45 |
| 2005/0049649 A1 | 3/2005 | Luders et al. |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0187789 A1 | 8/2005 | Hatlestad |
| 2005/0197590 A1 | 9/2005 | Osorio et al. |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0224191 A1 | 10/2006 | Dilorenzo |
| 2006/0253096 A1 | 11/2006 | Blakley et al. |
| 2006/0293720 A1 | 12/2006 | DiLorenzo et al. |
| 2007/0073355 A1 | 3/2007 | DiLorenzo |
| 2007/0142862 A1 | 6/2007 | DiLorenzo |
| 2007/0149952 A1 | 6/2007 | Bland et al. |
| 2007/0150024 A1 | 6/2007 | Leyde et al. |
| 2007/0150025 A1 | 6/2007 | DiLorenzo et al. |
| 2007/0161919 A1* | 7/2007 | DiLorenzo .................. 600/544 |
| 2007/0162086 A1 | 7/2007 | DiLorenzo |
| 2007/0167991 A1 | 7/2007 | DiLorenzo |
| 2007/0244407 A1* | 10/2007 | Osorio ....................... 600/544 |

FOREIGN PATENT DOCUMENTS

| | | |
|---|---|---|
| CA | 2423840 | 2/2002 |
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 A1 | 11/1984 |
| EP | 0898460 | 3/1999 |
| EP | 1017313 | 7/2000 |
| EP | 1107693 | 6/2001 |
| EP | 1145735 A2 | 10/2001 |
| EP | 1145736 A2 | 10/2001 |
| EP | 1292900 | 3/2003 |
| EP | 1307260 | 5/2003 |
| EP | 1331967 | 8/2003 |
| EP | 1335668 | 8/2003 |
| EP | 1341580 | 9/2003 |
| EP | 1404216 | 4/2004 |
| EP | 1333753 | 9/2004 |
| EP | 1525551 | 4/2005 |
| EP | 1558121 | 8/2005 |
| EP | 1558128 | 8/2005 |
| EP | 1558130 | 8/2005 |
| EP | 1558131 | 8/2005 |
| EP | 1558132 | 8/2005 |
| EP | 1558330 | 8/2005 |
| EP | 1558334 | 8/2005 |
| EP | 1562674 | 8/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |

| | | | |
|---|---|---|---|
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |
| WO | WO 2004/034881 A2 | 4/2004 |
| WO | WO 2004/034882 A2 | 4/2004 |
| WO | WO 2004/034883 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO 2007/150003 A2 | 12/2007 |

OTHER PUBLICATIONS

Yang et al.; Testing whether a prediction scheme is better than guess; Ch. 14 in Quantitative Neuroscience: Models, Algorithms, Diagnostics, and Therapeutic Applications; pp. 251-262, 2004.*
Remington's Pharmaceutical Sciences, latest edition, Mack Publishing Co., Easton Pennsylvania, 1990 pp. .Xii-XV.*
Leyde, Kent; U.S. Appl. No. 11/599,179, entitled "Systems and methods of reducing artifact in neurological stimulation systems," filed Nov. 14, 2006.
Leyde et al.; U.S. Appl. No. 12/020,507 entitled "Methods and systems for measuring a subject's susceptibility to a seizure," filed Jan. 25, 2008.
Snyder et al.; U.S. Appl. No. 12/020,450 entitled "Systems and methods for identifying a contra-ictal condition in a subject," filed Jan. 25, 2008.
Snyder et al.; U.S. Appl. No. 12/035,335 entitled "Methods and systems for characterizing and generating a patient-specific seizure prediction system," filed Feb. 21, 2008.
Snyder et al.; U.S. Appl. No. 12/053,312 entitled "Implantable systems and methods for identifying a contra-ictal condition in a subject," filed Mar. 21, 2008.
Leyde et al.; U.S. Appl. No. 12/343,376 entitled "Systems and method for recording clinical manifestations of a seizure," filed Dec. 23, 2008.
Brown et al.; U.S. Appl. No. 12/343,386 entitled "Housing for an implantable medical device," filed Dec. 23, 2008.
DiLorenzo, Daniel, U.S. Appl. No. 10/858,899, entitled "Closed-loop feedback-driven neuromodulation," filed Jun. 1, 2004.
DiLorenzo, Daniel, U.S. Appl. No. 11/706,630, entitled "Methods and systems for administering an appropriate pharmacological treatment to a patient for managing epilepsy and other neurological disorders," filed Feb. 14, 2007
DiLorenzo, Daniel, U.S. Appl. No. 11/743,607, entitled "Controlling a Subject's Susceptibility to a Seizure," filed May 2, 2007.
DiLorenzo, Daniel, U.S. Appl. No. 11/743,611, entitled "Providing Output Indicative of Subject's Disease State," May 2, 2007.
DiLorenzo, Daniel, U.S. Appl. No. 11/282,317 entitled "Closed-loop vagus nerve stimulation," filed Nov. 17, 2005.
Harris et al; U.S. Appl. No. 11/766,742, entitled "Minimally Invasive Monitoring Systems," filed Jun. 21, 2007.
Harris et al; U.S. Appl. No. 11/766,751, entitled "Minimally Invasive Monitoring Methods," filed Jun. 21, 2007.
Harris et al; U.S. Appl. No. 11/766,756, entitled "Methods and Systems for Facilitating Clinical Trials," filed Jun. 21, 2007.
Harris et al; U.S. Appl. No. 11/766,761, entitled "Minimally Invasive Monitoring Systems for Monitoring a Patient's Propensity for a Neurological Event," filed Jun. 21, 2007.
Harris, John, U.S. Appl. No. 11/734,190, entitled "Methods and Template Assembly for Implanting an Electrode Array in a Patient," filed Apr. 11, 2007.
Adjouadi, et al. A new mathematical approach based on orthogonal operators for the detection of interictal spikes in epileptogenic data. Biomed. Sci. Instrum. 2004; 40: 175-80.
Adjouadi, et al. Detection of interictal spikes and artifactual data through orthogonal transformations. J. Clin. Neurophysiol. 2005; 22(1):53-64.
Adjouadi, et al. Interictal spike detection using the Walsh transform. IEEE Trans. Biomed. Eng. 2004; 51(5): 868-72.
Aksenova, et al. Nonparametric on-line detection of changes in signal spectral characteristics for early prediction of epilepsy seizure onset. J. Automation and Information Sciences. 2004; 36(8): 35-45.
Aksenova, et al. On-line disharmony detection for early prediction of epilepsy seizure onset. 5th International Workshop Neural Coding 2003. Aulla (Italy) Sep. 20-25, 2003. (Abstract).
Andrzejak, et al. Bivariate surrogate techniques: necessity, strengths, and caveats. Physical Review E. 2003; 68: 066202-1-066202-15.
Andrzejak, et al. Testing the null hypothesis of the nonexistence of a preseizure state. Physical Review E. 2003; 67: 010901-1-010901-4.
Aschenbrenner-Scheibe, et al. How well can epileptic seizures be predicted? An evaluation of a nonlinear method. Brain. 2003; 126: 2616-26.
Bangham et al. Diffusion of univalent ions across the lamellae of swollen phospholipids. 1965. J Mol. Biol. 13: 238-252.
Baruchi, et al. Functional holography of complex networks activity—From cultures to the human brain. Complexity. 2005; 10(3): 38 R 51.
Baruchi, et al. Functional holography of recorded neuronal networks activity. Neuroinformatics. 2004; 2(3): 333-51.
Ben-Hur, et al. Detecting stable clusters using principal component analysis. Methods Mol. Biol. 2003; 224: 159-82.
Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Identification, and Control. 2003; 377-201: 313-317.

Bhattacharya, et al. Enhanced phase synchrony in the electroencephalograph gamma band for musicians while listening to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versphase couplings. IEEE Trans. Biomed. Eng. 2003; 50(5):571-83.

Crichton, Michael, "Terminal Man", 1972, Ballantine Books, NY, NY, pp. 21-24, 32-33, 70-71, and 74-81.

D'Alessandro, et al. Epileptic seizure prediction using hybrid feature selection over multiple intracranial EEG electrode contacts: a report of four patients. IEEE Trans. Biomed. Eng. 2003; 50 (5): 603-15.

D'Alessandro, et al. A multi-feature and multi-channel univariate selection process for seizure prediction. Clin. Neurophysiol. 2005; 116(3): 506-16.

Drury, et al. Seizure prediction using scalp electroencephalogram. Exp. Neurol. 2003; 184 Suppl 1:S9-18.

Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.

Ebersole, J. S. In search of seizure prediction: a critique. Clin. Neurophysiol. 2005; 116(3): 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, A report of the therapeutics and technology assessment subcommittee of the American Academy of Neurology. Neurology.53: 666-669.

Gardner, A. B. A Novelty Detection Approach to Seizure Analysis from Intracranial EEG. Georgia Institute of Technology. Apr. 2004. A dissertation available at http://etd.gatech.edu/theses/available/etd-04122004-132404/unrestricted/gardner_andrew_b_200405_phd.pdf. Accessed Feb. 28, 2006.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. ORNL/TM-2000/333 Oak Ridge National Laboratory. Nov. 2000. Available at http://computing.ornl.gov/cse_home/staff/hively/NBICradaAnnualRpt FY00.pdf. Accessed Feb. 28, 2006.

Hjorth, B. Source derivation simplifies topographical EEG interpretation. Am. J. EEG Technol. 1980; 20: 121-132.

Hsu, et al. A practical guide to support vector classification. Technical report, Department of Computer Science and Information Technology, National Taiwan University, 2003. Available at http://www.csie.ntu.edu.tw/~cjlin/papers/guide/guide.pdf. Accessed Feb. 28, 2006.

Huynh, J. A. Evaluation of Gene Selection Using Support Vector Machine Recursive Feature Elimination. Arizona State University. May 26, 2004. (28 pages).

Huynh, J. A. Evaluation of Gene Selection Using Support Vector Machine Recursive Feature Elimination. Presentation slides. (41 pages) (May 26, 2004).

Iasemidis, et al. Adaptive epileptic seizure prediction system. IEEE Trans. Biomed. Eng. 2003; 50 (5):616-27.

Iasemidis, et al. Automated Seizure Prediction Paradigm. Epilepsia. 1998; vol. 39, pp. 56.

Iasemidis, et al. Chaos Theory and Epilepsy. The Neuroscientist. 1996; 2:118-126.

Iasemidis, et al. Comment on "Inability of Lyapunov exponents to predict epileptic seizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focwith Extrafocal Sites in Temporal Lobe Epilepsy (TLE). Ann. Neurol. 1997; 42, pp. 429. pp. M146.

Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-64.

Iasemidis, et al. Long-term prospective on-line real-time seizure prediction. Clin. Neurophysiol. 2005; 116(3):532-44.

Iasemidis, et al. Long-Time-Scale Temporo-spatial Patterns of Entrainment of Preictal Electrocorticographic Data in Human Temporal Lobe Epilepsy. Epilepsia. 1990; 31(5):621.

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.

Iasemidis, et al. Modelling of ECoG in temporal lobe epilepsy. Biomed. Sci. Instrum. 1988; 24: 187-93.

Iasemidis, et al. Nonlinear Dynamics of EcoG Data in Temporal Lobe Epilepsy. Electroencephalography and Clinical Neurophysiology. 1998; 5, pp. 339.

Iasemidis, et al. Phase space topography and the Lyapunov exponent of electrocorticograms in partial seizures. Brain Topogr. 1990; 2(3):187-201.

Iasemidis, et al. Preictal Entrainment of a Critical Cortical Mass is a Necessary Condition for Seizure Occurrence. Epilepsia. 1996; 37, suppl. 5. pp. 90.

Iasemidis, et al. Preictal-Postictal Versus Postictal Analysis for Epileptogenic Focus Localization. J. Clin. Neurophysiol. 1997; 14, pp. 144.

Iasemidis, et al. Quadratic binary programming and dynamic system approach to determine the predictability of epileptic seizures. Journal of Combinatorial Optimization. 2001; 5: 9-26.

Iasemidis, et al. Quantification of Hidden Time Dependencies in the EEG within the Framework of Non-Linear Dynamics. World Scientific. 1993; pp. 30-47.

Iasemidis, et al. Spatiotemporal dynamics of human epileptic seizures. World Scientific. 1996; pp. 26-30.

Iasemidis, et al. Spatiotemporal Evolution of Dynamical Measures Precedes Onset of Mesial Temporal Lobe Seizures. Epilepsia. 1994; 358, pp. 133.

Iasemidis, et al. Spatiotemporal Transition to Epileptic Seizures: A Nonlinear Dynamical Analysis of Scalp and Intracranial EEG Recordings. (in Silva, F.L. Spatiotemporal Models in Biological and Artificial Systems. Ohmsha IOS Press. 1997; 37, pp. 81-88.).

Iasemidis, et al. The evolution with time of the spatial distribution of the largest Lyapunov exponent on the human epileptic cortex. World Scientific. 1991; pp. 49-82.

Iasemidis, et al. The Use of Dynamical Analysis of EEG Frequency Content in Seizure Prediction. American Electroencephalographic Society Annual Meeting, Oct. 1993.

Iasemidis, et al. Time Dependencies in Partial Epilepsy. 1993; 34, pp. 130-131.

Iasemidis, et al. Time dependencies in the occurrences of epileptic seizures. Epilepsy Res. 1994; 17(1):81-94.

Iasemidis, L. D. Epileptic seizure prediction and control. IEEE Trans. Biomed. Eng. 2003; 50 (5):549-58.

Jerger, et al. Early seizure detection. Journal of Clin. Neurophysiol. 2001; 18(3):259-68.

Jerger, et al. Multivariate linear discrimination of seizures. Clin. Neurophysiol. 2005; 116 (3):545-51.

Jouny, et al. Characterization of epileptic seizure dynamics using Gabor atom density. Clin. Neurophysiol. 2003; 114(3):426-37.

Jouny, et al. Signal complexity and synchrony of epileptic seizures: is there an identifiable preictal period? Clin. Neurophysiol. 2005; 116(3):552-8.

Kapiris, et al. Similarities in precursory features in seismic shocks and epileptic seizures. Europhys. Lett. 2005; 69(4):657-663.

Katz, et al. Does interictal spiking change prior to seizures? Electroencephalogr. Clin. Neurophysiol. 1991; 79(2):153-6.

Kerem, et al. Forecasting epilepsy from the heart rate signal. Med. Biol. Eng. Comput. 2005; 43(2):230-9.

Khalilov, et al. Epileptogenic actions of GABA and fast oscillations in the developing hippocampus. Neuron. 2005; 48(5):787-96.

Korn, et al. Is there chaos in the brain? II. Experimental evidence and related models. C. R. Biol. 2003; 326 (9):787-840.

Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006 (106 pp).

Kreuz, et al. Measure profile surrogates: a method to validate the performance of epileptic seizure prediction algorithms. Phys. Rev. E. 2004; 69(6 Pt 1):061915-1-9.

Lachaux, et al. Measuring phase synchrony in brain signals. Hum. Brain Mapp. 1999; 8(4):194-208.

Lai, et al. Controlled test for predictive power of Lyapunov exponents: their inability to predict epileptic seizures. Chaos. 2004; 14(3):630-42.

Lai, et al. Inability of Lyapunov exponents to predict epileptic seizures. Phys. Rev. Lett. 2003; 91(6):068102-1-4.

Latka, et al. Wavelet analysis of epileptic spikes. Phys. Rev. E. 2003; 67(5 Pt 1):052902 (6 pages).

Le Van Quyen, et al. Anticipating epileptic seizures in real time by a non-linear analysis of similarity between EEG recordings. Neuroreport. 1999; 10(10):2149-55.

Le Van Quyen, et al. Author's second reply. The Lancet. 2003; 361:971.

Le Van Quyen, et al. Comparison of Hilbert transform and wavelet methods for the analysis of neuronal synchrony. J. Neurosci. Methods. 2001; 111(2):83-98.

Le Van Quyen, et al. Nonlinear analyses of interictal EEG map the brain interdependences in human focal epilepsy. Physica D. 1999; 127:250-266.

Le Van Quyen, et al. Preictal state identification by synchronization changes in long-term intracranial EEG recordings. Clin. Neurophysiol. 2005; 116(3):559-68.

Le Van Quyen, M. Anticipating epileptic seizures: from mathematics to clinical applications. C. R. Biol. 2005; 328(2):187-98.

Lehnertz, et al. Nonlinear EEG analysis in epilepsy: its possible use for interictal focus localization, seizure anticipation, and prevention. J. Clin. Neurophysiol. 2001; 18(3):209-22.

Lehnertz, et al. Seizure prediction by nonlinear EEG analysis. IEEE Eng. Med. Biol. Mag. 2003; 22(1):57-63.

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy—an overview. Int. J. Psychophysiol. 1999; 34(1):45-52.

Lemos, et al. The weighted average reference montage. Electroencephalogr. Clin. Neurophysiol. 1991; 79(5):361-70.

Li, et al. Fractal spectral analysis of pre-epileptic seizures in terms of criticality. J. Neural Eng. 2005; 2(2):11-16.

Li, et al. Linear and nonlinear measures and seizure anticipation in temporal lobe epilepsy. J. Comput. Neurosci. 2003; 15(3):335-45.

Li, et al. Non-linear, non-invasive method for seizure anticipation in focal epilepsy. Math. Biosci. 2003; 186(1):63-77.

Litt, et al. Prediction of epileptic seizures. Lancet Neurol. 2002; 1(1):22-30.

Litt, et al. Seizure prediction and the preseizure period. Curr. Opin. Neurol. 2002; 15(2):173-7.

Maiwald, et al. Comparison of three nonlinear seizure prediction methods by means of the seizure prediction characteristic. Physica D. 2004; 194:357-368.

Mangasarian, et al. Lagrangian Support Vector Machines. Journal of Machine Learning Research. 2001; 1:161-177.

Martinerie, et al. Epileptic seizures can be anticipated by non-linear analysis. Nat. Med. 1998; 4 (10):1173-6.

McSharry, et al. Comparison of predictability of epileptic seizures by a linear and a nonlinear method. IEEE Trans. Biomed. Eng. 2003; 50(5):628-33.

McSharry, et al. Linear and non-linear methods for automatic seizure detection in scalp electro-encephalogram recordings. Med. Biol. Eng. Comput. 2002; 40(4):447-61.

McSharry, P. E. Detection of dynamical transitions in biomedical signals using nonlinear methods. Lecture Notes in Computer Science 2004; 3215:483-490.

Meng, et al. Gaussian mixture models of ECoG signal features for improved detection of epileptic seizures. Med. Eng. Phys. 2004; 26(5):379-93.

Mizuno-Matsumoto, et al. Wavelet-crosscorrelation analysis can help predict whether bursts of pulse stimulation will terminate after discharges. Clin. Neurophysiol. 2002; 113(1):33-42.

Mormann, et al. Automated detection of a preseizure state based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53(3):173-85.

Mormann, et al. Mean phase coherence as a measure for phase synchronization and its application to the EEG of epilepsy patients. Physica D. 2000; 144:358-369.

Mormann, et al. On the predictability of epileptic seizures. Clin. Neurophysiol. 2005; 116 (3):569-87.

Mormann, et al. Seizure anticipation: from algorithms to clinical practice. Curr. Opin. Neurol. 2006; 19(2):187-93.

Navarro, et al. Seizure anticipation in human neocortical partial epilepsy. Brain. 2002; 125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26 (1):55-60.

Osorio, et al. Automated seizure abatement in humans using electrical stimulation. Ann. Neurol. 2005; 57(2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.

Pittman, V. Flexible Drug Dosing Produces Less Side-effects In People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18(3):223-45.

Rahimi, et al. On the Effectiveness of Aluminum Foil Helmets: An Empirical Study. Available at http://people.csail.mit.edu/rahimi/helmet/. Accessed Mar. 2, 2006.

Robinson, et al. Steady States and Global Dynamics of Electrical Activity in the Cerebral Cortex. Phys. Rev. E. 1998; (58):3557-3571.

Rudrauf, et al. Frequency flows and the time-frequency dynamics of multivariate phase synchronization in brain signals. NeuroImage. 2005. (19 pages.).

Saab, et al. A system to detect the onset of epileptic seizures in scalp EEG. Clin. Neurophysiol, 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampin Limbic Epilepsy. Neurology. 1995; 45, Suppl. 4, pp. A 404.

Sackellares et al. Epileptic Seizures as Neural Resetting Mechanisms. Epilepsia. 1997; vol. 38, Sup. 3.

Sackellares et al. Measurement of Chaos to Localize Seizure Onset. Epilepsia. 1989; 30 (5):663.

Sackellares et al. Relationship Between Hippocampal Atrophy and Dynamical Measures of EEG in Depth Electrode Recordings. American Electroencephalographic Society Annual Meeting, Sep. 1995. pp. A105.

Sackellares, J. C. Epilepsy—when chaos fails. In: chaos in the brain? Eds. K. Lehnertz & C.E. Eiger. World Scientific. 2000 (22 pages).

Salant, et al. Prediction of epileptic seizures from two-channel EEG. Med. Biol. Eng. Comput. 1998; 36(5):549-56.

Schelter, et al. Testing for directed influences among neural signals using partial directed coherence. J. Neurosci. Methods. 2006; 152(1-2):210-9.

Schindler, et al. EEG analysis with simulated neuronal cell models helps to detect pre-seizure changes. Clin. Neurophysiol. 2002; 113(4):604-14.

Schwartzkroin, P. Origins of the Epileptic State. Epilepsia. 1997; 38, supply. 8, pp. 853-858.

Sheridan, T. Humans and Automation. NY: John Wiley. 2002.

Shoeb et al. Patient-specific seizure detection. MIT Computer Science and Artificial Intelligence Laboratory. 2004; pp. 193-194.

Staba, et al. Quantitative analysis of high-frequency oscillations (80-500 Hz) recorded in human epileptic hippocampand entorhinal cortex. J. Neurophysiol. 2002; 88(4):1743-52.

Stefanski, et al. Using chaos synchronization to estimate the largest Lyapunov exponent of nonsmooth systems. Discrete Dynamics in Nature and Society. 2000; 4:207-215.

Subasi, et al. Classification of EEG signals using neural network and logistic regression. Computer Methods Programs Biomed. 2005; 78(2):87-99.

Szoka et al. Procedure for preparation of liposomes with large internal aqueospace and high capture volume by reverse phase evaporation. 1978. Proc. Natl Acad. Sci. USA. 75: 4194-4198.

Tass, et al. Detection of n: m Phase Locking from Noisy Data: Application to Magnetoencephalography. Physical Review Letters. 1998; 81(15):3291-3294.

Terry, et al. An improved algorithm for the detection of dynamical interdependence in bivariate time-series. Biol. Cybern. 2003; 88(2)129-36.

Tetzlaff, et al. Cellular neural networks (CNN) with linear weight functions for a prediction of epileptic seizures. Int"1. J. of Neural Systems. 2003; 13(6):489-498.

Theiler, et al. Testing for non-linearity in time series: the method of surrogate data. Physica D. 1992; 58:77-94.

Tsakalis, K. S. Prediction and control of epileptic seizures: Coupled oscillator models. Arizona State University. (Slide: 53 pages) (No date).

Van Drongelen, et al. Seizure anticipation in pediatric epilepsy: use of Kolmogorov entropy. Pediatr. Neurol. 2003; 29(3): 207-13.

Van Putten, M. Nearest neighbor phase synchronization as a measure to detect seizure activity from scalp EEG recordings. J. Clin. Neurophysiol. 2003; 20(5):320-5.

Venugopal, et al. A new approach towards predictability of epileptic seizures: KLT dimension. Biomed Sci. Instrum. 2003; 39:123-8.

Vonck, et al. Long-term amygdalohippocampal stimulation for refractory temporal lobe epilepsy. Ann. Neurol. 2002; 52(5):556-65.

Vonck, et al. Long-term deep brain stimulation for refractory temporal lobe epilepsy. Epilepsia. 2005; 46(Suppl 5):98-9.

Vonck, et al. Neurostimulation for refractory epilepsy. Acta. Neurol. Belg. 2003; 103(4):213-7.

Weiss, P. Seizure prelude found by chaos calculation. Science News. 1998; 153(20):326.

Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.

Widman, et al. Reduced signal complexity of intracellular recordings: a precursor for epileptiform activity? Brain Res. 1999; 836(1-2):156-63.

Winterhalder, et al. Sensitivity and specificity of coherence and phase synchronization analysis. (In Press) Phys. Lett. A. 2006.

Winterhalder, et al. The seizure prediction characteristic: a general framework to assess and compare seizure prediction methods. Epilepsy Behav. 2003; 4(3):318-25.

Yang, et al. A supervised feature subset selection technique for multivariate time series. Available at http://infolab.usc.edu/DocsDemos/fsdm05.pdf. Accessed Mar. 2, 2006.

Yang, et al. CLe Ver: A feature subset selection technique for multivariate time series. T. B. Ho, D. Cheung, and H. Liu (Eds.): PAKDD. 2005; LNAI 3518: 516-522.

Yang, et al. Relation between Responsiveness to Neurotransmitters and Complexity of Epileptiform Activity in Rat Hippocampal CA1 Neurons. Epilepsia. 2002; 43(11):1330-1336.

Yatsenko, et al. Geometric Models, Fiber Bundles, and Biomedical Applications. Proceedings of Institute of Mathematics of NAS of Ukraine. 2004; 50 (Part 3):1518R1525.

Zaveri et al. Time-Frequency Analyses of Nonstationary Brain Signals. Electroencephalography and Clinical Neurophysiology. 1991; 79, pp. 28P-29P.

Zhang, et al. High-resolution EEG: cortical potential imaging of interictal spikes. Clin. Neurophysiol. 2003; 114(10):1963-73.

DiLorenzo, Daniel; U.S. Appl. No. 12/177,060 entitled "Closed-loop feedback-driven neuromodulation," filed Jul. 21, 2008.

Bland et al.; U.S. Appl. No. 12/180,996 entitled "Patient advisory device," filed Jul. 28, 2008.

Franaszczuk et al.; An autoregressive method for the measurement of synchronization of interictal and ictal EEG signals; Biological Cybernetics, vol. 81; No. 1; pp. 3-9; 1999.

\* cited by examiner

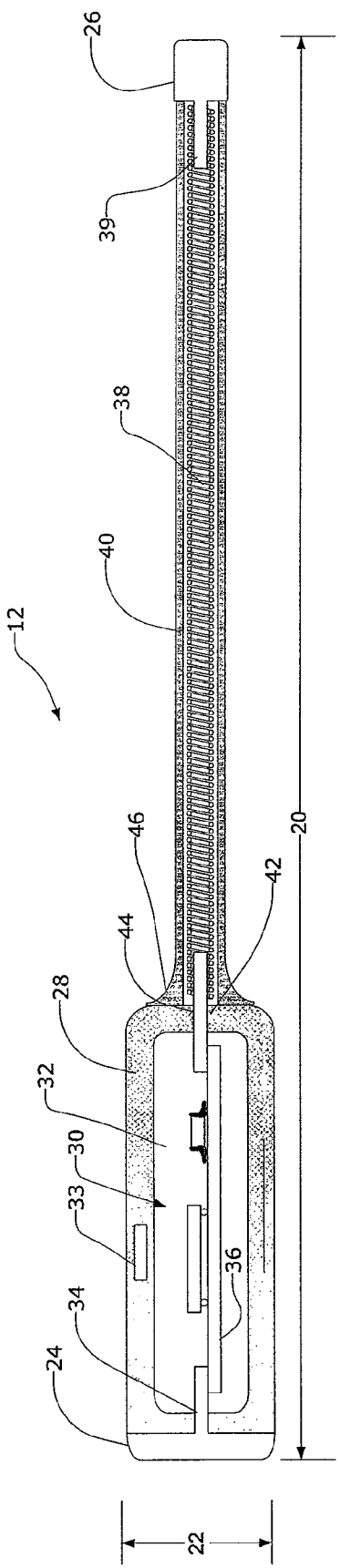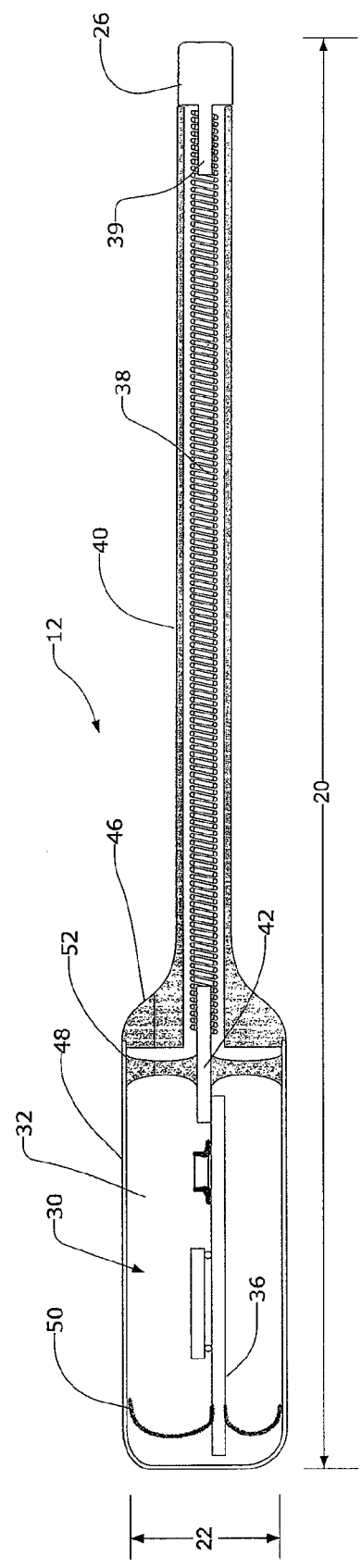

MINIMALLY INVASIVE SYSTEM FOR SELECTING PATIENT-SPECIFIC THERAPY PARAMETERS

CROSS-REFERENCED TO RELATED APPLICATIONS

The present application claims benefit of U.S. Provisional Patent Application Ser. No. 60/805,710, filed Jun. 23, 2006, to Harris et al., entitled "Implantable Ambulatory Brain Monitoring System," the complete disclosure of which is incorporated herein by reference.

BACKGROUND OF THE INVENTION

The present invention relates generally to systems and methods for sampling one or more physiological signals from a patient. More specifically, the present invention relates to long term, ambulatory monitoring of one or more neurological signals for selecting therapy parameters for a patient.

Epilepsy is a disorder of the brain characterized by chronic, recurring seizures. Seizures are a result of uncontrolled discharges of electrical activity in the brain. A seizure typically manifests itself as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool.

A single seizure most often does not cause significant morbidity or mortality, but severe or recurring seizures (epilepsy) results in major medical, social, and economic consequences. Epilepsy is most often diagnosed in children and young adults, making the long-term medical and societal burden severe for this population of patients. People with uncontrolled epilepsy are often significantly limited in their ability to work in many industries and usually cannot legally drive an automobile. An uncommon, but potentially lethal form of seizure is called status epilepticus, in which a seizure continues for more than 30 minutes. This continuous seizure activity may lead to permanent brain damage, and can be lethal if untreated.

While the exact cause of epilepsy is often uncertain, epilepsy can result from head trauma (such as from a car accident or a fall), infection (such as meningitis), or from neoplastic, vascular or developmental abnormalities of the brain. Most epilepsy, especially most forms that are resistant to treatment (i.e., refractory), are idiopathic or of unknown causes, and is generally presumed to be an inherited genetic disorder.

While there is no known cure for epilepsy, the primary treatment for these epileptic patients are a program of one or more anti-epileptic drugs or "AEDs." Chronic usage of anti-convulsant and antiepileptic medications can control seizures in most people. An estimated 70% of patients will respond favorably to their first AED monotherapy and no further medications will be required. However, for the remaining 30% of the patients, their first AED will fail to fully control their seizures and they will be prescribed a second AED—often in addition to the first—even if the first AED does not stop or change a pattern or frequency of the patient's seizures. For those that fail the second AED, a third AED will be tried, and so on. Patients who fail to gain control of their seizures through the use of AEDs are commonly referred to as "medically refractory."

For those patients with infrequent seizures, the problem is further compounded by the fact that they must remain on the drug for many months before they can discern whether there is any benefit. As a result, physicians are left to prescribe AEDs to these patients without clear and timely data on the efficacy of the medication. Because these drugs are powerful neural suppressants and are associated with undesirable side-effects and sedation, it is important to minimize the use and dosage of these drugs if the patient is not experiencing benefit.

A major challenge for physicians treating epileptic patients is gaining a clear view of the effect of a medication or incremental medications on the patient's condition. Presently, the standard metric for determining efficacy of the medication is for the patient or for the patient's caregiver to keep a diary of seizure activity. However, it is well recognized that such self-reporting is often of poor quality because patients often do not realize when they have had a seizure, or fail to accurately record seizures. In addition, patients often have "sub-clinical" seizures where the brain experiences a seizure, but the seizure does not manifest itself clinically, and the patient has no way of making note of such seizures. Due to such deficiencies in assessing the efficacy of the AEDs, patients and physicians are unable to reliably determine the effectiveness of the AEDs. Consequently, patient's are often given dosages and dosing schedules that are much more than needed, and the patient is subject to the unwanted side effects associated with the AEDs.

Consequently, what are needed are methods and systems that are capable of long-term, out-patient monitoring of epileptic patients. It would further be desirable if the long-term monitoring could be processed into appropriate metrics that can quantify the clinical benefit of the medication or other therapies and allow for intelligent titration of the medications. It would also be desirable to have system that could record seizure activity, to enable the meaningful study of patients with infrequent seizures.

SUMMARY OF THE INVENTION

The present invention provides methods and systems for monitoring one or more physiological signals from the patient. In preferred embodiments, the present invention provides minimally-invasive systems that provide for the long-term, ambulatory monitoring of patient's brain activity. The systems of the present invention will typically include one or more implantable devices that are capable of sampling and transmitting a signal that is indicative of the patient's brain activity to a data collection device that is external to the patient's body. The ambulatory systems of the present invention provide for substantially continuous sampling of brain wave electrical signals (e.g., electroencephalography or "EEG" and electrocorticogram "ECoG", which are hereinafter referred to collectively as "EEG").

A patient could wear their external data collection device at all times of the day (except while showering, etc.). At the physicians' office, the data from the external data collection device could be uploaded into a physician's computer, which could then automatically analyze the stored EEG data and calculate certain metrics that would provide insight into the patient's condition and the efficacy of their therapy. For example, such metrics may allow the epileptologist to assess seizure frequency, monitor for sub-clinical seizures, determine the efficacy of treatment, determine the effect of adjustments of the dosage of the AED, determine the effects of adjustments of the type of AED, adjust parameters of electrical stimulation, or the like.

The systems of the present invention typically include one or more low power implantable devices for sampling the patient's EEG signal. The implantable devices are in communication with a device that is external to the patient's body. The external device is typically configured to transmit power into the implantable device and to store the EEG signal that is sampled by the implantable device. The implantable device and the external device will be in communication with each other through a wireless communication link. While any number of different wireless communication links may be used, in preferred embodiments the systems of the present invention uses a high-frequency communication link. Such a communication link enables transmission of power into the implantable device and facilitates data transfer to and from the implantable device In one aspect, the present invention provides a method for selecting a therapy for a patient suffering from a neurological or psychiatric condition. The method comprises implanting a monitoring device between at least one layer of the scalp and the skull and commencing a first therapy. A physiological signal from the patient is monitored with the implanted device for a first time period after commencement of the first therapy. A second therapy is commenced and a physiological signal from the patient is monitored with the implanted device for a second time period after commencement of the second therapy. The physiological signals from the first time period and second time period are processed and analyzed to select an appropriate therapy for the patient.

In one preferred embodiment, the neurological condition comprises epilepsy and the first and second therapy comprises different pharmacological agents. In other embodiments, the therapy may comprise electrical stimulation of the same or different portions of the nervous system (e.g., deep brain, cortical surface, cranial nerve, peripheral nerve, etc.)

In some embodiments processing of the physiological signals from the first time period and second time period comprises measuring seizure activity data from each of the time periods. Seizure activity data comprises a number a clinical seizures during the first time period, a number of sub-clinical seizures during the first time period, seizure duration, seizure patterns, seizure frequency, and time of day of seizure occurrence, or any combination thereof.

The monitoring devices implanted in the patient may take a variety of different forms, but in some configurations the devices are leadless. The leadless devices may have an internal power source, but they may also be devoid of a power source and externally powered via a signal (e.g., radiofrequency signal) generated in an external device. The signal from the external device may power the implanted devices and interrogate the electronic components to facilitate sampling of the physiological signals. Data indicative of the sampled physiological signals may be encoded in a data signal that is wirelessly transmitted to the external device. The physiological signals may thereafter be stored in a memory that is external to the patient's body.

In another aspect, the present invention provides a method for optimizing parameters of a selected therapy for patient having a neurological or psychiatric condition. The method comprises implanting a device in between a patient's skull and at least one layer of the scalp and commencing a therapy. A physiological signal is sampled from the patient with the implanted device after commencement of the therapy for a first time period. At least one parameter of the therapy is changed and the physiological signal is sampled from the patient with the implanted device for a second time period after the at least one parameter of the therapy is changed. The physiological signal from the first time period and second time period are processed. The processed physiological signals from the first and second time periods are thereafter analyzed to determine desirable parameters for the patient's therapy.

In one configuration, the neurological condition is epilepsy and processing comprises measuring seizure activity data from the first and second time periods. Seizure activity data typically comprises at least one of a number a clinical seizures during the first and second time period, a number of sub-clinical seizures during the first and second time period, seizure duration during the first and second time period, seizure patterns during the first and second time period, seizure frequency during the first and second time period, and time of seizure occurrence during the first and second time period.

The monitoring devices implanted in the patient may take a variety of different forms, but in some configurations the devices are leadless. The leadless devices may have an internal power source, but they may also be externally powered via a signal (e.g., radiofrequency signal) generated in an external device. The signal from the external device may power the implanted devices and interrogate the electronic components to facilitate sampling of the physiological signals. Data indicative of the sampled physiological signals may be encoded in a data signal that is wirelessly transmitted to the external device. The physiological signals may thereafter be stored in a memory in the external device.

To help facilitate selection of the appropriate parameters for the particular patient, the methods of the present invention may generate a report for the physician and/or patient. The report may indicate the seizure activity data for the first and second time period, a chart/graph and/or an analysis of the differences in the seizure activity data for the different time periods, and a recommendation for the parameters of the patient-specific therapy.

The therapy may be a pharmacological therapy (such as an AED, for patient's suffering from epilepsy). The parameters that may be varied include at least one of a dosage, dosage frequency, form of the AED, and formulation of the AED. In other embodiments, the therapy may be electrical stimulation (such as deep brain stimulation, cortical stimulation, cranial nerve stimulation, peripheral nerve stimulation, or the like). The parameters that may be varied for such therapy includes at least one of frequency, pulse amplitude, pulse width, pulses per burst, burst frequency, burst/no-burst, and duty cycle.

In a further aspect, the present invention provides a method for titrating parameters of a pharmacological agent for treating a patient having epilepsy. The method comprises implanting a leadless device in between a patient's skull and at least one layer of the scalp and commencing an anti-epileptic drug therapy. Sampling of an EEG signal from the patient is performed with the implanted device after commencement of the anti-epileptic drug therapy. A data signal that is encoded with the sampled EEG signal is transmitted from the implanted device to a portable external device for a first time period. At least one parameter of the anti-epileptic drug therapy is modified and An EEG signal from the patient is sampled with the implanted device after commencement of the anti-epileptic drug therapy with the at least one adjusted parameter. The data signal that is encoded with the sampled EEG signal is transmitted from the implanted device to a portable external device for a second time period. The sampled EEG signals from the first time period and second time period are processed to generate seizure activity data. The seizure activity data from the first and second time periods are analyzed to determine desirable parameters for the patient's therapy.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A is a cross-sectional view of another embodiment of an implantable device that is encompassed by the present invention.

FIG. 3B is a cross-sectional view of another embodiment of the implantable device in which a conductive can forms a housing around the electronic components and acts as an electrode.

DETAILED DESCRIPTION OF THE INVENTION

Figure 1A:
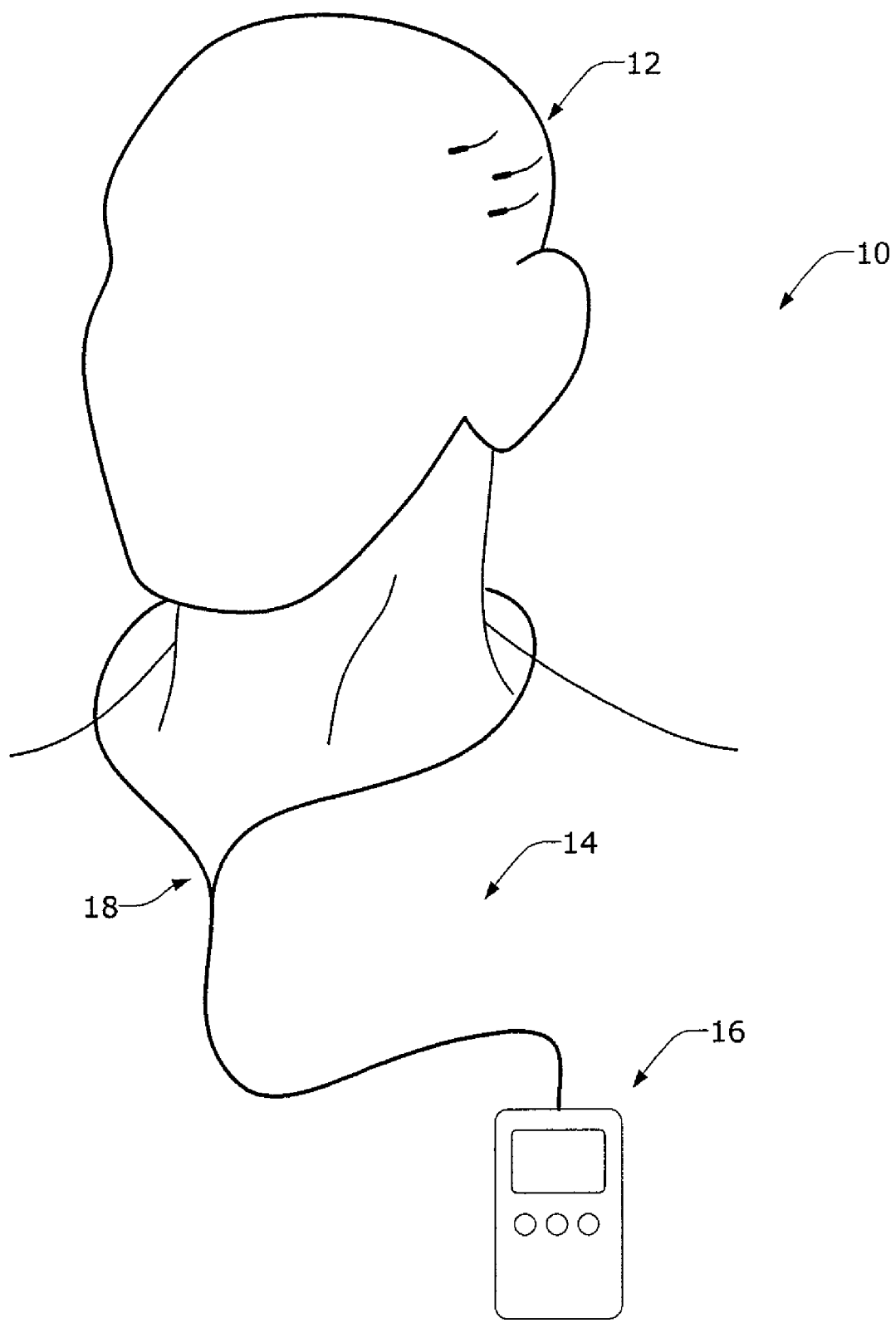
FIG. 1A illustrates a simplified system embodied by the present invention which comprises one or more implantable devices in communication with an external device.

Certain specific details are set forth in the following description and figures to provide an understanding of various embodiments of the invention. Certain well-known details, associated electronics and devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

The term "condition" is used herein to generally refer to the patient's underlying disease or disorder—such as epilepsy, depression, Parkinson's disease, headache disorder, etc. The term "state" is used herein to generally refer to calculation results or indices that are reflective a categorical approximation of a point (or group of points) along a single or multi-variable state space continuum of the patient's condition. The estimation of the patient's state does not necessarily constitute a complete or comprehensive accounting of the patient's total situation. As used in the context of the present invention, state typically refers to the patient's state within their neurological condition. For example, for a patient suffering from an epilepsy condition, at any point in time the patient may be in a different states along the continuum, such as an ictal state (a state in which a neurological event, such as a seizure, is occurring), a pre-ictal state (which is a neurological state that immediately precedes the ictal state), a pro-ictal state (a state in which the patient has an increased risk of transitioning to the ictal state), an inter-ictal state (a state in between ictal states), a contra-ictal state (a protected state in which the patient has a low risk of transitioning to the ictal state within a calculated or predetermined time period), or the like. A pro-ictal state may transition to either an ictal or inter-ictal state. A pro-ictal state that transitions to an ictal state may also be referred to herein as a "pre-ictal state."

The estimation and characterization of "state" may be based on one or more patient dependent parameters from the a portion of the patient's body, such as electrical signals from the brain, including but not limited to electroencephalogram signals and electrocorticogram signals "ECoG" or intracranial EEG (referred to herein collectively as EEG"), brain temperature, blood flow in the brain, concentration of AEDs in the brain or blood, changes thereof, etc.). While parameters that are extracted from brain-based signals are preferred, the present invention may also extract parameters from other portions of the body, such as the heart rate, respiratory rate, blood pressure, chemical concentrations, etc.

An "event" is used herein to refer to a specific event in the patient's condition. Examples of such events include transition from one state to another state, e.g., an electrographic onset of seizure, end of seizure, or the like. For conditions other than epilepsy, the event could be an onset of a migraine headache, onset of a depressive episode, a tremor, or the like.

The occurrence of a seizure may be referred to as a number of different things. For example, when a seizure occurs, the patient is considered to have exited a "pre-ictal state" or "pro-ictal state" and has transitioned into the "ictal state". However, the electrographic onset of the seizure (one event) and/or the clinical onset of the seizure (another event) have also occurred during the transition of states.

A patient's "propensity" for a seizure is a measure of the likelihood of transitioning into the ictal state. The patient's propensity for seizure may be estimated by determining which "state" the patient is currently in. As noted above, the patient is deemed to have an increased propensity for transitioning into the ictal state (e.g., have a seizure) when the patient is determined to be in a pro-ictal state. Likewise, the patient may be deemed to have a low propensity for transitioning into the ictal state when it is determined that the patient is in a contra-ictal state.

The methods, devices and systems of the present invention are useful for long-term, ambulatory sampling and analysis of one or more physiological signals, such as a patient's brain activity. In one preferred embodiment, the system of the present invention may be used to monitor and store one or more substantially continuously sampled EEG signals from the patient, while providing a minimal inconvenience to the patient. Attempts at developing ambulatory monitoring systems in the past have relied on an array of electrodes being placed on the patient's head and scalp with adhesive. Unfortunately, such systems are poorly tolerated by patients and are impractical for the duration of time needed for the accurate evaluation of the patient's EEG and evaluation of the efficacy of the treatment the patients are undergoing. Unlike conventional ambulatory EEG systems, the ambulatory monitoring systems of the present invention typically include one or more devices that are implanted in a minimally invasive fashion in the patient and will be largely unnoticed by a patient as they go about their day-to-day activities. The implantable devices may be in wireless communication with an external device that may be carried by the patient or kept in close proximity to the patient. Consequently, the ambulatory monitoring systems of the present invention are conducive to longer, more effective monitoring of the patient (e.g., one week or longer, one month or longer, two months or longer, three months or longer, six months or longer, one year or longer, etc.).

The methods, devices and systems of the present invention may also find use in an emergency room or neurological intensive care units (ICU). For example, the systems may be used to monitor patients who have complex, potentially life-threatening neurological illnesses or brain injuries. Neuro ICUs may monitor patients who have suffered (or thought to have suffered) a stroke (e.g., cerebral infarction, transient ischemic attacks, intracerebral hemorrhage, aneurismal subarachnoid hemorrhage, arteriovenous malformations, dural sinus thrombosis, etc.), head trauma, spinal cord injury, tumors (e.g., spinal cord metastases, paraneoplastic syndromes), infections (e.g., encephalitis, meningitis, brain abscess), neuromuscular weakness (e.g., Guillain-barre syndrome, myasthenia gravis), eclampsia, neuropleptic malignant syndrome, CNS vasculitis, migraine headaches, or the like.

The neuro-ICUs require the ability to monitor the patient's neurological condition for a long period of time to identify issues and diagnose the patient before permanent neurological damage occurs. Because the systems of the present invention are able to provide real-time monitoring of a patient's EEG and many embodiments have the ability to detect or predict neurological events, such systems will be beneficial to patients and the staff of the ICU to allow the neurologist and support staff to detect and/or prevent complications that may arise from the patient's neurological condition, before the patient's condition deteriorates.

For example, a patient who is suffering from head trauma may be outfitted with a system of the present invention and because the implantable portions are MRI safe, the patient's may still undergo MRI sessions. Furthermore, the systems of the present invention may also be used to continuously monitor a patient's response to a drug therapy while the patient is in the neuro-ICU and when the patient leaves the neuro-ICU.

For epilepsy patients in particular, the monitoring systems of the present invention may be used in conjunction with, or as an alternative to, the in-patient video-EEG monitoring that occurs in the EMU. If used as an alternative to in-patient video-EEG monitoring, in some embodiments it may be desirable to provide one or more video recorders in the patient's home to provide time-synced video recording of the patient as they live with their ambulatory monitoring system. In some embodiments, it may be desirable to provide a patient-mounted video system so as to allow video-monitoring of the patient outside of their home. Such a video system may or may not be in communication with the ambulatory monitoring system of the present invention; but both the video and the monitored EEG signals should be time-synced and analyzed together by the physician to assess the patient's condition and/or efficacy of any therapy that the patient may be undergoing.

The systems and methods of the present invention may incorporate EEG analysis software to estimate and monitor the patient's brain state substantially in real-time. The EEG analysis software may include a safety algorithm, a seizure prediction algorithm and/or a seizure detection algorithm that uses one or more extracted features from the EEG signals (and/or other physiological signals) to estimate the patient's brain state (e.g., predict or detect the onset of a seizure). Additionally, some systems of the present invention may be used to facilitate delivery of a therapy to the patient to prevent the onset of a predicted seizure and/or abort or mitigate a seizure after it has started. Facilitation of the delivery of the therapy may be carried out by outputting a warning or instructions to the patient or automatically delivering a therapy to the patient (e.g., pharmacological, electrical stimulation, etc.). The therapy may be delivered to the patient using the implanted devices that are used to collect the ambulatory signals, or it may be delivered to the patient through a different implanted device. A description of some systems that may be used to delivery a therapy to the patient are described in commonly owned U.S. Pat. Nos. 6,366,813 and 6,819,956, U.S. Patent Application Publication Nos. 2005/0021103 (published Jan. 27, 2005), 2005/0119703 (published Jun. 2, 2005), 2005/0021104 (published Jan. 27, 2005), 2005/0240242 (published Oct. 27, 2005), 2005/0222626 (published Oct. 6, 2005), and U.S. patent application Ser. Nos. 11/282,317 (filed Nov. 17, 2005), Ser. Nos. 11/321,897, 11/321,898, and 11/322,150 (all filed Dec. 28, 2005), the complete disclosures of which are incorporated herein by reference.

For patients suspected or known to have epilepsy, the systems of the present invention may be used to provide data and other metrics to the patients and physicians that heretofore have not been accurately measurable. For example, the data may be analyzed to (1) determine whether or not the patient has epilepsy, (2) determine the type of epilepsy, (3) determine the types of seizures, (4) localize or lateralize one or more seizure foci, (5) assess baseline seizure statistics and/or change from the baseline seizure statistics (e.g., seizure count, frequency, duration, seizure pattern, etc.) (6) monitor for sub-clinical seizures, assess a baseline frequency of occurrence, and/or change from the baseline occurrence, (7) measure the efficacy of AED treatments, (8) assess the effect of adjustments of the dosage of the AED, (9) determine the effects of adjustments of the type of AED, (10) determine the effect of, and the adjustment to parameters of, electrical stimulation (e.g., vagus nerve stimulation (VNS), deep brain stimulation (DBS), cortical stimulation, etc.), (11) determine "triggers" for the patient's seizures, (12) assess outcomes from surgical procedures, (13) provide immediate biofeedback to the patient, (14) screen patients for determining if they are an appropriate candidate for a seizure advisory system or other neurological monitoring or therapy system, or the like.

The systems of the present invention typically include one or more implantable devices that are in wireless communication with an external data collection device, typically with a high frequency communication link. The implantable devices of the present invention are typically implanted in a minimally invasive fashion beneath at least one layer of the scalp, above the patient's skull/calvarium, and over one or more target area of the patient's brain. As will be described in more detail below, the implantable devices are typically injected underneath the skin/scalp using an introducer, trocar or syringe-like device using local anesthesia. It is contemplated that such a procedure could be completed in 20 to 30 minutes by a physician or neurologist in an out-patient procedure.

The implantable devices are typically used to continuously sample the physiological signals for a desired time period so as to be able to monitor fluctuations of the physiological signal over substantially the entire time period. In alternative embodiments, however, the implantable devices may be used to periodically sample the patient's physiological signals or selectively/aperiodically monitor the patient's physiological signals.

The implantable devices may be permanently or temporarily implanted in the patient. If permanently implanted, the devices may be used for as long as the monitoring is desired, and once the monitoring is completed, because the implanted devices are biocompatible they may remain permanently implanted in the patient without any long term detrimental effects for the patient. However, if it is desired to remove the implanted devices, the devices may be explanted from the patient under local anesthesia. For ease of removal, it may be desirable to tether or otherwise attach a plurality of the implantable devices together (e.g., with a suture or leash) so that a minimal number of incisions are needed to explant the implantable devices.

Exact positioning of the implanted devices will usually depend on the desired type of monitoring. For patients who are being monitored for epilepsy diagnosis, the suspected type of epilepsy may affect the positioning of the implantable devices. For example, if the patient is thought to have temporal lobe epilepsy, a majority of the implantable devices will likely be located over the patient's temporal lobe. Additionally, if the focus of the seizure is known, it may be desirable to place a plurality of implantable devices directly over the focus. However, if the focus has not been localized, a plurality of implantable devices may be spaced over and around the target area of the patient's brain (and one or more implantable devices contralateral to the target area) in an attempt to locate or lateralize the seizure focus.

The number of implantable devices that are implanted in the patient will depend on the number of channels that the physician wants to concurrently monitor in the patient. Typically however, the physician will implant 32 or less, and preferably between about 2 and about 16 implantable devices, and most preferably between about 4 and about 8 implantable devices. Of course, in some instances, it may be desirable to implant more or less, and the present invention is not limited to the aforementioned number of implanted devices.

While the remaining discussion focuses on methods of using the systems and devices of the present invention for ambulatory monitoring of EEG signals of patients and patient populations for the diagnosis of epilepsy and/or evaluation of the efficacy and dosing of the patient's AEDs, it should be appreciated that the present invention is not limited to sampling EEG signals for epilepsy or for monitoring the efficacy of AEDs. For example, the implanted devices may be implanted under the skin of the patient's face, within the muscle of the patient's face, within the skull, above the jaw (e.g., sphenoidal implant that is placed under the skin just above the jaw to monitor the brain activity in the temporal lobes), or any other desired place on the patient's body. Furthermore, in addition to or as an alternative to monitoring EEG signals from the patient, it may be desired to monitor other physiological signals from a patient. For example, the system of the present invention may be used to monitor one or more of a blood pressure, blood oxygenation, temperature of the brain or other portion of the patient, blood flow measurements in the brain or other parts of the body, ECG/EKG, heart rate signals and/or change in heart rate signals, respiratory rate signals and/or change in respiratory rate signals, chemical concentrations of medications, pH in the blood or other portions of the body, other vital signs, other physiological or biochemical parameters of the patient's body, or the like.

Furthermore, the systems of the present invention may be useful for monitoring and assisting in the analysis of treatments for a variety of other neurological conditions, psychiatric conditions, episodic and non-episodic neurological phenomenon, or other non-neurological and non-psychiatric maladies. For example, the present invention may be useful for patients suffering from sleep apnea and other sleep disorders, migraine headaches, depression, Alzheimer's, Parkinson's Disease, eating disorders, dementia, attention deficit disorder, stroke, cardiac disease, diabetes, cancer, or the like. Likewise, the present invention may also be used to assess the symptoms, efficacy of pharmacological and electrical therapy on such disorders.

Referring now to the Figures, FIG. 1A illustrates a simplified system 10 embodied by the present invention. System 10 includes one or more implantable devices 12 that are configured to sample electrical activity from the patient's brain (e.g., EEG signals). The implantable devices may be active (with internal power source), passive (no internal power source), or semi-passive (internal power source to power components, but not to transmit data signal). The implantable devices 12 may be implanted anywhere in the patient, but typically one or more of the devices 12 may be implanted adjacent a previously identified epileptic focus or a portion of the brain where the focus is believed to be located. Alternatively, the devices 12 themselves may be used to help determine the location of the epileptic focus.

The physician may implant any desired number of devices in the patient. As noted above, in addition to monitoring brain signals, one or more additional implanted devices 12 may be implanted to measure other physiological signals from the patient.

While it may be possible to implant the implantable devices 12 under the skull and in or on the brain, it is preferred to implant the implantable devices 12 in a minimally invasive fashion under at least one layer of the patient's scalp and above the skull. Implantable devices 12 may be implanted between any of the layers of the scalp (sometimes referred to herein as "sub-galeal"). For example, the implantable devices may be positioned between the skin and the connective tissue, between the connective tissue and the epicranial aponeurosis/galea aponeurotica, between the epicranial aponeurosis/galea aponeurotica and the loose aerolar tissue, between the loose aerolar tissue and the pericranium, and/or between the pericranium and the calvarium. In some configurations, it may be useful to implant different implantable devices 12 between different layers of the scalp.

Implantable devices 12 will typically be configured to substantially continuously sample the brain activity of the groups of neurons in the immediate vicinity of the implanted device.

In some embodiments, if placed below the skull and in contact with the cortical surface of the brain, the electrodes may be sized to be able to sample activity of a single neuron in the immediate vicinity of the electrode (e.g., a microelectrode). Typically, the implantable device 12 will be interrogated and powered by a signal from the external device to facilitate the substantially continuous sampling of the brain activity signals. Sampling of the brain activity is typically carried out at a rate above about 200 Hz, and preferably between about 200 Hz and about 1000 Hz, and most preferably at about 400 Hz, but it could be higher or lower, depending on the specific condition being monitored, the patient, and other factors. Each sample of the patient's brain activity will typically contain between about 8 bits per sample and about 32 bits per sample, and preferably between about 12 bits per sample and about 16 bits per sample. Thus, if each return communication transmission to the external device includes one EEG sample per transmission, and the sample rate is 400 Hz and there are 16 bits/sample, the data transfer rate from the implantable devices 12 to the external device 14 is at least about 6.4 Kbits/second. If there are 32 implantable devices, the total data transfer rate for the system 10 would be about 205 Kbits/second. In alternative embodiments, it may be desirable to have the implantable devices sample the brain activity of the patient in a non-continuous basis. In such embodiments, the implantable devices 12 may be configured to sample the brain activity signals periodically (e.g., once every 10 seconds) or aperiodically.

Implantable device 12 may comprise a separate memory module for storing the recorded brain activity signals, a unique identification code for the device, algorithms, other programming, or the like.

A patient instrumented with the implanted devices 12 will typically carry a data collection device 14 that is external to the patient's body. The external device 14 would receive and store the signal from the implanted device 12 with the encoded EEG data (or other physiological signals). The external device is typically of a size so as to be portable and carried by the patient in a pocket or bag that is maintained in close proximity to the patient. In alternative embodiments, the device may be configured to be used in a hospital setting and placed alongside a patient's bed. Communication between the data collection device 14 and the implantable device 12 typically takes place through wireless communication. The wireless communication link between implantable device 12 and external device 14 may provide a communication link for transmitting data and/or power. External device 14 may include a control module 16 that communicates with the implanted device through an antenna 18. In the illustrated embodiment, antenna 18 is in the form of a necklace that is in communication range with the implantable devices 12. It should be appreciated however, that the configuration of antenna 18 and control module 16 may be in a variety of other conventional or proprietary forms. For example, in another embodiment control module 16 may be attached around an arm or belt of the patient, integrated into a hat, integrated into a chair or pillow, and/or the antenna may be integrated into control module 16.

In order to facilitate the transmission of power and data, the antenna of the external device and the implantable devices must be in communication range of each other. The frequency used for the wireless communication link has a direct bearing on the communication range. Typically, the communication range is between at least one foot, preferably between about one foot and about twenty feet, and more preferably between about six feet and sixteen feet. As can be appreciated, however, the present invention is not limited to such communication ranges, and larger or smaller communication ranges may be used. For example, if an inductive communication link is used, the communication range will be smaller than the aforementioned range.

In some situations, it may be desirable, to have a wire running from the patient-worn data collection device 14 to an interface (not shown) that could directly link up to the implanted devices 12 that are positioned below the patient's skin. For example, the interface may take the form of a magnetically attached transducer, as with cochlear implants. This could enable power to be continuously delivered to the implanted devices 12 and provide for higher rates of data transmission.

In some configurations, system 10 may include one or more intermediate transponder (not shown) that facilitates data transmission and power transmission between implantable device 12 and external device 14. The intermediate transponder may be implanted in the patient or it may be external to the patient. If implanted, the intermediate transponder will typically be implanted between the implantable device 12 and the expected position of the external device 14 (e.g., in the neck, chest, or head). If external, the transponder may be attached to the patient's skin, positioned on the patient's clothing or other body-worn assembly (e.g., eyeglasses, cellular phone, belt, hat, etc.) or in a device that is positioned adjacent the patient (e.g., a pillow, chair headrest, etc.). The intermediate transponder may be configured to only transmit power, only transmit data, or it may be configured to transmit both data and power. By having such intermediate transponders, the external device 14 may be placed outside of its normal communication range from the implanted devices 12 (e.g., on a patient's belt or in a patient's bag), and still be able to substantially continuously receive data from the implantable device 12 and/or transmit power to the implantable device 12.

Transmission of data and power between implantable device 12 and external device 14 is typically carried out through a radiofrequency link, but may also be carried out through magnetic induction, electromagnetic link, Bluetooth® link, Zigbee link, sonic link, optical link, other types of wireless links, or combinations thereof.

Figure 1B:
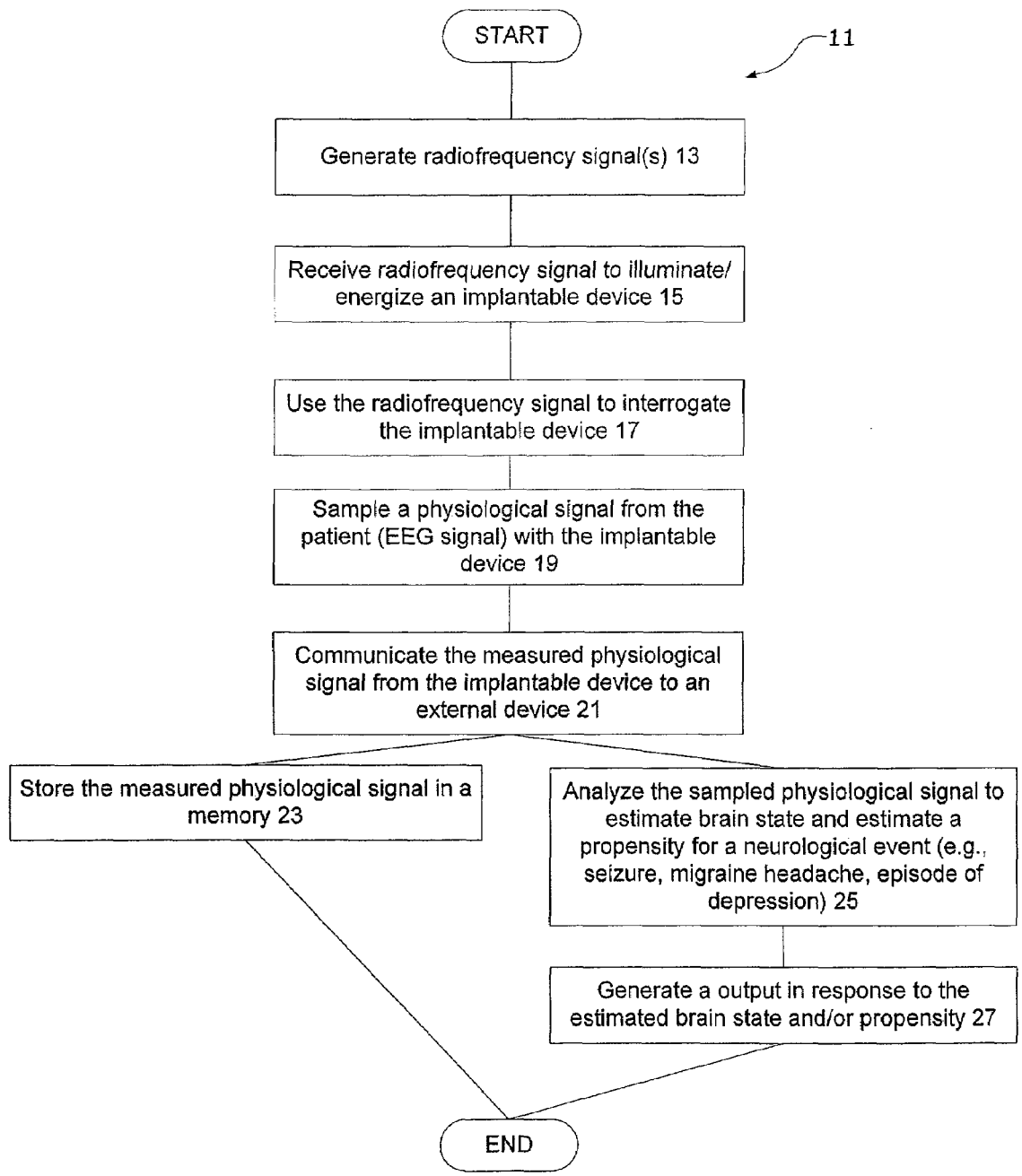
FIG. 1B illustrates simplified methods of operating the system of the present invention.

One preferred method 11 of wirelessly transmitting data and power is carried out with a radiofrequency link, similar to the link used with radiofrequency identification (RFID) tags. As illustrated in FIGS. 1A and 1B, in such embodiments, one or more radio frequency signals are emitted from the external device 14 through antenna 18 (step 13). If the external device 14 is in communication range of the implantable devices, at step 15 the radiofrequency (RF) energy signal illuminates the passive, implantable devices 12.

At step 17 the same RF signal interrogates the energized implantable device 12 to allow the implantable device to sample the desired physiological signal from the patient (such as an EEG signal). At step 19, the implantable device samples the instantaneous EEG signal (or other physiological signal) from the patient.

At step 21, the implantable device 12 then communicates a return RF signal to the external device 14 that is encoded with data that is indicative of the sampled EEG signal. Typically, the return RF signal is a based on the RF signal generated by the external device and includes detectable modifications which indicate the sampled EEG signal. For example, the return signal is typically a backscattering of the RF signal from the external device with the detectable modifications that indicate the sampled EEG signal. Advantageously, such backscattering does not require generation of a separate radiating signal and would not require an internal power source.

The return RF signals may also include the identification code of the implanted device so as to identify which device the data is coming from. At step 23, the return RF signal emitted by the internal device 12 is received by the antenna 18, and the RF signal is decoded to extract the sampled EEG signal. The sampled EEG signal may thereafter be stored in a memory of the external device 14. For embodiments in which the method is used to collect data, such data will be stored until accessed by the patient. Typically, such data will be analyzed on a separate device (e.g., physician's computer workstation).

In alternative embodiments, however, in which the external device may comprise software to analyze the data in substantially real-time, the received RF signal with the sampled EEG may be analyzed by the EEG analysis algorithms to estimate the patient's brain state which is typically indicative of the patient's propensity for a neurological event (step 25). The neurological event may be a seizure, migraine headache, episode of depression, tremor, or the like. The estimation of the patient's brain state may cause generation of an output (step 27). The output may be in the form of a control signal to activate a therapeutic device (e.g., implanted in the patient, such as a vagus nerve stimulator, deep brain or cortical stimulator, implanted drug pump, etc.). In other embodiments, the output may be used to activate a user interface on the external device to produce an output communication to the patient. For example, the external device may be used to provide a substantially continuous output or periodic output communication to the patient that indicates their brain state and/or propensity for the neurological event. Such a communication could allow the patient to manually initiate therapy (e.g., wave wand over implanted vagus nerve stimulator, cortical, or deep brain stimulator, take a fast acting AED, etc.) or to make themselves safe.

In preferred embodiments, the return RF signal is transmitted (e.g., backscattered) immediately after sampling of the EEG signal to allow for substantially real-time transfer (and analysis) of the patient's EEG signals. In alternate embodiments, however, the return RF signal may be buffered in an internal memory and the communication transmission to the external device 14 may be delayed by any desired time period and may include the buffered EEG signal and/or a real-time sampled EEG signal. The return RF signal may use the same frequency as the illumination RF signal or it may be a different frequency as the illumination RF signal.

Unlike conventional digital implantable devices that send large packets of stored data with each return RF communication transmission, some embodiment of the methods and devices of the present invention substantially continuously sample physiological signals from the patient and communicate in real-time small amounts of data during each return RF signal communication. Because only small amounts of data (one or a small number of sampled EEG signals from each implantable device 12) are transmitted during each communication, a lower amount of power is consumed and the illumination of the implanted device from the incoming high-frequency RF signal will be sufficient to power the implantable device 12 for a time that is sufficient to allow for sampling of the patient's EEG signal. Consequently, in most embodiments no internal power source, such as a battery, is needed in the implantable device 12—which further reduces the package size of the implantable device 12.

The implantable devices 12 and the external devices 14 of the present invention typically use an electromagnetic field/high frequency communication link to both illuminate the implantable device and enable the high data transfer rates of the present invention. Conventional devices typically have an internally powered implantable device and use a slower communication link (e.g., that is designed for long link access delays) and transmit data out on a non-continuous basis. In contrast, some embodiments of the present invention uses a fast access communication link that transmits a smaller bursts of data (e.g., single or small number of EEG sample at a time) on a substantially continuous basis.

The frequencies used to illuminate and transfer data between the implantable devices 12 and external device are typically between 13.56 MHz and 10 GHz, preferably between 402 MHz and 2.4 GHz, more preferably between 900 MHz and 2.4 GHz. While it is possible to use frequencies above 2.4 GHz, Applicants have found that it is preferred to use a frequency below 2.4 GHz in order to limit attenuation effects caused by tissue. As can be appreciated, while the aforementioned frequencies are the preferred frequencies, the present invention is not limited to such frequencies and other frequencies that are higher and lower may also be used. For example, it may be desirable us use the MICS (Medical Implant Communication Service band) that is between 402-405 MHz to facilitate the communication link. In Europe, it may be desirable to use ETSI RFID allocation 869.4-869.65 MHz.

While not illustrated in FIG. 1B, the system 10 of the present invention may also make use of conventional or proprietary forward error correction ("FEC") methods to control errors and ensure the integrity of the data transmitted from the implantable device 12 to the external device 14. Such forward error correction methods may include such conventional implementations such as cyclic redundancy check ("CRC"), checksums, or the like.

If desired, the data signals that are wirelessly transmitted from implantable device 12 may be encrypted prior to transmission to the control module 16. Alternatively, the data signals may be transmitted to the control module 16 as unencrypted data, and at some point prior to the storage of the data signals in the control module 16 or prior to transfer of the data signals to the physician's office, the EEG data may be encrypted so as to help ensure the privacy of the patient data.

FIGS. 3A and 3B illustrate two embodiments of the externally powered leadless, implantable device 12 that may be used with the system 10 of the present invention. The implantable devices 12 of the present invention are preferably passive or semi-passive and are "slaves" to the "master" external device 14. The implantable devices will typically remain dormant until they are interrogated and possibly energized by an appropriate RF signal from the external device 14. As will be described below, the implantable device 14 may have minimal electronic components and computing power, so as to enable a small package size for the implantable device.

Advantageously, the embodiment illustrated in FIGS. 3A and 3B are minimally invasive and may be implanted with an introducer, trocar or syringe-like device under local anesthesia by a physician or potentially even a physician's assistant. Typically, the implanted device of FIG. 3A may have a longitudinal dimension 20 of less than about 3 cm, and preferably between about 1 cm and about 10 cm, and a lateral dimension 22 of less than about 2 mm, and preferably between about 0.5 mm and about 10 mm. As can be appreciated, such dimensions are merely illustrative, and other embodiments of implanted device may have larger or smaller dimensions.

FIG. 3A illustrates an embodiment that comprises a first electrode 24 and a second electrode 26 that are disposed on opposing ends of housing 28. The first and second electrodes 24, 26 may be composed of platinum, platinum-iridium alloy, stainless steel, or any other conventional material. The electrodes may include a coating or surface treatment such as platinum-iridium or platinum-black in order to reduce electrical impedance. The first and second electrodes 24, 26 will typically have a smooth or rounded shape in order to reduce tissue erosion and may have a surface area of about 3 mm$^2$, but other embodiments may be smaller or larger. Since electrodes 24, 26 are typically adapted to only sense physiological signals and are not used to deliver stimulation, the surface area of the electrodes may be smaller than conventional implantable devices. The smaller electrodes have the advantage of reducing the overall device size which can be beneficial for improving patient comfort and reducing the risk of tissue erosion.

Housing 28 is typically in the form of a radially symmetrical, substantially cylindrical body that hermetically seals electronic components 30 disposed within a cavity 32. Housing 28 may be composed of a biocompatible material, such as glass, ceramic, liquid crystal polymer, or other materials that are inert and biocompatible to the human body and able to hermetically seal electronic components. Housing 28 may have embedded within or disposed thereon one or more x-ray visible markers 33 that allow for x-ray localization of the implantable device. Alternatively, one or more x-ray visible markers may be disposed within the cavity 32. Cavity 32 may be filled with an inert gas or liquid, such as an inert helium nitrogen mixture which may also be used to facilitate package leakage testing. Alternatively, it may be desirable to fill the cavity 32 with a liquid encapsulant (not shown) that hardens around the electronic components. The liquid encapsulant may comprise silicone, urethane, or other similar materials.

While housing 28 is illustrated as a substantially cylindrical body with the electrodes 24, 26 on opposing ends, housing may take any desired shape and the electrodes may be positioned at any position/orientation on the housing 28. For example, housing 28 may taper in one direction, be substantially spherical, substantially oval, substantially flat, or the like. Additionally or alternatively, the body may have one or more substantially planar surfaces so as to enhance the conformity to the patient's skull and to prevent rotation of the implantable device 12. While not shown, housing 28 may optionally include a conductive electromagnetic interference shield (EMI) that is configured to shield the electronic components 30 in housing 28. The EMI shield may be disposed on an inner surface of the housing, outer surface of the housing, or impregnated within the housing.

If desired, housing 28 may optionally comprise an anchoring assembly (not shown) that improves the anchoring of the implantable device 12 to the skull or the layers within the scalp. Such anchoring may be carried out with adhesive, spikes, barbs, protuberances, suture holes, sutures, screws or the like.

In the illustrated embodiment, first electrode 24 is disposed on a first end of housing 28 and is in electrical communication with the electronic components 30 through a hermetic feedthrough 34. Feedthrough 34 may be the same material as the first electrode 24 or it may be composed of a material that has a similar coefficient of thermal expansion as the housing 28 and/or the first electrode 24. Feedthrough 34 may make direct contact with a pad (not shown) on a printed circuit board 36, or any other type of conventional connection may be used (e.g., solder ball, bond wire, wire lead, or the like) to make an electrical connection to the printed circuit board 36.

Second electrode 26 may be spaced from a second, opposing end of the housing 28 via an elongated coil member 38. In the illustrated embodiment, the second electrode 26 typically comprises a protuberance 39 that is disposed within and attached to a distal end of the coil member 38. Coil member 38 acts as an electrical connection between second electrode and the electronic components 30 disposed within housing 28.

Coil member 38 will typically be composed of stainless steel, a high strength alloy such as MP35N, or a combination of materials such as a MP35N outer layer with silver core.

The illustrated embodiment shows that coil member 38 has a largest lateral dimension (e.g., diameter) that is less than the largest lateral dimension (e.g., diameter) of housing 28, but in other embodiments, the coil may have the same lateral dimension or larger lateral dimension from housing 28.

Coil member 38 may also be used as an antenna to facilitate the wireless transmission of power and data between the implantable device 12 and the external device 14 (or other device). In preferred embodiments, coil member 38 may be used to receive and transmit radiofrequency signals. In alternative embodiments, however, coil member 38 may be inductively coupled to an external coil to receive energy from a modulating, alternating magnetic field. Unlike other conventional implantable devices, the RF antenna is disposed outside of the housing 28 and extends from one end of housing 28. It should be appreciated however, that the present invention is not limited to a substantially cylindrical antenna extending from an end of the housing 28 and various other configurations are possible. For example, it may be desirable to wind the antenna around or within the housing 28. Furthermore, it may be desirable to use a substantially flat antenna (similar to RFID tags) to facilitate the transmission of power and data. To facilitate implantation, such antennas may be rolled into a cylindrical shape and biased to take the flat shape upon release from the introducer.

While not shown, it may also be desirable to provide a second antenna between the first electrode 24 and the housing 28. The second antenna may be used for power and downlink using a first frequency, e.g., 13.56 MHz, while the first antenna may be used for uplink using a second frequency, e.g., 902-928 MHz. In such embodiments, however, the implantable devices would need to have an internal timebase (e.g., oscillator and a frequency synthesizer). For the embodiments that use only a single frequency for the downlink and uplink, an internal timebase or frequency synthesizer is not needed—and the timebase established by the master (e.g., external device 14) can be used.

Coil member 38 may be in electrical communication with the electronic components 30 with a hermetic feedthrough 42 that extends through a via 44 in housing 28. Feedthrough 42 is typically composed of a material that has a coefficient of thermal expansion that is substantially similar to the material of housing 40. Because the coil member 38 is outside of the housing 28 the length of the implantable device 12 will be increased, but the flexible coil will be better exposed to the RF signals and will be allowed to conform to the shape of the patient's skull.

Coil member 38 is typically disposed outside of the housing 28 and disposed within an elongate, substantially flexible housing 40. Compared to the more rigid housing 28, the flexible housing 40 is better able to conform to the shape of an outer surface of the patient's skull, more comfortable for the patient and reduces the chance of tissue erosion. Flexible housing 40 may comprise silicone, polyurethane, or the like In the illustrated embodiment, flexible housing 40 extends along the entire length of coil member 38, but in other embodiments, flexible housing 40 may extend less than or longer than the longitudinal length of coil member 38. Flexible housing 40 will typically have a substantially cylindrical shape, but if desired a proximal end 46 of the cylindrical housing may be enlarged or otherwise shaped to substantially conform to a shape of the housing 28. The shaped proximal end 46 may be adhered or otherwise attached to the end of the housing 40 to improve the hermetic seal of the housing and may reduce any potential sharp edge or transition between the housings 28, 40. While FIG. 3A only illustrates a single layered flexible housing, if desired, the flexible housing 40 may comprise a plurality of layers, and the different layers may comprise different types of materials, have embedded x-ray markers, or the like.

A longitudinal length of flexible housing 40 and the longitudinal length of the rigid housing 28 may vary depending on the specific embodiment, but a ratio of the longitudinal length of the flexible housing 40: the longitudinal length of the more rigid housing 28 is typically between about 0.5:1 and about 3:1, and preferably between about 1:1 and about 2:1. By having the longitudinal length of the flexible housing longer than the longitudinal length of the rigid housing, advantageously the implantable device will be more comfortable and better able to conform to the outer surface of the patient's skull. In alternative embodiments, it may also be desirable to have a longitudinal length of the rigid housing 28 be longer than the longitudinal length of the flexible housing 40, or in any other desired configuration.

Because the implantable devices 12 of the present invention consume a minimal amount of energy and use a high frequency RF coupling to power the device and communicate the EEG signals to the external device, unlike other conventional devices, some of the implantable devices 12 of the present invention will not need a ferrite core to store energy, and the electronic components 30 of the present invention will typically include aluminum or other MRI-safe material. Consequently, the patient's implanted with the implantable device 12 may safely undergo MRI imaging.

FIG. 3B illustrates another embodiment of implantable device 12 that is encompassed by the present invention. The embodiment of FIG. 3B shares many of the same components as the embodiment of FIG. 3A, and such components are noted with the same reference numbers as FIG. 3A. There are, however, a few notable exceptions. Specifically, instead of having a hermetically sealed housing, the embodiment of FIG. 3B provides a conductive body 48 that acts as both the housing for the electronic components 30 and as the second electrode. Conductive body 48 may be composed of a metallized polymer, one or more metal or metal alloys, or other conductive material. Because body 48 is conductive, it may act as an electromagnetic interference (EMI) shield to the electronic components disposed within the cavity 32. Electrical connections to the printed circuit board 36 may be carried out with one or more conductive spring conductors 50 or other conventional lead connectors.

Feedthrough 42 that is connected to the coil member 38 extends from the end of coil member 38 and makes an electrical connection with a lead on the printed circuit board 36. The feedthrough 42 works in conjunction with one or more dielectric seals or spacers 52 to hermetically seal the cavity 32. Similar to above, the cavity 32 may be filled with an inert gas or an encapsulant. The proximal end 46 of flexible body 40 may be coupled to the seals 52 and/or coupled to the conductive body 48.

As shown in the embodiment of FIG. 3B, the surface area of conductive body 48 (e.g., the first electrode) may be larger than the surface area of the second electrode 26. In other embodiments, however, the surface area of the second electrode 26 may have the substantially same surface area and/or shape as the conductive body 48.

In most embodiments, the implantable devices shown in FIGS. 3A and 3B function completely independent of the other implantable devices 12 and there is no physical connection or communication between the various devices. If desired, however, the implantable devices 12 may be physically coupled to each other with a connecting wire or tether and/or in communication with each other. If the plurality of implanted devices 12 are in communication with one another, it may be desired to use a communication frequency between the implanted devices 12 that is different from the frequency to communicate between the implanted devices and the external device 14. Of course, the communication frequency between the implanted devices 12 may also be the same frequency as the communication frequency with the external device 14.

Figure 3C:
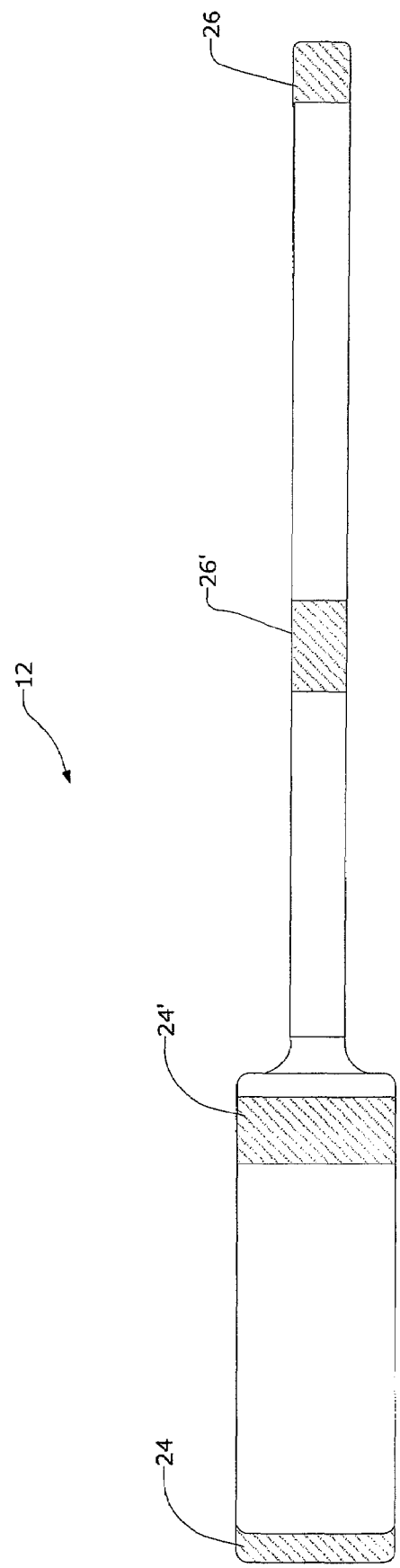
FIG. 3C illustrates a simplified plan view of an embodiment that comprises four electrodes disposed on the implanted device.

While FIGS. 3A and 3B illustrate a first and second electrode 24, 26, the implantable devices 12 of the present invention are not limited to only two electrodes. Any number of electrodes may be coupled to the implantable device in any orientation. For example, the electrodes do not have to extend from ends of the housing, but may be positioned anywhere along a portion of the housings 28, 40. Furthermore, a plurality of electrodes and their leads may be disposed along the length of the flexible housing 40 and/or rigid housing 28 so as to provide more than two electrodes per implantable device. For example, FIG. 3C illustrates a simplified embodiment in which there are two additional electrode 24', 26' positioned on the rigid housing 28 and flexible housing 40, respectively. The spacing between the various contacts 24, 24', 26, 26' may vary or be the same distance between each other. The spacing between electrodes will likely depend on the overall length of the implantable device, but will typically be between about 2 mm and about 20 mm and preferably be between about 5 mm and about 10 mm. In addition to the embodiment shown in FIG. 3C, it may be desirable to have the additional electrodes only on the flexible housing 40 or only on the rigid housing 28. While only four electrodes are shown on the implanted device, it should be appreciated that any desirable number of electrodes (e.g., anywhere between two electrodes and about sixteen electrodes) may coupled to the implanted device.

While FIGS. 3A-3B illustrate some currently preferred embodiments of the implantable device 12, the present invention further encompasses other types of minimally invasive implantable devices 12 that can monitor the brain activity and other physiological signals from the patient. For example, a plurality of electrodes might reside on a single lead that could be tunneled under the scalp from a single point of entry. Examples of such embodiments are shown in FIGS. 2A-2E.

Such implantable devices 12 include an active electrode contact 400 that is in communication with one or more passive electrode contacts 401. The active electrode contact 400 may be used to facilitate monitoring of the physiological signals using the array of active and passive electrode contacts. The arrays of electrode contacts may be arranged in a linear orientation (FIG. 2C) or in a grid pattern (FIG. 2E), or any other desired pattern (e.g., circular, star pattern, customized asymmetric pattern, etc.) For example, if the implantable device comprises two electrode contacts (e.g., one active contact and one passive contact), such an embodiment would have a similar configuration as the embodiment of FIG. 3A. Similarly, if the implantable device were to have four substantially linearly positioned electrode contacts (e.g., one active contact and three passive contacts), such an embodiment would be substantially similar to the configuration shown in FIG. 3C.

Figure 2A:
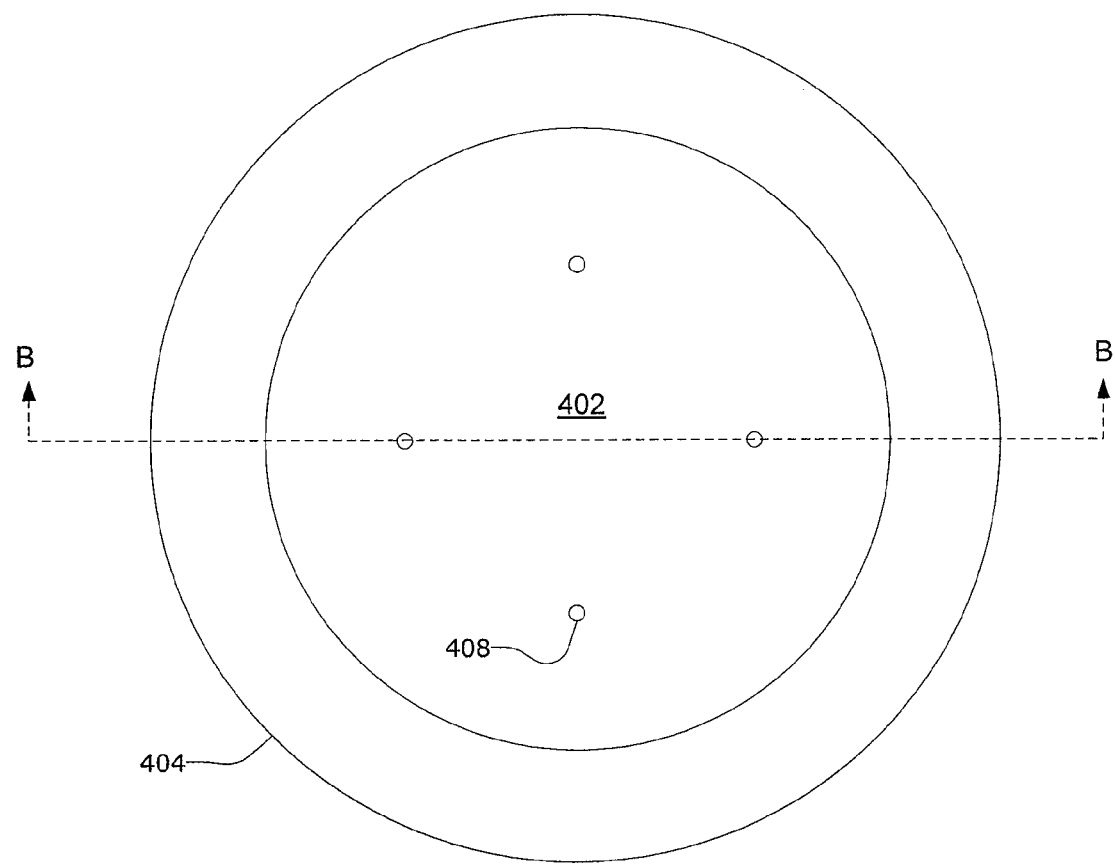
FIG. 2A illustrates a bottom view of one embodiment of an active implantable device that is encompassed by the present invention.

FIG. 2A illustrates a bottom view of an active electrode contact 400 that may be part of the implantable device 12 of the present invention. The active electrode contact comprises a base 402 that is coupled to a contact portion 404. The base 402 and contact portion may be composed of any number of different types of materials, such as platinum, platinum-iridium alloy, stainless steel, or any other conventional material. In preferred embodiments, both the base 402 and contact portion 404 are formed to their desired shape. The base 402 may comprise a plurality of hermetic feedthroughs 413 that is implemented using conventional glass metal seal technology (e.g., pins 408, glass seal 414, and vias 406). The hermetic feedthroughs 413 may be used to connect to an antenna (not shown) for communication with the external device 14 or to make an electrical connection with an adjacent passive electrode contact 401 in the implanted device 12. In the illustrated embodiment, base 402 comprises four hermetic feedthroughs 413. But as can be appreciated the base 402 may comprise any desired number of feedthroughs 413 (e.g., anywhere between two and sixty four feedthroughs).

Figure 2B:
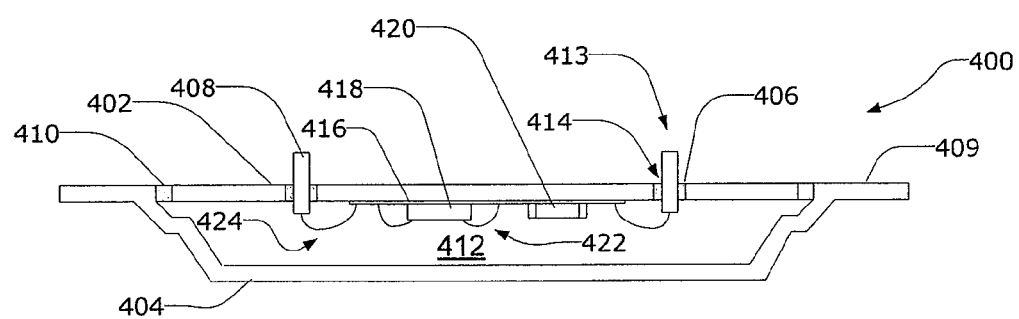
FIG. 2B illustrates a cross-sectional view of the active implantable device of FIG. 2A along lines B-B.

FIG. 2B illustrates a cross-sectional view of the active electrode contact 400 along lines B-B in FIG. 2A. As shown in FIG. 2B, the contact portion 404 is shaped to as to align the base 402 along a bottom surface defined by flanges 409. Base 402 may be coupled to the contact portion 404 with a laser weld, glass metal seal, or other conventional connector 410 along an outer perimeter of the base 402 to hermetically seal components of the active electrode contact within a cavity 412 defined by the base 402 and contact portion 404. If desired, the cavity 412 may be backfilled with nitrogen and/or helium to facilitate package leak testing.

A thin or thick filmed microcircuit or a printed circuit board ("PCB") 416 may be mounted onto an inner surface of the base 402. PCB 416 may have active components 418 (e.g., integrated circuits, ASIC, memory, etc.) and passive components 420 (e.g., resistors, capacitors, etc.) mounted thereto. Leads or bond wires 422 from the active and passive components may be electrically attached to pads on the PCB (not shown) which make electrical connections to leads or bond wires 424 that are attached to the hermetic feedthroughs 413. While not shown in FIG. 2B, the active electrode contact 400 may comprise a rechargeable or non-rechargeable power supply (e.g., batteries), and/or x-ray visible markers (not shown).

Figure 2C:
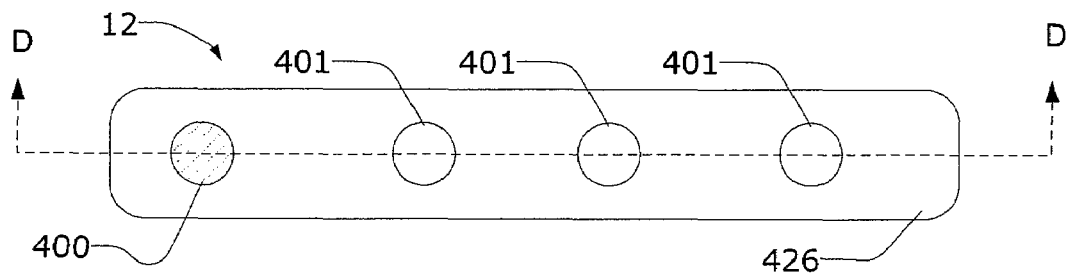
FIG. 2C is a linear implantable device that comprises a plurality of electrode contacts in which at least one electrode contact comprises the active implantable device of FIG. 2A.
Figure 2D:
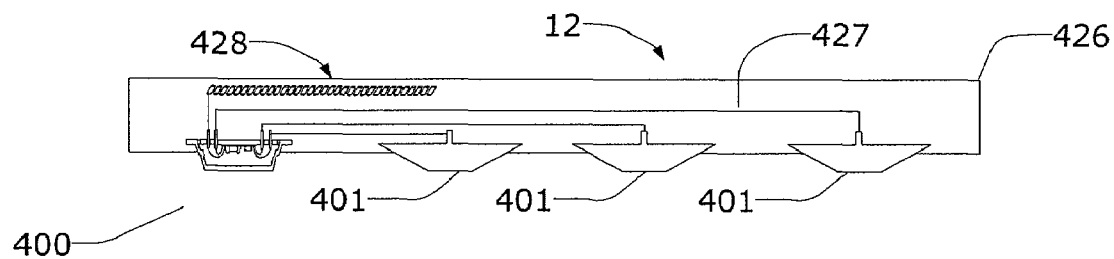
FIG. 2D is a cross sectional view of the implantable device of FIG. 2C along lines D-D.

As noted above, the active contacts may be used in conjunction with one or more passive contacts to form an active implantable device 12 to facilitate monitoring of the patient's physiological signals and to communicate with the external device 14. FIGS. 2C and 2D illustrate an embodiment of the implantable device 12 in which one active contact 400 is housed in a body 426 along with a plurality of passive contacts 401 to form a multiple contact implantable device 12. The contact portion of the active contact 400 is exposed through an opening in the body 426 to allow for sampling of the physiological signals (e.g., EEG) from the patient. The body 426 may be substantially flexible or rigid and may have similar dimensions and/or shapes as the embodiments shown in FIGS. 3A-3C. Body 426 may be composed of a biocompatible material such as silicone, polyurethane, or other materials that are inert and biocompatible to the human body. Body 426 may also be composed of a rigid material such as polycarbonate. The implantable device may be injected into the patient using the introducer assembly shown in FIG. 6 and methods shown in FIG. 7.

As shown in FIG. 2D wire leads 427 may extend from the passive contacts 401 and be electrically and physically coupled to one of the hermetic feedthroughs 413 of the active contact 400 to facilitate sampling of the physiological signals using all four electrode contacts. For embodiments which use a wireless link (e.g., RF) to wirelessly transmit data to the external device 14 and optionally to power the device, one of the feedthroughs may be coupled to an antenna 428 that is configured to wirelessly communicate with the external device. It should be appreciated, that while not described herein, the embodiments of FIGS. 2C-2E may have any of the components or variations as described above in relation to FIGS. 3A-3B.

Figure 2E:
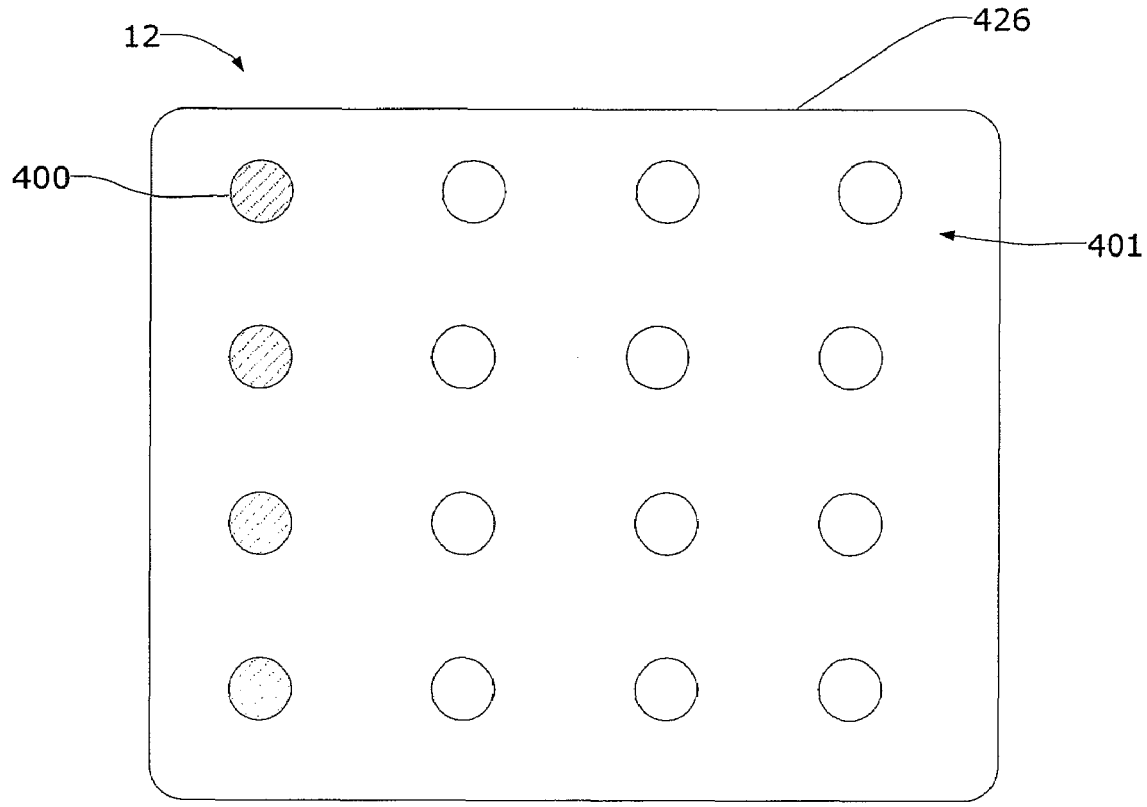
FIG. 2E is a 4×4 electrode array that comprises a plurality of electrode contacts in which at least one electrode contact comprises the active implantable contact of FIG. 2A.

FIG. 2E illustrates an alternative embodiment of the implantable device 12 in which the implantable device 12 is in the form of a 4×4 grid array of active and passive contacts. At least one of the electrode contacts may be an active contact 400 so as to facilitate monitoring of the patient's physiological signals with the array. In the illustrated embodiment, the contacts in the leftmost column (highlighted with cross-hatching) are active electrode contacts 400, and the contacts in remaining column are electrically connected to one of the active contacts 400. Of course, any number of active contacts 400 and passive contacts 401 may be in the grid array and the active contact(s) 400 may be positioned anywhere desired. For example, if the active electrode contact 400 has sixteen or more hermetic feedthroughs, only one of the contacts in the array needs to be active and the remaining fifteen contacts could be passive contacts.

Figure 4:
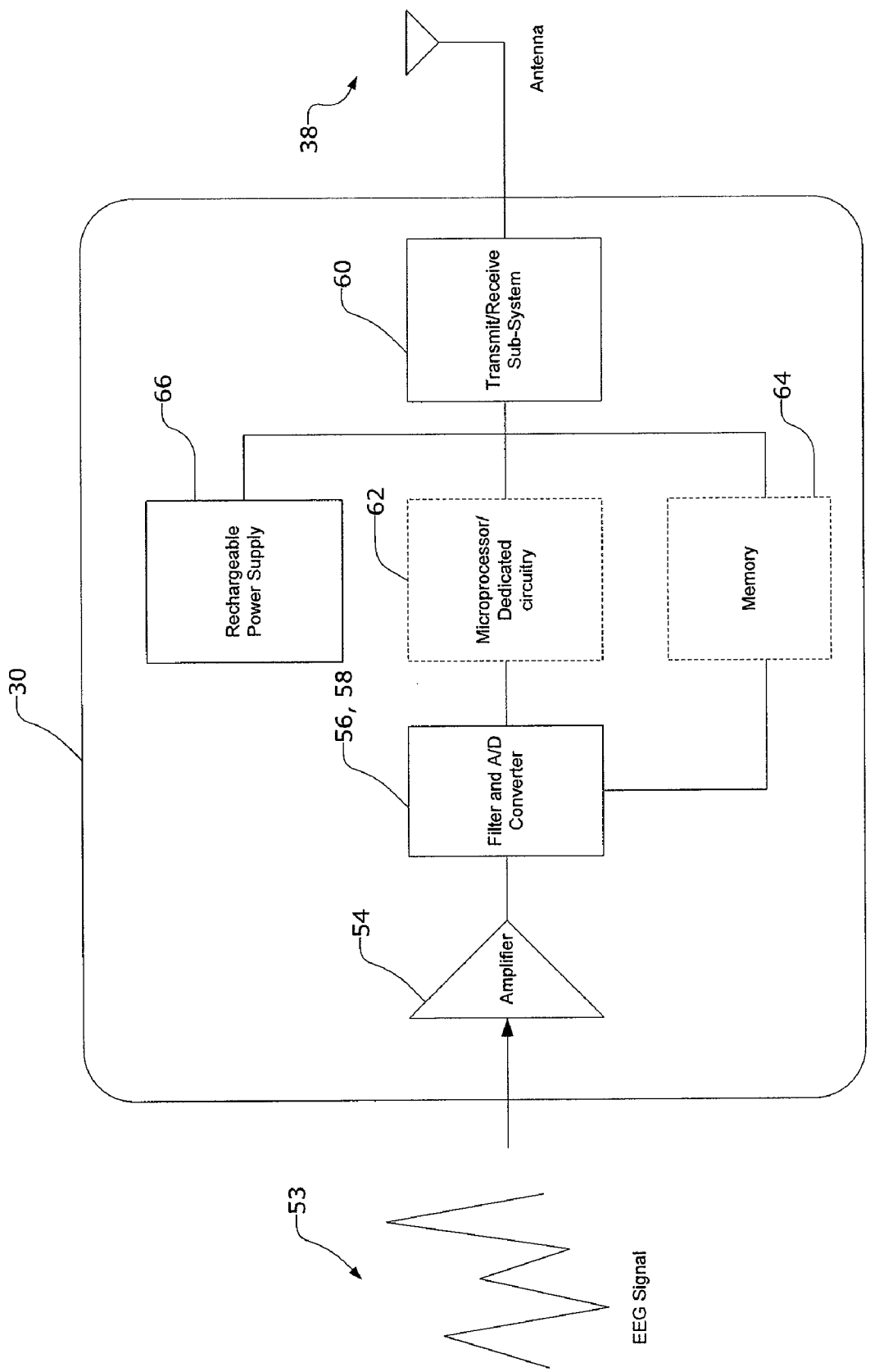
FIG. 4 illustrates one embodiment of the electronic components that may be disposed within the implantable device.

FIG. 4 illustrates one simplified embodiment of the electronic components 30 (e.g., active components 418 and passive components 420 in FIG. 2B) that may be disposed in the implantable devices 12 as shown in FIGS. 2A-3C. It should be appreciated, however, that the electronic components 30 of the implantable device 12 may include any combination of conventional hardware, software and/or firmware to carry out the functionality described herein. For example, the electronic components 30 may include many of the components that are used in passive RF integrated circuits.

The first and second electrodes will be used to sample a physiological signal from the patient—typically an EEG signal 53, and transmit the sampled signal to the electronic components 30. While it may be possible to record and transmit the analog EEG signal to the external device, the analog EEG signal will typically undergo processing before transmission to the external device 14. The electronic components typically include a printed circuit board that has, among others, an amplifier 54, one or more filters 56 (e.g., bandpass, notch, lowpass, and/or highpass) and an analog-to-digital converter 58. In some embodiments, the processed EEG signals may be sent to a transmit/receive sub-system 60 for wireless transmission to the external device via an antenna (e.g., coil member 38). Additional electronic components that might be useful in implantable device 12 may be found in U.S. Pat. Nos. 5,193,539, 5,193,540, 5,312,439, 5,324,316, 5,405,367 and 6,051,017.

In some alternative embodiments of the present invention, the electronic components 30 may include a memory 64 (e.g., RAM, EEPROM, Flash, etc.) for permanently or temporarily storing or buffering the processed EEG signal. For example, memory 64 may be used as a buffer to temporarily store the processed EEG signal if there are problems with transmitting the data to the external device. For example, if the external device's power supply is low, the memory in the external device is removed, or if the external device is out of communication range with the implantable device, the EEG signals may be temporarily buffered in memory 64 and the buffered EEG signals and the current sampled EEG signals may be transmitted to the external device when the problem has been corrected. If there are problems with the transmission of the data from the implantable device, the external device may be configured to provide a warning or other output signal to the patient to inform them to correct the problem. Upon correction of the problems, the implantable device may automatically continue the transfer the temporarily buffered data and the real-time EEG data to the memory in the external device.

The electronic components 30 may optionally comprise dedicated circuitry and/or a microprocessor 62 (referred to herein collectively as "microprocessor") for further processing of the EEG signals prior to transmission to the external device. The microprocessor 62 may execute EEG analysis software, such as a seizure prediction algorithm, a seizure detection algorithm, safety algorithm, or portions of such algorithms, or portions thereof. For example, in some configurations, the microprocessor may run one or more feature extractors that extract features from the EEG signal that are relevant to the purpose of monitoring. Thus, if the system is being used for diagnosing or monitoring epileptic patients, the extracted features (either alone or in combination with other features) may be indicative or predictive of a seizure. Once the feature(s) are extracted, the microprocessor 62 may send the extracted feature(s) to the transmit/receive sub-system 60 for the wireless transmission to the external device and/or store the extracted feature(s) in memory 64. Because the transmission of the extracted features is likely to include less data than the EEG signal itself, such a configuration will likely reduce the bandwidth requirements for the communication link between the implantable device and the external device. Since the extracted features do not add a large amount of data to the data signal, in some embodiments, it may also be desirable to concurrently transmit both the extracted feature and the EEG signal. A detailed discussion of various embodiments of the internal/external placement of such algorithms are described in commonly owned U.S. patent application Ser. No. 11/322,150, filed Dec. 28, 2005 to Bland et al., the complete disclosure of which is incorporated herein by reference.

While most embodiments of the implantable device 12 are passive and does not need an internal power source or internal clock, in some embodiments, the electronic components 30 may include a rechargeable or non-rechargeable power supply 66 and an internal clock (not shown). The rechargeable or non-rechargeable power supply may be a battery, a capacitor, or the like. The rechargeable power supply 66 may also be in communication with the transmit/receive sub-system 60 so as to receive power from outside the body by inductive coupling, radiofrequency (RF) coupling, etc. Power supply 66 will generally be used to provide power to the other components of the implantable device. In such embodiments, the implanted device may generate and transmit its own signal with the sampled EEG signal for transmission back to the external device. Consequently, as used herein "transmit" includes both passive transmission of a signal back to the external device (e.g., backscattering of the RF signal) and internal generation of a separate signal for transmission back to the external device.

Figure 5:
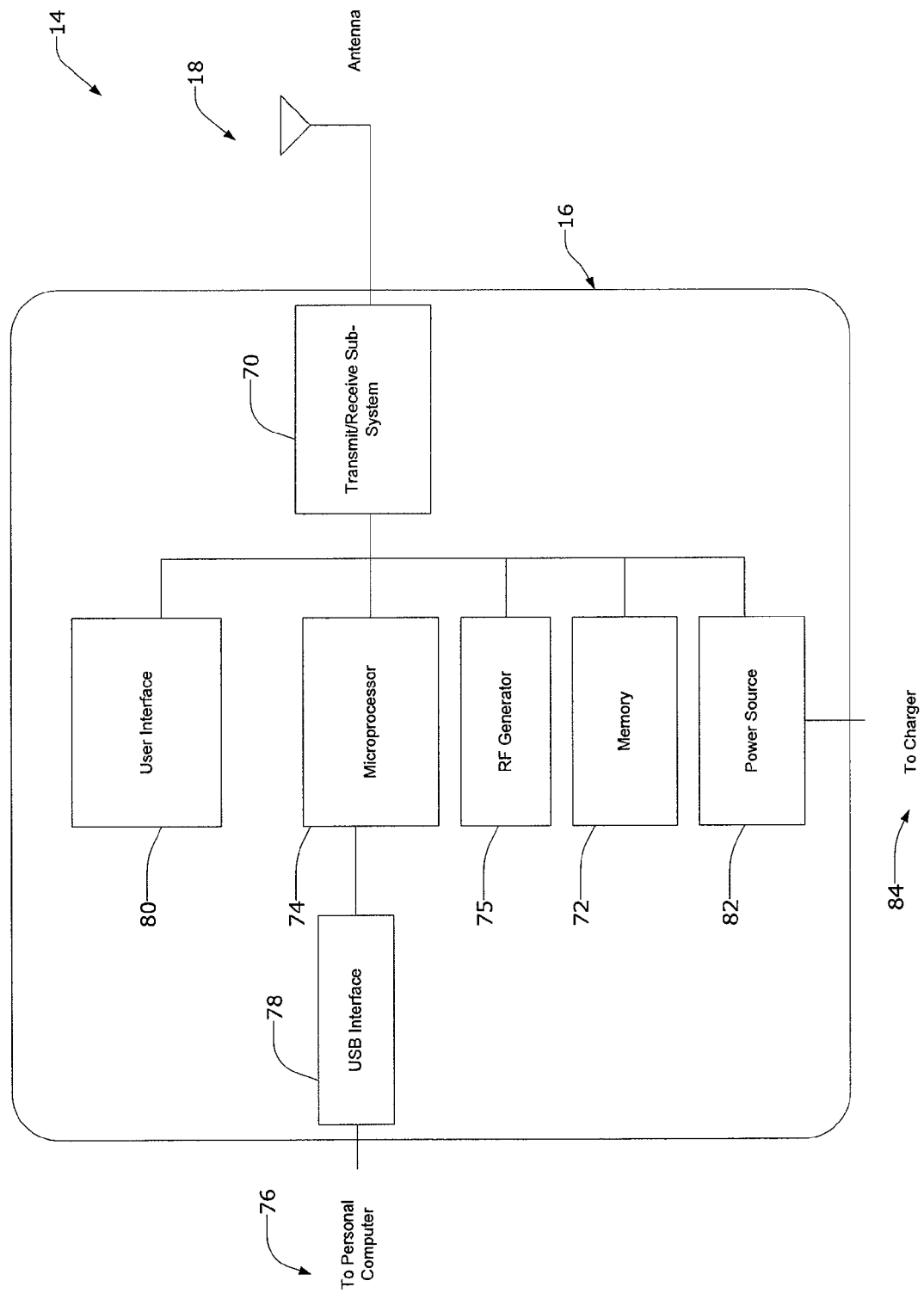
FIG. 5 is a block diagram illustrating one embodiment of electronic components that may be in the external device.

FIG. 5 is a simplified illustration of some of the components that may be included in external device 14. Antenna 18 and a transmit/receive subsystem 70 will receive a data signal that is encoded with the EEG data (or other physiological data) from the antenna 38 of the implantable device 12 (FIG. 4). As used herein, "EEG data" may include a raw EEG signal, a processed EEG signal, extracted features from the EEG signal, an answer from an implanted EEG analysis software (e.g., safety, prediction and/or detection algorithm), or any combination thereof.

The EEG data may thereafter be stored in memory 72, such as a hard drive, RAM, permanent or removable Flash Memory, or the like and/or processed by a microprocessor 74 or other dedicated circuitry. Microprocessor 74 may be configured to request that the implantable device perform an impedance check between the first and second electrodes and/or other calibrations prior to EEG recording and/or during predetermined times during the recording period to ensure the proper function of the system.

The EEG data may be transmitted from memory 72 to microprocessor 74 where the data may optionally undergo additional processing. For example, if the EEG data is encrypted, it may be decrypted. The microprocessor 74 may also comprise one or more filters that filter out high-frequency artifacts (e.g., muscle movement artifacts, eye-blink artifacts, chewing, etc.) so as to prevent contamination of the high frequency components of the sampled EEG signals. In some embodiments, the microprocessor may process the EEG data to measure the patient's brain state, detect seizures, predict the onset of a future seizure, generate metrics/measurements of seizure activity, or the like. A more complete description of seizure detection algorithms, seizure prediction algorithms, and related components that may be implemented in the external device 14 may be found in pending, commonly owned U.S. patent application Ser. Nos. 11/321,897 and 11/321,898, filed on Dec. 28, 2005, to Leyde et al. and DiLorenzo et al., and 60/897,551, filed on Jan. 25, 2007, to Leyde et al., the complete disclosures of which are incorporated herein by reference.

It should be appreciated, however, that in some embodiments some or all of the computing power of the system of the present invention may be performed in a computer system or workstation 76 that is separate from the system 10, and the external device 14 may simply be used as a data collection device. In such embodiments, the personal computer 76 may be located at the physician's office or at the patient's home and the EEG data stored in memory 72 may be uploaded to the personal computer 76 via a USB interface 78, removal of the memory (e.g., Flash Memory stick), or other conventional communication protocols, and minimal processing may be performed in the external device 14. In such embodiments, the personal computer 76 may contain the filters, decryption algorithm, EEG analysis software, such as a prediction algorithm and/or detection algorithm, report generation software, or the like. Some embodiments of the present invention may take advantage of a web-based data monitoring/data transfer system, such as those described in U.S. Pat. Nos. 6,471,645 and 6,824,512, the complete disclosures of which are incorporated herein by reference.

External device 14 may also comprise an RF signal generator 75 that is configured to generate the RF field for interrogating and optionally powering the implanted devices 12. RF generator 75 will be under control of the microprocessor 74 and generate the appropriate RF field to facilitate monitoring and transmission of the sampled EEG signals to the external device.

External device 14 will typically include a user interface 80 for displaying outputs to the patient and for receiving inputs from the patient. The user interface typically comprise outputs such as auditory devices (e.g., speakers) visual devices (e.g., LCD display, LEDs to indicate brain state or propensity to seizure), tactile devices (e.g., vibratory mechanisms), or the like, and inputs, such as a plurality of buttons, a touch screen, and/or a scroll wheel.

The user interface may be adapted to allow the patient to indicate and record certain events. For example, the patient may indicate that medication has been taken, the dosage, the type of medication, meal intake, sleep, drowsiness, occurrence of an aura, occurrence of a seizure, or the like. Such inputs may be used in conjunction with the recorded EEG data to improve the analysis of the patient's condition and determine the efficacy of the medications taken by the patient.

The LCD display of the user interface 80 may be used to output a variety of different communications to the patient including, status of the device (e.g., memory capacity remaining), battery state of one or more components of system, whether or not the external device 14 is within communication range of the implantable devices 12, brain state indicators (e.g., a warning (e.g., seizure warning), a prediction (e.g., seizure prediction), unknown brain state, safety indication, a recommendation (e.g., "take drugs"), or the like). Of course, it may be desirable to provide an audio output or vibratory output to the patient in addition to or as an alternative to the visual display on the LCD. In other embodiments, the brain state indicators may be separate from the LCD display to as to provide a clear separation between the device status outputs and the brain state indicators. In such embodiments, the external device may comprise different colored LEDs to indicate different brain states. For example, a green LED may indicate a safe brain state, a yellow light may indicate an unknown brain state, and a red light may indicate either a seizure detection or seizure prediction.

External device may also include a medical grade power source 82 or other conventional power supply that is in communication with at least one other component of external device 14. The power source 82 may be rechargeable. If the power source 80 is rechargeable, the power source may optionally have an interface for communication with a charger 84. While not shown in FIG. 5, external device 14 will typically comprise a clock circuit (e.g., oscillator and frequency synthesizer) to provide the time base for synchronizing external device 14 and the internal device(s) 12. In preferred embodiments, the internal device(s) 12 are slaves to the external device and the implantable devices 12 will not have to have an individual oscillator and a frequency synthesizer, and the implantable device(s) 12 will use the "master" clock as its time base. Consequently, it may be possible to further reduce the size of the implantable devices.

In use, one or more of the implantable devices are implanted in the patient. The implanted device is interrogated and powered so that the EEG signals are sampled from the patient's brain. The EEG signals are processed by the implanted device and the processed EEG signals are wirelessly transmitted from the implanted device(s) to an external device. The EEG signals are stored for future or substantially real-time analysis.

Figure 6:
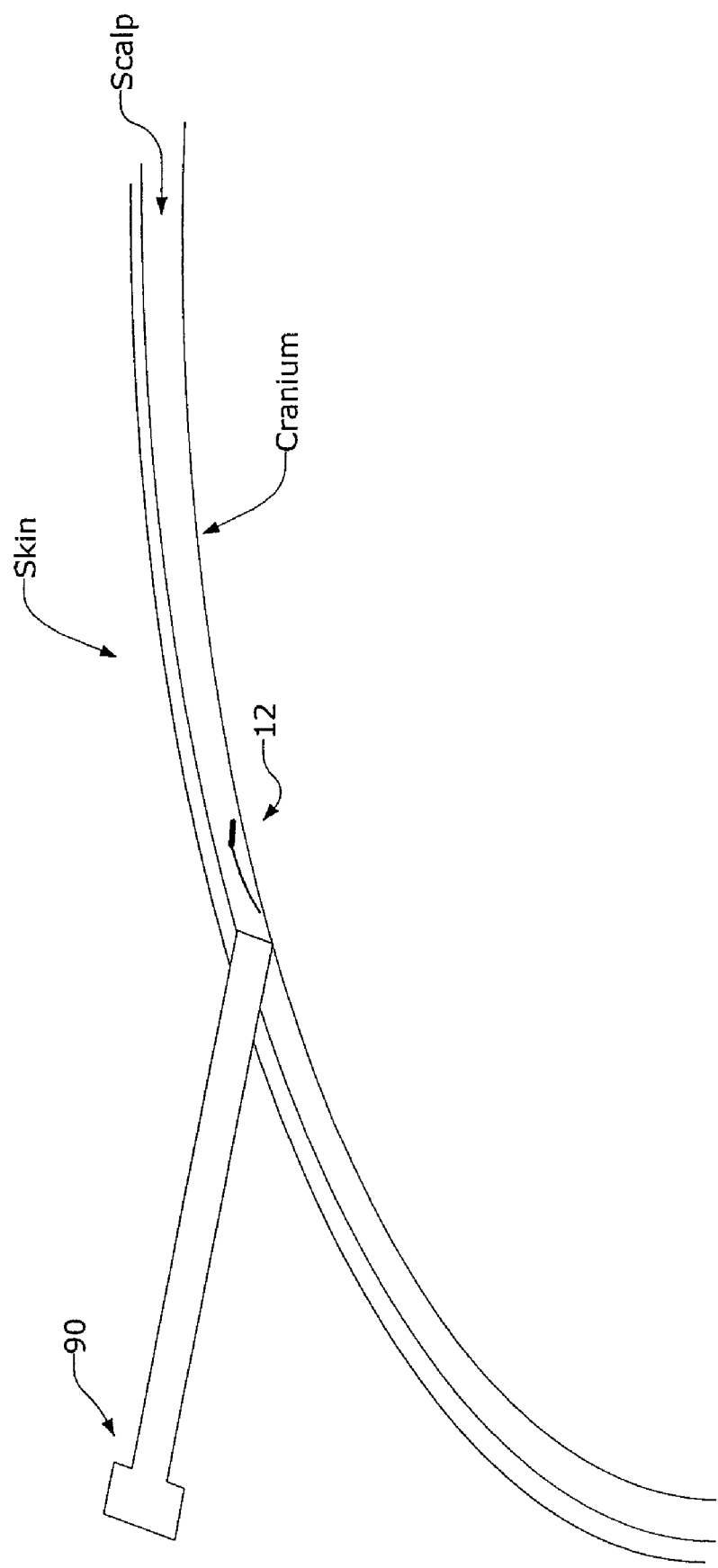
FIG. 6 illustrates a simplified trocar or needle-like device that may be used to implant the implantable device beneath the patient's skin.

As noted above, in preferred embodiments, the implantable devices are implanted in a minimally invasive fashion under the patient's scalp and above an outer surface of the skull. FIG. 6 illustrates a simplified introducer assembly 90 that may be used to introduce the implantable devices into the patient. The introducer assembly 90 is typically in the form of a cannula and stylet or a syringe-like device that can access the target area and inject the implanted device under the skin of the patient. As noted above, the implantable devices 12 are preferably implanted beneath at least one layer of the patient's scalp and above the patient's skull. Because of the small size of the implantable devices 12, the devices may be injected into the patient under local anesthesia in an outpatient procedure by the physician or neurologist. Because the implantable devices are implanted entirely beneath the skin infection risk would be reduced and there would be minimal cosmetic implications. Due to the small size of the implantable devices 12, it may be desirable to have a plurality of implantable devices pre-loaded into a sterile introducer assembly 90 or into a sterile cartridge (not shown) so as to minimize the risk of contamination of the implantable devices 12 prior to implantation.

Figure 7:
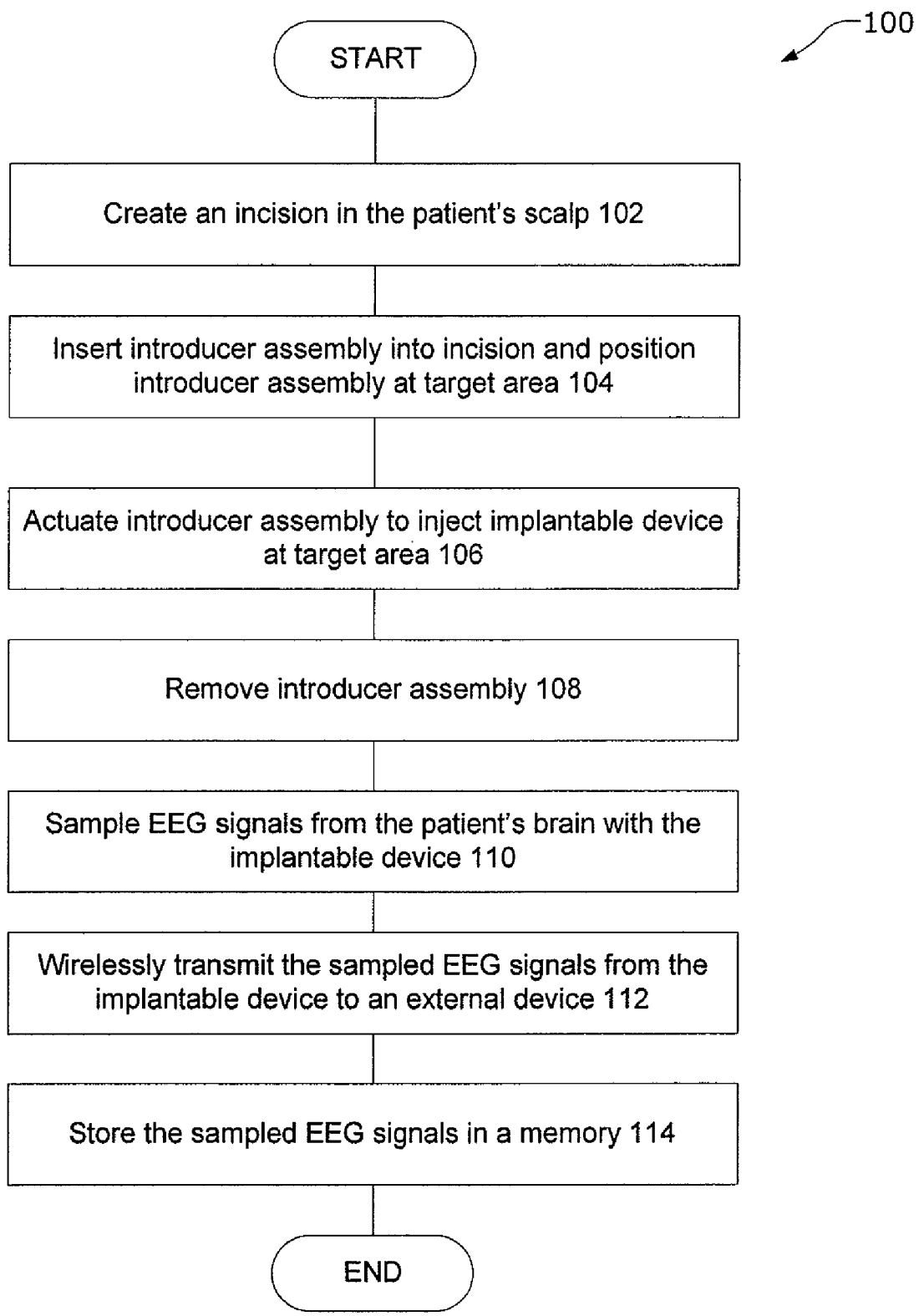
FIG. 7 illustrates a method of inserting an implantable device in the patient and wirelessly sampling EEG signals from a patient.

FIG. 7 schematically illustrates one example of a minimally invasive method 100 of implanting the implantable devices for ambulatory monitoring of a patient's EEG signals. At step 102, an incision is made in the patient's scalp. At step 104, an introducer assembly is inserted into the incision and a distal tip of the introducer assembly is positioned at or near the target site. Of course, the introducer assembly itself may be used to create the incision. For example, if the introducer assembly is in the form of a syringe, the syringe tip may be made to create the incision and steps 102 and 104 may be consolidated into a single step. At step 106, the introducer assembly is actuated to inject the implantable device 12 to the target site. If desired, the introducer may be repositioned to additional target sites underneath the patient's skin and above the skull. If needed, additional incisions may be created in the patient's skin to allow for injection of the implantable device 12 at the additional target sites. After a desired number of implantable devices are placed in the patient, at step 108 the introducer assembly is removed from the target site. At step 110, the implantable devices are activated and used to perform long term monitoring of the patient's EEG signals from each of the target sites. At step 112, the sampled EEG signals are then wirelessly transmitted to an external device. At step 114, the sampled EEG signals may then be stored in a memory in the external device or in another device (e.g., personal computer). If desired, the EEG signals may then be processed in the external device or in a personal computer of the physician.

While not shown in FIG. 7, it may also be desirable to anchor the implantable devices to the patient to reduce the likelihood that the implantable devices are dislodged from their desired position. Anchoring may be performed with tissue adhesive, barbs or other protrusions, sutures, or the like.

Advantageously, the implantable devices are able to monitor EEG signals from the patient without the use of burr holes in the skull or implantation within the brain—which significantly reduces the risk of infection for the patient and makes the implantation process easier. While there is some attenuation of the EEG signals and movement artifacts in the signals, because the implantable devices are below the skin, it is believed that there will be much lower impedance than scalp electrodes. Furthermore, having a compact implantable device 14 below the skin reduces common-mode interference signals which can cause a differential signal to appear due to any imbalance in electrode impedance and the skin provides some protection from interference caused by stray electric charges (static).

While FIG. 7 illustrates one preferred method of implanting the implantable devices in the patient and using the implantable devices to monitor the patient's EEG, the present invention is not limited to such a method, and a variety of other non-invasive and invasive implantation and monitoring methods may be used. For example, while minimally invasive monitoring is the preferred method, the systems and devices of the present invention are equally applicable to more invasive monitoring. Thus, if it is desired to monitor and record intracranial EEG signals (e.g., ECOG), then it may be possible to implant one or more of the implantable devices inside the patient's skull (e.g., in the brain, above or below the dura mater, or a combination thereof) through a burr hole created in the patient's skull.

Once implanted in the patient, the monitoring systems 10 of the present invention may be used for a variety of different uses. For example, in one usage the systems of the present invention may be used to diagnose whether or not the patient has epilepsy. Patients are often admitted to video-EEG monitoring sessions in an EMU to determine if the patient is having seizures, pseudo-seizures, or is suffering from vaso-vagal syncope, and the like. Unfortunately, if the patient has infrequent "seizures," it is unlikely that the short term stay in the EMU will record a patient's seizure and the patient's diagnose will still be unclear. Consequently, in order to improve the patient's diagnosis, in addition to the in-hospital video-EEG monitoring or as an alternative to the in-hospital video-EEG monitoring, the patient may undergo an ambulatory, long term monitoring of the patient's EEG using the system of the present invention for a desired time period. The time period may be one day or more, a week or more, one month or more, two months or more, three months or more, six months or more, one year or more, or any other desired time period in between. The patient may be implanted with the system 10 using the method described above, and after a predetermined time period, the patient may return to the physician's office where the EEG data will be uploaded to the physician's personal computer for analysis. A conventional or proprietary seizure detection algorithm may be applied to the EEG data to determine whether or not a seizure occurred in the monitoring time period. If it is determined that one or more seizures occurred during the monitoring period, the seizure detection algorithm may be used to provide an output to the physician (and/or generate a report for the patient) indicating the occurrence of one or more seizures, and various seizure activity metrics, such as spike count over a period of time, seizure count over a period of time, average seizure duration over a period of time, the pattern of seizure occurrence over time, and other seizure and seizure related metrics. In addition, the software may be used to display the actual EEG signals from specific events or selected events for physician confirmation of seizure activity. Such data may be used as a "baseline" for the patient when used in assessing efficacy of AEDs or other therapies that the patient will undergo.

If the patient has been diagnosed with epilepsy (either using the system of the present invention or through conventional diagnosis methods), the present invention may also be used to determine the epilepsy classification and/or seizure type. To perform such methods, a desired number of implantable devices may be implanted in the patient for the long term monitoring of the patient's pattern of electrical activity in the different portions of the patient's brain. Such monitoring will be able to provide insight on whether or not the patient has partial/focal seizures or generalized seizures. In the event that the patient's epilepsy classification is already known, the classification may determine the desired placement for the implantable devices in the patient. For patients suspected or known to have temporal lobe epilepsy, the implantable devices will likely be focused over the temporal lobe and adjacent and/or over the regions of epileptiform activity. Likewise, for patient's suspected or known to have parietal lobe epilepsy, some or all of the implantable devices will be positioned over the parietal lobe and adjacent and/or over the regions of epileptiform activity. Furthermore, if the seizure focus or foci are known, at least some of the implantable devices may be positioned over the seizure focus or foci and some may be positioned contralateral to the known seizure focus or foci.

Figure 8:
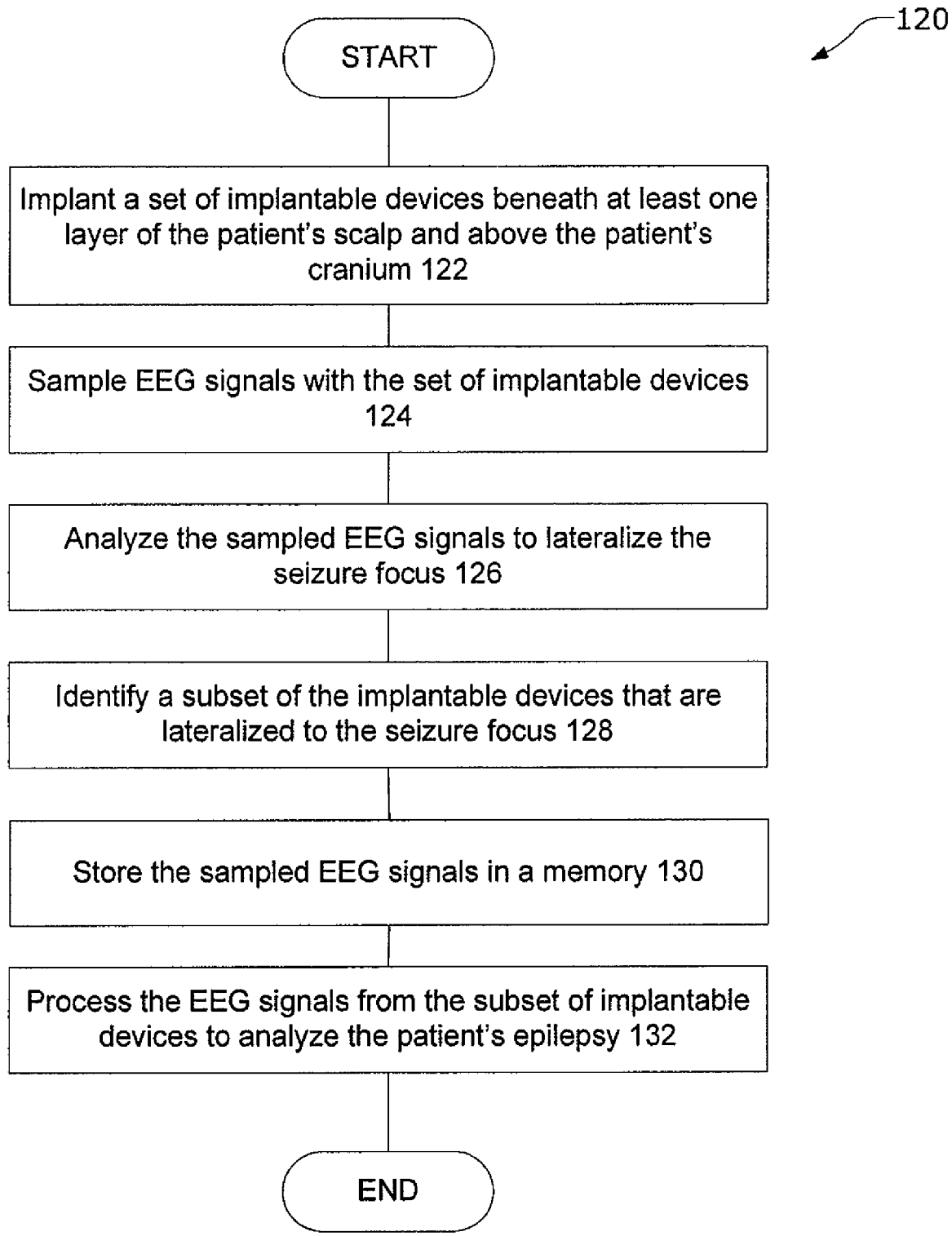
FIG. 8 illustrates a method of lateralizing a seizure focus.

If a seizure focus in the patient has not been lateralized, the present invention may be used to lateralize the seizure focus. FIG. 8 illustrates one method 120 of lateralizing a seizure focus in a patient. At step 122, a set of implantable devices are implanted beneath at least one layer of the patient's scalp and above the patient's skull (or below the skull, if desired). Preferably, the implantable devices will comprise more than two electrodes to improve the ability to localize the seizure focus. For embodiments that only include two electrodes, a very large number of implantable devices may be required to actually localize the seizure focus. In one embodiment, implantation may be carried out using the method steps 102-108 illustrated in FIG. 7. At step 124, the set of implantable devices are used to sample the patient's EEG signals. At step 126, each of the EEG signals from the implantable devices are analyzed over a period of time (e.g., with EEG analysis software, such as a seizure detection algorithm) to monitor the patient's seizure activity and once a seizure has occurred try to lateralize the seizure focus. At step 128, if the seizure focus is lateralized, a subset of the implantable devices that are lateralized to the seizure focus are identified. At steps 130 and 132, the EEG signals from the subset of implantable may continue to be sampled, and such EEG signals may thereafter be stored and processed to analyze the patient's brain activity. The implantable devices that are not lateralized to the focus may be removed from the patient, disabled, or the EEG signals from such implantable devices may be ignored or not captured/stored. However, if desired, such EEG signals may continue to be stored and processed. The location and/or lateralization o the seizure focus may thereafter be used by the physicians to determine whether or not the patient is a candidate for resective surgery or other procedures.

Figure 9:
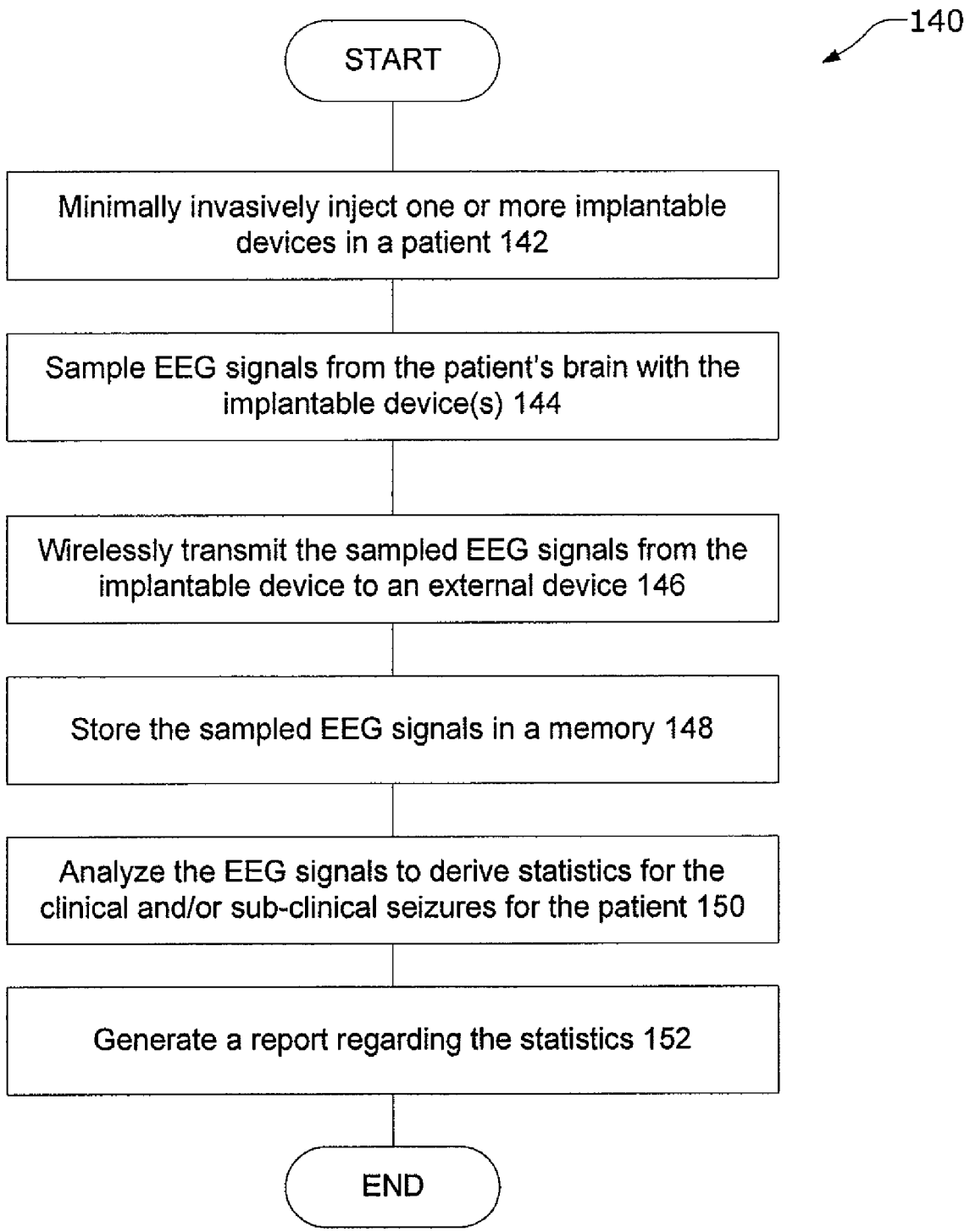
FIG. 9 illustrates a method of measuring seizure activity data for clinical and/or sub-clinical seizures.

In another use, the present invention may be used to quantify seizure activity statistics for the patient. The most common method of quantifying a patient's seizure activity is through patient self reporting using a seizure diary. Unfortunately, it has been estimated that up to 63% of all seizures are missed by patients. Patient's missing the seizures are usually caused by the patients being amnesic to the seizures, unaware of the seizures, mentally incapacitated, the seizures occur during sleep, or the like. FIG. 9 illustrates a simplified method 140 of measuring and reporting a patient's seizure activity statistics. At step 142, one or more implantable devices are implanted in a patient, typically in a minimally invasive fashion as shown in FIG. 7. At step 144, the implantable devices are used to substantially continuously sample EEG signals from the patient. At step 146, the sampled EEG signals are wirelessly transmitted from the implantable device to an external device. At step 148, the sampled EEG signals are stored in a memory. At step 150, the stored EEG signals are analyzed with EEG analysis software, typically using a seizure prediction and/or detection algorithm, to derive statistics for the clinical seizures and/or the sub-clinical seizures for the patient based on the long-term, ambulatory EEG data. For example, the following statistics may be quantified using the present invention:

Seizure count over a time period—How many clinical and sub-clinical seizures does the patient have in a specific time period?

Seizure frequency—How frequent does the patient have seizures? What is the seizure frequency without medication and with medication? Without electrical stimulation and with electrical stimulation?

Seizure duration—How long do the seizures last? Without medication and with medication? Without electrical stimulation and with electrical stimulation?

Seizure timing—When did the patient have the seizure? Do the seizures occur more frequently at certain times of the day?

Seizure patterns—Is there a pattern to the patient's seizures? After certain activities are performed? What activities appear to trigger seizures for this particular patient?

Finally, at step 152, report generation software may be used to generate a report based on the statistics for the seizure activity. The report may include some or all of the statistics described above, an epilepsy/no epilepsy diagnosis, identification of a seizure focus, and may also include the EEG signal(s) associated with one or more of the seizures. The report may include text, graphs, charts, images, or a combination thereof so as to present the information to the physician and/or patient in an actionable format. Advantageously, the systems may be used to generate a baseline report for the patient, and the system may be continuously used to record data over a long period of time and provide a quantification of the patient's change in their condition and/or the efficacy of any therapy that the patient is undergoing (described in more detail below).

As noted above, the present invention enables the documentation and long term monitoring of sub-clinical seizures in a patient. Because the patient is unaware of the occurrence of sub-clinical seizures, heretofore the long term monitoring of sub-clinical seizures was not possible. Documentation of the sub-clinical seizures may further provide insight into the relationship between sub-clinical seizures and clinical seizures, may provide important additional information relevant to the effectiveness of patient therapy, and may further enhance the development of additional treatments for epilepsy.

Figure 10:
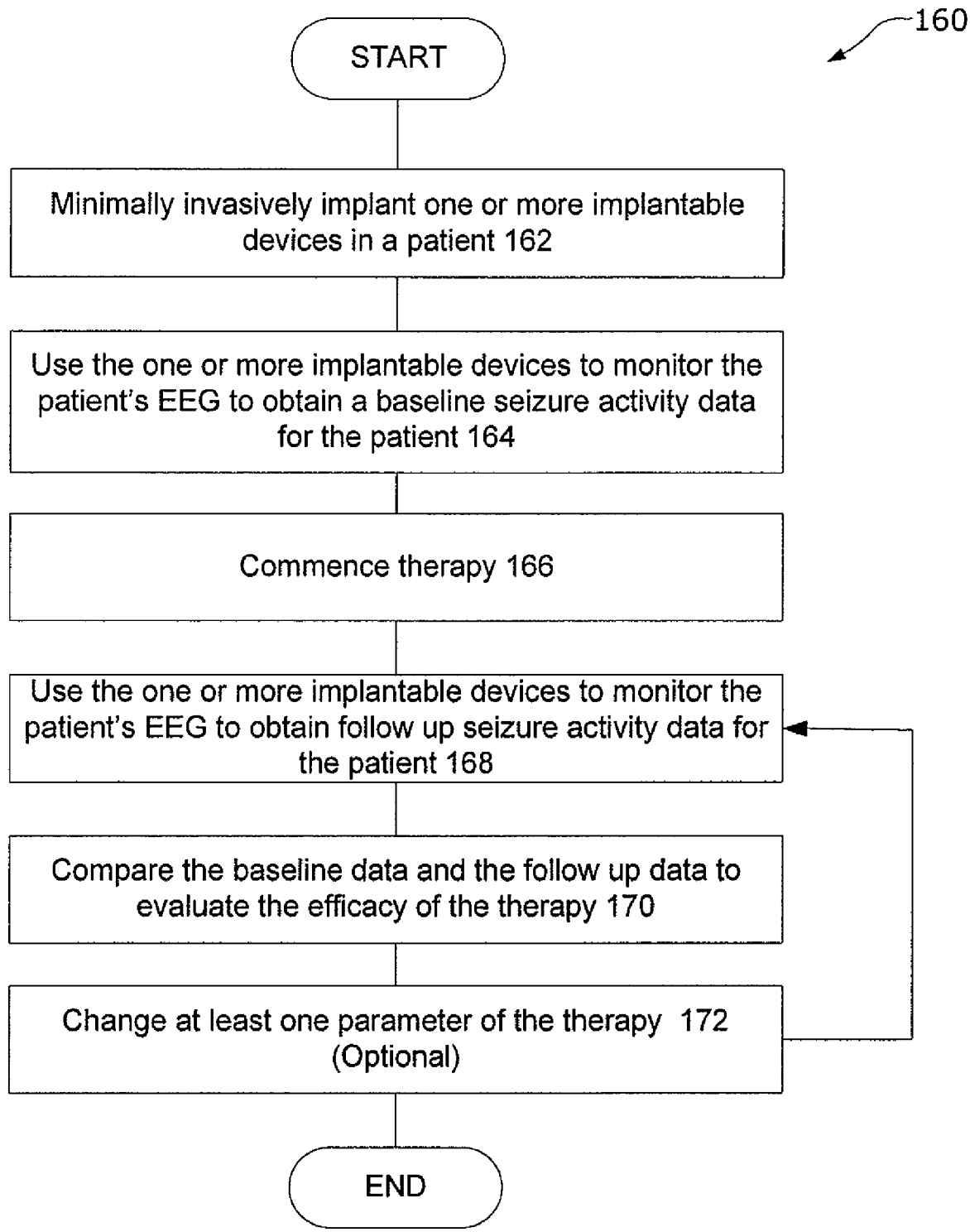
FIG. 10 illustrates a method of evaluating efficacy of a therapy.

FIG. 10 illustrates one exemplary method of how the seizure activity data may be used to evaluate the efficacy or clinical benefit of a current or potential therapy and allow for the intelligent selection of an appropriate therapy for an individual patient and/or stopping the usage of ineffective therapies. Currently, effectiveness of the AED therapy is based on self-reporting of the patient, in which the patient makes entries in a diary regarding the occurrence of their seizure(s). If the entries in the patient diary indicate a reduction in seizure frequency, the AED is deemed to be effective and the patient continues with some form of the current regimen of AEDs. If the patient entries in the patient diary do not indicate a change in seizure frequency, the AEDs are deemed to be ineffective, and typically another AED is prescribed—and most often in addition to the AED that was deemed to be ineffective. Because AEDs are typically powerful neural suppressants and are associated with undesirable side-effects, the current methodology of assessing the efficacy of the AEDs often keeps the patient on ineffective AEDs and exposes the patient to unnecessary side-effects.

By way of example, a medically refractory patient coming to an epilepsy center for the first time might first have the system of the present invention implanted and then asked to collect data for a prescribed time period, e.g., 30 days. The initial 30 days could be used to establish a baseline measurement for future reference. The physician could then prescribe an adjustment to the patient's medications and have the patient collect data for another time period, e.g., an additional 30 day period. Metrics from this analysis could then be compared to the previous analysis to see if the adjustment to the medications resulted in an improvement. If the improvement was not satisfactory, the patient can be taken off of the unsatisfactory medication, and a new medication could be tried. This process could continue until a satisfactory level of seizure control was achieved. The present invention provides a metric that allows physicians and patients to make informed decisions on the effectiveness and non-effectiveness of the medications.

FIG. 10 schematically illustrates one example of such a method. At step 162, one or more implantable devices are implanted in the patient, typically in a minimally-invasive fashion. At step 164, the one or more implantable devices are used to monitor the patient's EEG to obtain a baseline measurement for the patient. The baseline measurement is typically seizure activity statistics for a specific time period (e.g., number of seizures, seizure duration, seizure pattern, seizure frequency, etc.). It should be appreciated however, that the baseline measurement may include any number of types of metrics. For example, the baseline metric may include univariate, bivariate, or multivariate features that are extracted from the EEG, or the like. In one preferred embodiment, the baseline measurement is performed while the patient is not taking any AEDs or using any other therapy. In other embodiments, however, the patient may be taking one or more AEDs and the baseline measurement will be used to evaluate adjustments to dosage or efficacy of other add-on therapies.

At step 166, the therapy that is to be evaluated is commenced. The therapy will typically be an AED and the patient will typically have instructions from the neurologist, epileptologist, or drug-manufacturer regarding the treatment regimen for the AED. The treatment regimen may be constant (e.g., one pill a day) throughout the evaluation period, or the treatment regimen may call for varying of some parameter of the therapy (e.g., three pills a day for the first week, two pills a day for the second week, one pill a day for the third week, etc.) during the evaluation period. During the evaluation period, the implantable device(s) will be used to substantially continuously sample the patient's EEG and assess the effect that the AED has on the patient's EEG. The sampled EEG may thereafter be processed to obtain a follow-up measurement for the patient (Step 168). If the baseline measurement was seizure statistics for the baseline time period, then the follow-up measurement will be the corresponding seizure statistics for the evaluation period. At step 170, the baseline measurement is compared to the follow-up measurement to evaluate the therapy. If the comparison indicates that the therapy did not significantly change the patient's baseline, the therapy may be stopped, and other therapies may be tried.

Currently, the primary metric in evaluating the efficacy of an AED is whether or not the AED reduces the patient's seizure count. In addition to seizure count, the systems of the present invention would be able to track any reduction in seizure duration, modification in seizure patterns, reduction in seizure frequency, or the like. While seizure count is important, because the present invention is able to provide much greater detail than just seizure count, efficacy of an AED may be measured using a combination of additional metrics, if desired. For example, if the patient was having a large number of sub-clinical seizures (which the patient was not aware of) and the AED was effective in reducing or stopping the sub-clinical seizures, the systems of the present invention would be able to provide metrics for such a situation. With conventional patient diary "metrics", the patient and physician would not be aware of such a reduction, and such an AED would be determined to be non-efficacious for the patient. However, because the present invention is able to provide metrics for the sub-clinical seizures, the efficacious medication could be continued, if desired.

At step 172, the epileptologist or neurologist may decide to change one or more parameters of the therapy. For example, they may change a dosage, frequency of dosage, form of the therapy or the like, and thereafter repeat the follow-up analysis for the therapy with the changed parameter. After the "second" follow up measurement is complete, the second follow up data may be obtained and thereafter compared to the "first" follow up measurements and/or the baseline measurements. While not shown in FIG. 10, the method may also comprise generating a report that details the patient's metrics, change in metrics, recommendations, etc.

Figure 11:
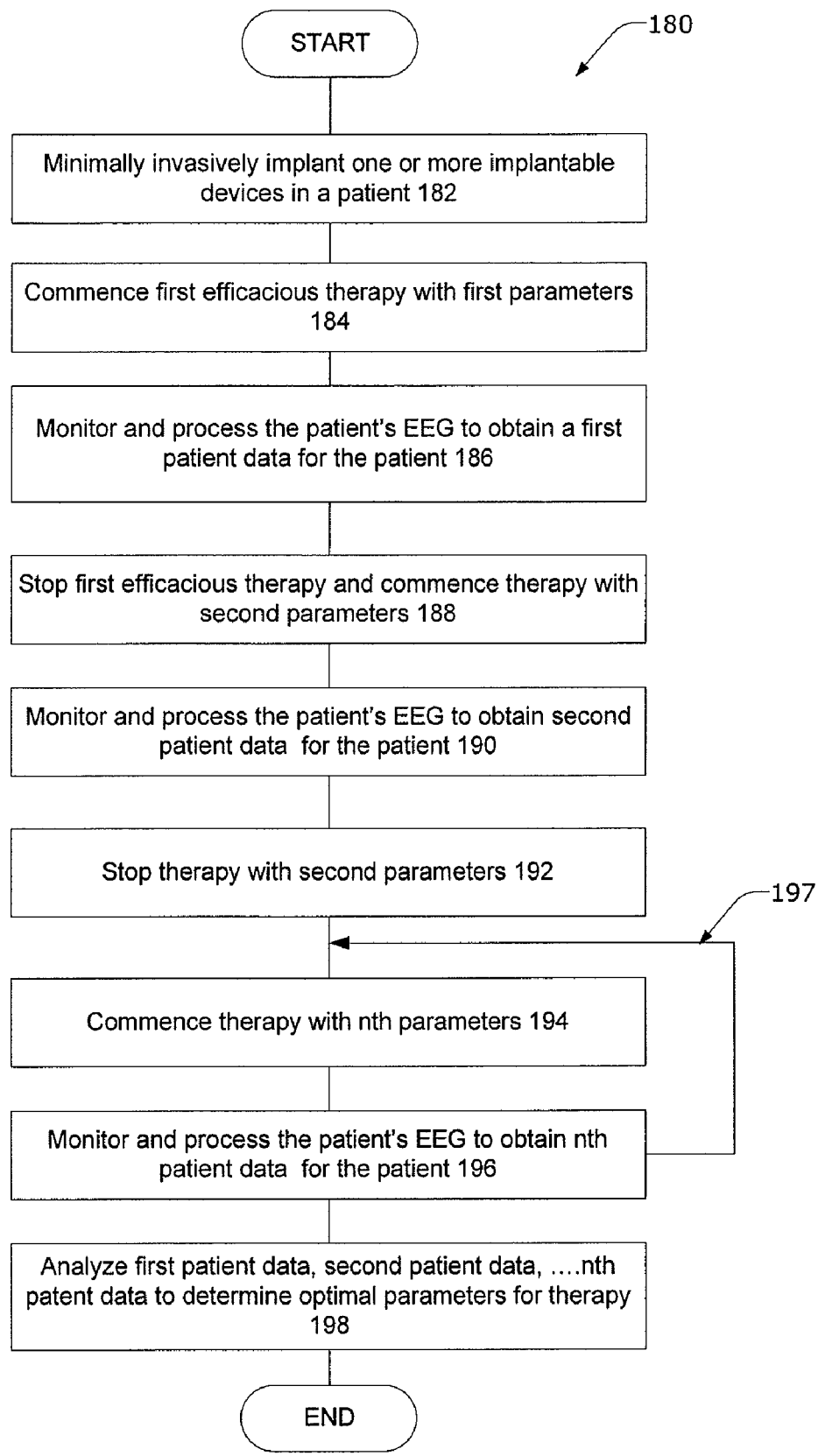
FIG. 11 illustrates a method of titrating an efficacious therapy.

In addition to evaluating an efficacy of a therapy for an individual patient, the metrics that are provided by the present invention also enable an intelligent titration of a patient's medications. As shown in FIG. 11, if the patient is on a treatment regimen of an efficacious therapy, the present invention may be used to reduce/titrate a dosage or frequency of intake of the AED or AEDs, or other pharmacological agents. At step 182, one or more implantable devices are minimally invasively implanted in the patient. Typically, the patient will already be on a treatment regimen of the efficacious therapy, but if not, the efficacious therapy is commenced with the prescribed parameters, e.g., "standard" dosage (Step 184). At step 186, the patient's EEG (and/or other physiological signal) is monitored for a desired time period to obtain a first patient data measurement for the patient (e.g., the baseline measurement). Similar to previous embodiments, the first patient data measurement may be any desired metrics, but will typically be clinical seizure frequency, clinical seizure duration, sub-clinical seizure frequency, sub-clinical seizure duration, medication side effects. At step 188, after the baseline measurement has been taken, the first efficacious therapy is stopped and a therapy with at least one changed parameter is started (referred to as "therapy with second parameters" in FIG. 11). Typically, the changed parameter will be a reduction in dosage, but it could be changing a frequency of the same dosage, a change in formulation or form of the same AED, or the like.

At step 190, the patient's EEG is monitored and processed to obtain a second patient data measurement for the patient (e.g., follow-up data measurement). If the neurologist or epileptologist is satisfied with the results, the titration may end. But in many embodiments, the titration process will require more than one modification of parameters of the therapy. In such embodiments, the second therapy is stopped (step 192), and a therapy with $N^{th}$ parameters (e.g., third, fourth, fifth . . . ) is commenced (step 194). Monitoring and processing of the patient's EEG signals are repeated (step 196), and the process is repeated a desired number of times (as illustrated by arrow 197). Once the desired numbers of modifications to the therapy have been made, the various patient data measurements may be analyzed (e.g., compared to each other) to determine the most desirous parameters for the therapy (step 198). As can be imagined, any number of different analyses or statistical methods may be performed. In one embodiment, seizure activity statistics (e.g., clinical seizure frequency, sub-clinical seizure frequency, seizure rate per time period, seizure duration, seizure patterns, etc.) may be used to assess the efficacy and differences between the therapies.

With the instrumentation provided by the present invention, the process of selecting appropriate AEDs and the titration of dosages of such AEDs could occur much faster and with much greater insight than ever before. Further, the chance of a patient remaining on an incremental AED that was providing little incremental benefit would be minimized. Once a patient was under control, the patient could cease the use of the system, but the implantable device could remain in the patient. In the future, the patient might be asked to use the system again should their condition change or if the efficacy of the AED wane due to tolerance effects, etc.

While FIGS. 10 and 11 are primarily directed toward assessing the efficacy of a pharmacological agent (e.g., AED), such methods are equally applicable to assessing the efficacy and optimizing patient-specific parameters of non-pharmacological therapies. For example, the present invention may also be used to evaluate and optimize parameters for the electrical stimulation provided by the Vagus Nerve Stimulator (sold by Cyberonics Corporation), Responsive Neurostimulator (RNS) (manufactured by NeuroPace Corporation), Deep Brain Stimulators (manufactured by Medtronic), and other commercial and experimental neural and spinal cord stimulators.

Furthermore, the systems of the present invention will also be able to provide metrics for the effectiveness of changes to various electrical parameters (e.g., frequency, pulse amplitude, pulse width, pulses per burst, burst frequency, burst/no-burst, duty cycle, etc.) for the electrical stimulation treatments. Such metrics will provide a reliable indication regarding the effectiveness of such parameter changes, and could lead to optimization of stimulation for parameters for individual patients or the patient population as a whole.

In addition to facilitating the selection of appropriate AEDs and titration of dosages of the AEDs for an individual patient, the present invention may have beneficial use in the clinical trials for the development of experimental AEDs and other therapies for the epileptic patient population (and other neurological conditions). One of the greatest barriers to developing new AEDs (and other pharmacological agents) is the costs and difficulties associated with the clinical trials. Presently, the standard metric for such clinical trials is patient seizure count. Because this metric is self-reported and presently so unreliable, to power the study appropriately clinical trials for AEDs must involve very large patient populations, in which the patient's must have a high seizure count. At an estimated cost of $20,000 per patient for pharmacological trials, the cost of developing a new drug for epilepsy is exceedingly high and may deter drug companies from developing AEDs.

The minimally invasive systems of the present invention may be used to facilitate these clinical trials. Such systems could result in significantly more reliable data, which would result in much smaller sample patient populations, and could include a broader types of patients (e.g., patient's who don't have frequent seizures) for appropriately powering the study. Improved certainty in efficacy would also reduce risk to the company, as it moved from safety studies to efficacy studies. Significantly reducing risk and improving the economics of these studies by reducing the required number of study subjects could lead to an increase in the development of new therapies for this patient population, and other patient populations.

It should be appreciated however, that the present invention is not limited to clinical trials for epilepsy therapies, and the present invention has equal applicability to other clinical trials (e.g., cancer therapy, cardiac therapy, therapy for other neurological disorders, therapy for psychiatric disorders, or the like.)

Figure 12:
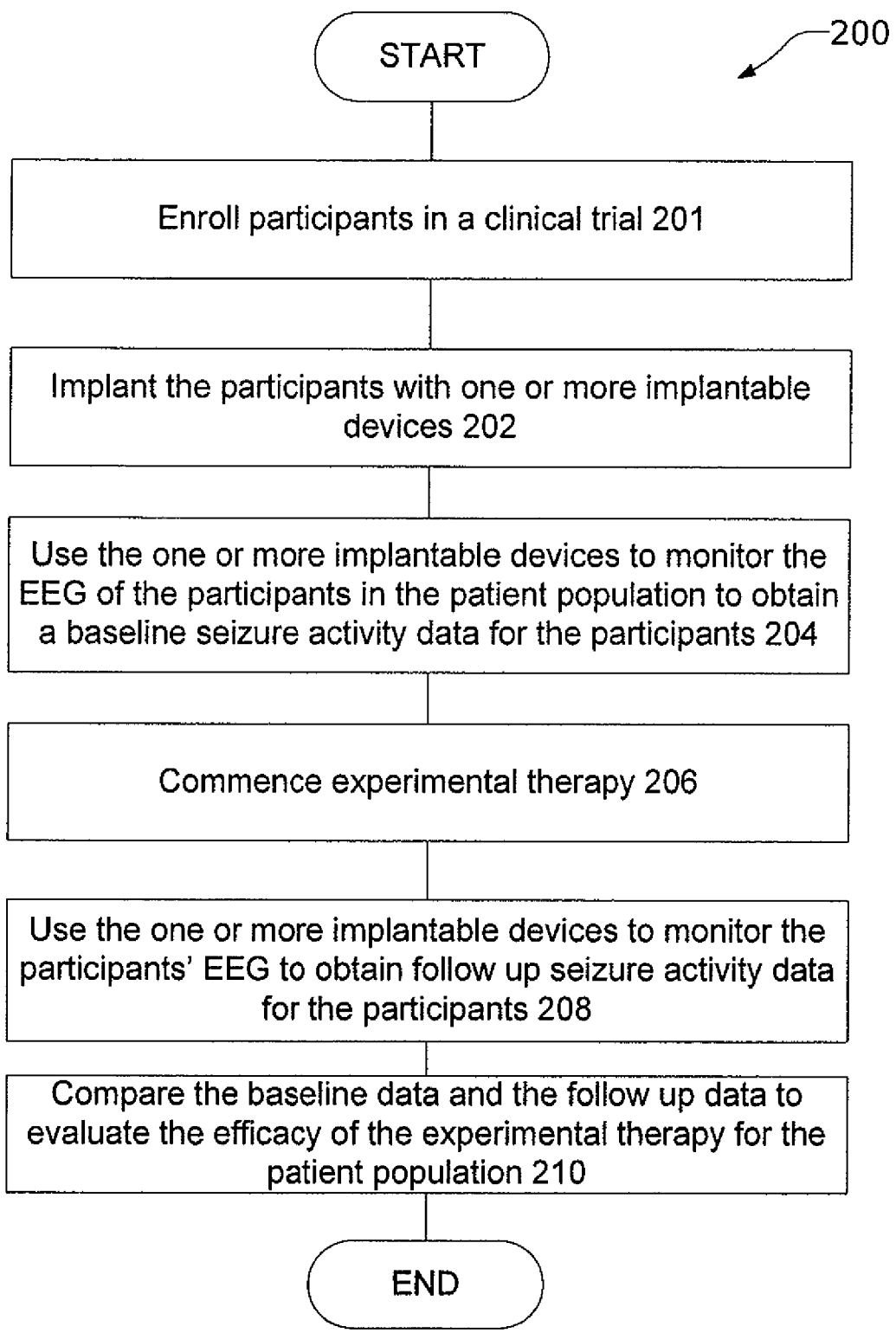
FIG. 12 illustrates a simplified method of performing a clinical trial.
Figure 13:
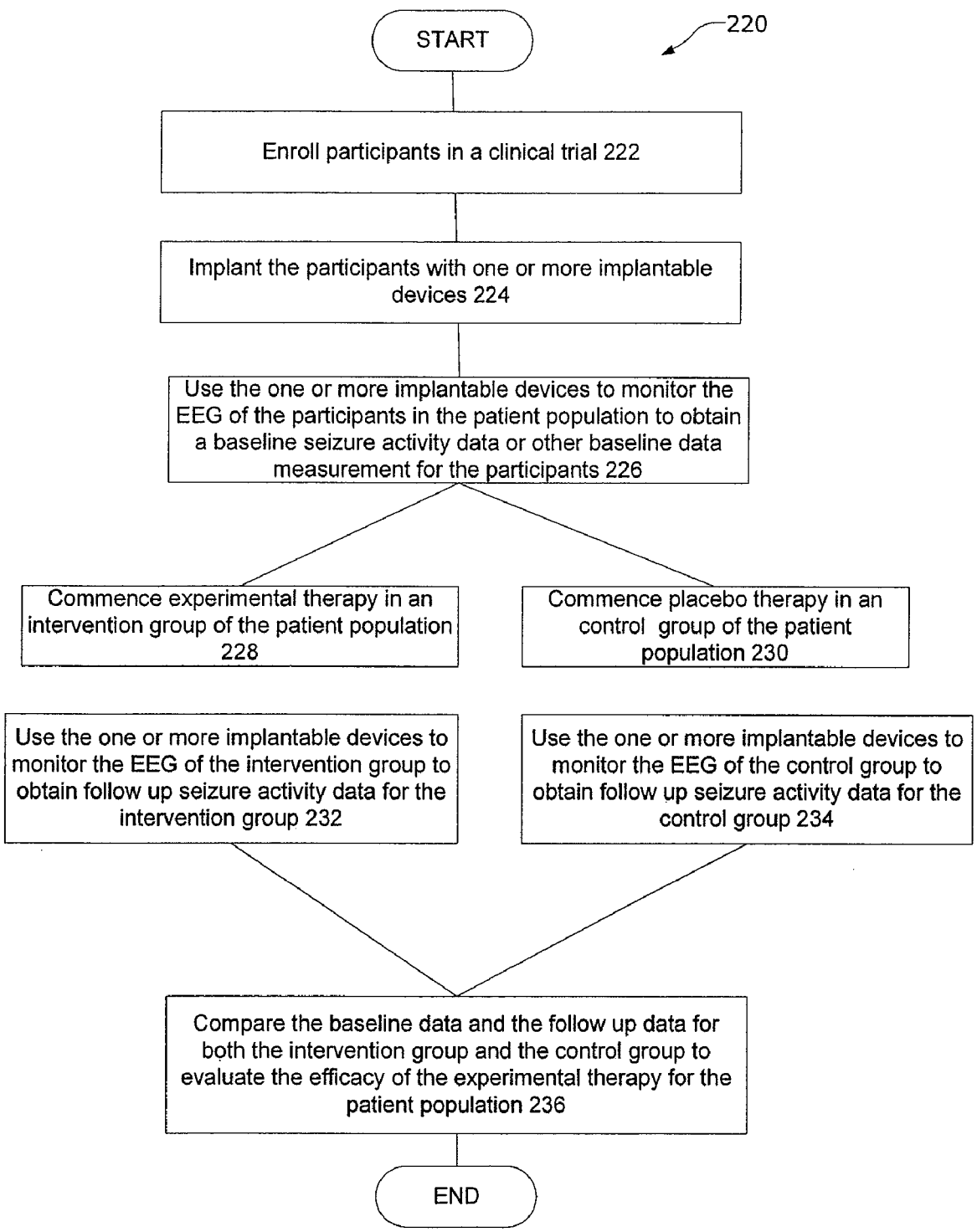
FIG. 13 illustrates a more detailed method of performing a clinical trial.

FIGS. 12-13 illustrate some methods of performing clinical trials that are encompassed by the present invention. The present invention is applicable to any type of clinical trial, including but not limited to a randomized clinical trial, e.g., an open clinical trial, a single-blinded study, a double-blinded study, a triple-blinded study, or the like.

FIG. 12 illustrates a simplified method 200 of performing a clinical trial according to the present invention. At step 201 participants are enrolled in the clinical trial. At step 202, selected participants in the clinical trial are implanted with one or more leadless, implantable devices (such as those described above) in order to sample one or more physiological signal from the patient. Typically, the physiological signal is an EEG signal. In preferred embodiments, the EEG signal is sampled substantially continuously for the entire baseline period for each of the participants in the clinical trial. In alternative embodiments, it may be desirable to sample the EEG signals in a non-continuous basis.

At step 204, the sampled EEG signals are processed for a desired time period to obtain a first patient data measurement, e.g., a baseline data measurement, for each of the participants in the clinical trial. After the participants have commenced the experimental therapy (typically by following a prescribed treatment regimen by the investigator or drug company), the same implantable devices are used to sample the EEG signals from the participant for an evaluation period, and the EEG signals are processed to provide a second patient data measurement, e.g., follow-up measurement (Step 206, 208). At step 210, the baseline data measurement and the follow-up data measurement may be compared using conventional statistical methods in order to evaluate the experimental therapy on the patient population.

While not shown in FIG. 12, it may be desirable to have a "second" evaluation period (and a second follow-up measurement) in which at least one parameter of the experimental therapy is changed and the changed experimental therapy is administered to the patient. Similar to the method of FIG. 11, such a method may provide guidance to finding the appropriate dosing, formulation, and/or form of delivery of the experimental therapy.

The baseline period and the evaluation period are typically the same time length. The time length may be any desired time, but is typically at least one week, and preferably between at least one month and at least three months.

Evaluation of the experimental therapy may be to evaluate dosing requirements, evaluate toxicity of the experimental therapy, evaluate long-term adverse effects of the experimental therapy or to determine efficacy of the experimental therapy. In one preferred embodiment, the comparison may simply determine whether there was a statistically significant change in a seizure count between the baseline period and the evaluation period. But as noted above, the baseline data measurement and follow-up data measurement may include any metric that is extracted from the EEG signals.

FIG. 13 illustrates a more detailed method of performing a clinical trial according to the present invention. At step 222 participants are enrolled in the clinical trial. At step 224, the participants in the clinical trial are implanted with one or more leadless, implantable devices (such as those described above) in order to sample one or more physiological signal from the patient. Typically, the physiological signal is an EEG signal. In preferred embodiments, the EEG signal is sampled substantially continuously for the entire baseline period for each of the participants in the clinical trial.

At step 226, the sampled BEG signals are processed to obtain a first patient data measurement, e.g., a baseline data measurement, for each of the participants in the clinical trial. If the patients do not have any seizures during the baseline period, then the patients will most likely be excluded from the remainder of the clinical trial. The remaining participants in the clinical trial are then broken into an intervention group and a control group. The experimental therapy is commenced in the intervention group of the patient population (step 228), and a placebo therapy is commenced in the control group of the patient population (step 230).

The implantable devices are used to substantially continuously sample the EEG signals of both the intervention group and the control group during an evaluation period. The EEG signals are processed to obtain follow-up seizure activity data (or some other metric) for both groups (step 232, 234). Thereafter, the baseline data and the follow up data for both the intervention group and the control group are analyzed, (e.g., compared with each other) to evaluate the efficacy of the experimental therapy for the patient population (step 236). While not shown in FIG. 13, the method may further include changing one or more parameters of the experimental therapy and comparing the "second" follow up data to the baseline data and/or other follow up data.

While the preferred embodiments described above are directed toward evaluating experimental AEDs in the clinical trial, the present invention is equally applicable to clinical trials for other experimental pharmacological agents, biologics, devices, and other non-pharmacological therapies. For example, the present invention may also be used to evaluate the Vagus Nerve Stimulator (sold by Cyberonics Corporation), Responsive Neurostimulator (RNS) (manufactured by NeuroPace Corporation), Deep Brain Stimulators manufactured by Medtronic, and other commercial and experimental neural and spinal cord stimulators. The minimally invasive systems of the present invention may be implanted in patients who are equipped with any of the above stimulators to provide metrics regarding the efficacy of the electrical stimulation treatments.

Furthermore, the systems of the present invention will also be able to provide metrics for the effectiveness of changes to various electrical parameters (e.g., frequency, pulse amplitude, pulse width, pulses per burst, burst frequency, burst/no-burst, etc.) for the electrical stimulation treatments. Such metrics will provide a reliable indication regarding the effectiveness of such parameter changes, and could lead to optimization of stimulation for parameters for individual patients or the patient population as a whole.

Figure 14:
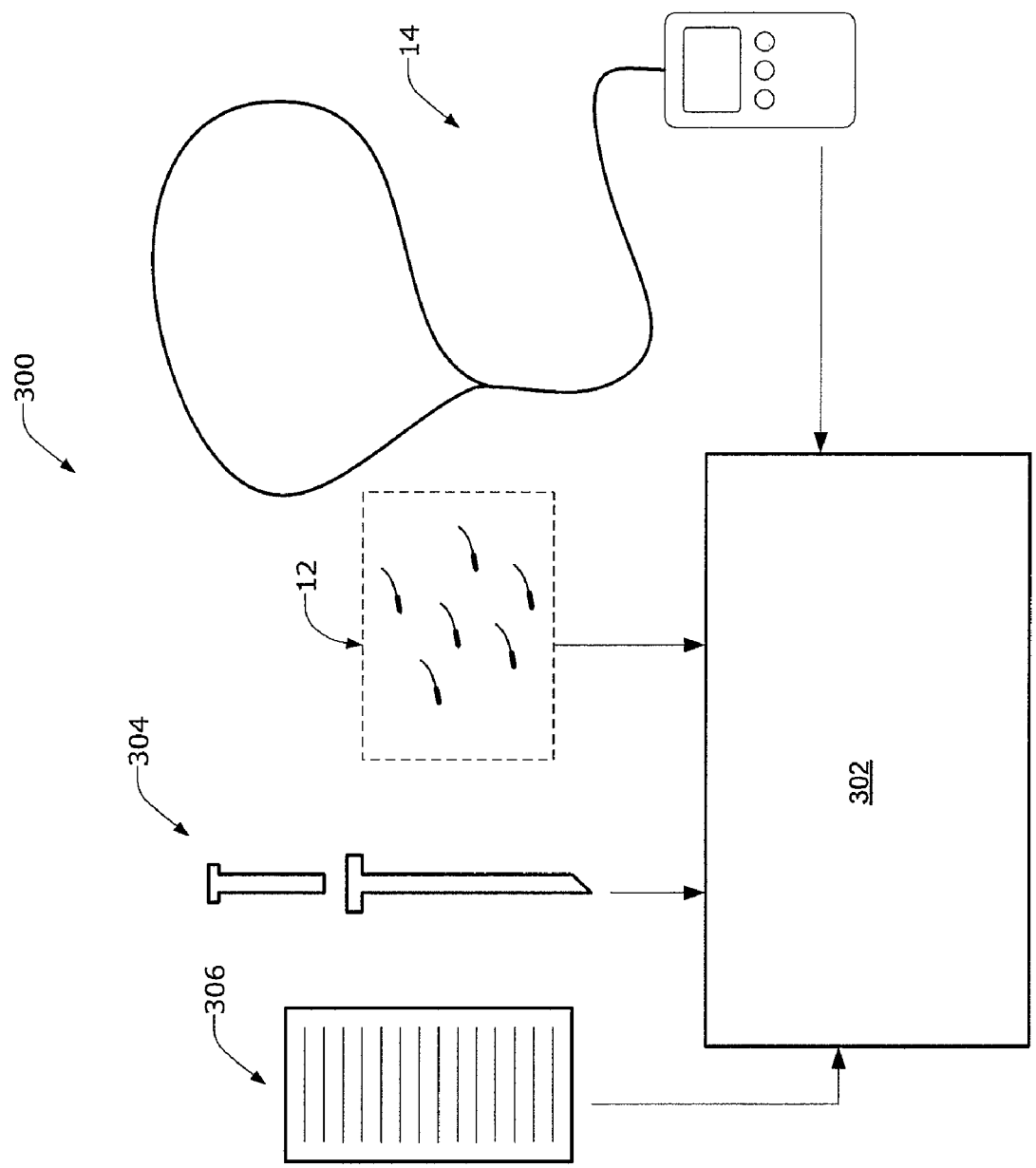
FIG. 14 is a kit that is encompassed by the present invention.

FIG. 14 illustrates a packaged system or kit 300 that is encompassed by the present invention. The packaged system 300 may include a package 302 that has one or more compartments for receiving an introducer assembly 304 and one or more implantable devices 12. The introducer 304 is typically in the form of a syringe-like device or a cannula and stylet. The implantable device 12 may include any of the embodiments described herein. One or more of the implantable devices 12 may be pre-loaded within the introducer 304. In other embodiments, the implantable devices 12 may be loaded in its separate sterile packaging (shown in dotted lines) for easy loading into the introducer 304. The packaged system 300 may include instructions for use ("IFU") 306 that describe any of the methods described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, the present invention also encompasses other more invasive embodiments which may be used to monitor the patient's neurological system.

Alternative embodiments of the implantable device of the present invention may require a neurosurgeon to create a more invasive incision in the patient's scalp. For example, it may be desirable to use a low profile device that is not substantially cylindrical, but instead is substantially planar or concave so as to conform to the curvature of the patient's skull. Such embodiments would likely not be able to be implanted without general anesthesia and may require a surgeon to implant the device.

On the other hand, in some embodiments it may be desirable to be completely non-invasive. Such embodiments include "implantable" devices 12 that are not actually implanted, but instead are "wearable" and may be attached to the outer surface of the skin with adhesive or a bandage so as to maintain contact with the patient's skin. For example, it may be possible to surface mount the device 12 behind the ears, in the scalp, on the forehead, along the jaw, or the like. Because the electrodes are wireless and are such a small size, unlike conventional electrodes, the visual appearance of the electrodes will be minimal.

Furthermore, in some embodiments, it may be desirable to modify the implantable device 12 to provide stimulation to the patient. In such embodiments, the implantable device 12 will include a pulse generator and associated hardware and software for delivering stimulation to the patient through the first and second electrodes 24, 26 (or other electrodes coupled to the device. In such embodiments, the external device 14 will include the hardware and software to generate the control signals for delivering the electrical stimulation to the patient.

While the above embodiments describe that power to the implanted devices may be derived wirelessly from an external device and/or from a battery in the implanted device, it should be appreciated that the internal devices may derive or otherwise "scavenge" power from other types of conventional or proprietary assemblies. Such scavenging methods may be used in conjunction with the external power source and/or the internal power source, or it may be used by itself to provide the necessary power for the implanted devices. For example, the implanted devices may include circuitry and other assemblies (e.g., a microgenerator) that derive and store power from patient-based energy sources such as kinetic movement/vibrations (e.g., gross body movements), movement of organs or other bodily fluids (e.g., heart, lungs, blood flow), and thermal sources in the body (e.g., temperature differences and variations across tissue). As can be imagined, such technology could reduce or eliminate the need for recharging of an implanted battery, replacement of a depleted battery, and/or the creation of an external RF field—and would improve the ease of use of the devices by the patients.

Some embodiments of the monitoring system may include an integral patient diary functionality. The patient diary may be a module in the external device and inputs by the patient may be used to provide secondary inputs to provide background information for the sampled EEG signals. For example, if a seizure is recorded, the seizure diary may provide insight regarding a trigger to the seizure, or the like. The diary may automatically record the time and date of the entry by the patient. Entries by the patient may be a voice recording, or through activation of user inputs on the external device. The diary may be used to indicate the occurrence of an aura, occurrence of a seizure, the consumption of a meal, missed meal, delayed meal, activities being performed, consumption of alcohol, the patient's sleep state (drowsy, going to sleep, waking up, etc.), mental state (e.g., depressed, excited, stressed), intake of their AEDs, medication changes, missed dosage of medication, menstrual cycle, illness, or the like. Thereafter, the patient inputs recorded in the diary may also be used by the physician in assessing the patient's epilepsy state and/or determine the efficacy of the current treatment. Furthermore, the physician may be able to compare the number of seizures logged by the patient to the number of seizures detected by the seizure detection algorithm.

It is intended that the following claims define the scope of the invention and that methods and structures within the scope of these claims and their equivalents be covered thereby.

What is claimed is:

1. A method for selecting a therapy for a patient suffering from a neurological or psychiatric condition, the method comprising:

implanting a monitoring device between at least one layer of the scalp and the skull, wherein said implanting comprises injecting the monitoring device between at least one layer of the scalp and the skull or delivering the monitoring device through a cannula to a target area;

commencing a first therapy;

monitoring a physiological signal from the patient with the implanted device on an ambulatory basis for a first time period after commencement of the first therapy, wherein said monitoring for the first time period comprises sampling the physiological signal with the implanted device;

commencing a second therapy;

monitoring a physiological signal from the patient with the implanted device on an ambulatory basis for a second time period after commencement of the second therapy, wherein said monitoring for the second time period comprises sampling the physiological signal with the implanted device;

processing the physiological signals from the first time period and second time period; and analyzing the processed physiological signals to select an appropriate therapy for the patient.

2. The method of claim 1 wherein the neurological condition comprises epilepsy and the first and second therapy comprise different pharmacological agents, wherein said analyzing comprises measuring seizure activity data from the first and second time periods, wherein seizure activity data comprises at least one of a number of clinical seizures during the first time period, a number of sub-clinical seizures during the first time period, seizure duration, seizure patterns, seizure frequency, and time of day of seizure occurrence.

3. The method of claim 1 wherein monitoring the physiological signal for each of the first time period and the second time period comprises:

wirelessly transmitting a signal encoded with data indicative of the sampled physiological signal from the implanted device to a device that is external to the patient's body; and storing the sampled physiological signal in a memory that is external to the patient's body.

4. The method of claim 3 wherein said monitoring during the first time period is performed substantially continuously and said monitoring during the second time period is performed substantially continuously.

5. The method of claim 3 wherein the implanted device is leadless.

6. The method of claim 3 wherein the implanted device is powered by an externally generated radiofrequency signal.

7. The method of claim 3 wherein the implanted device is powered by an assembly that derives and stores power from patient-based energy sources.

8. The method of claim 1 further comprising sampling a physiological signal from the patient with the implanted device prior to commencement of the first and second therapy to establish a patient baseline, wherein analyzing comprises comparing the patient baseline and processed physiological signals from the first and second time period.

9. The method of claim 1 further comprising stopping the first therapy prior to commencing the second therapy.

10. The method of claim 1, wherein the step of commencing a first therapy comprises providing a first pharmacological agent for treating epilepsy, and further wherein the step of commencing a second therapy comprises providing a second pharmacological agent for treating epilepsy different from the first pharmacological agent.

11. The method of claim 1, wherein said implanting the monitoring device comprises injecting the monitoring device between at least one layer of the scalp and the skull.

12. The method of claim 1, wherein said implanting the monitoring device comprises delivering the monitoring device through the cannula to the target area.

13. A method for optimizing parameters of a selected therapy for patient having a neurological or psychiatric condition, the method comprising:
- implanting a device in between a patient's skull and at least one layer of the scalp, wherein said implanting comprises injecting the device between the skull and at least one layer of the scalp or delivering the device through a cannula to a target area;
- commencing a therapy;
- sampling a physiological signal from the patient on an ambulatory basis with the implanted device after commencement of the therapy for a first time period;
- changing at least one parameter of the therapy;
- sampling the physiological signal from the patient on an ambulatory basis with the implanted device for a second time period after the at least one parameter of the therapy is changed;
- processing the physiological signal from the first time period and second time period; and
- analyzing the processed physiological signals from the first and second time periods to determine desirable parameters for the patient's therapy.

14. The method of claim 13 wherein the device is leadless and is in wireless communication with a device external to the patient, the method further comprising wirelessly transmitting a data signal encoded with data that is indicative of the sampled physiological signal from the leadless implanted device and storing the data signal in a memory of the external device.

15. The method of claim 14 wherein the leadless device is powered by an externally generated radiofrequency signal.

16. The method of claim 14 wherein the leadless device is powered by an implanted assembly that derives and stores power from patient-based energy sources.

17. The method of claim 13 wherein said analyzing comprises measuring seizure activity data from the first and second time periods, wherein seizure activity data comprises at least one of a number a clinical seizures during the first and second time period, a number of sub-clinical seizures during the first and second time period, seizure duration during the first and second time period, seizure patterns during the first and second time period, seizure frequency during the first and second time period, and time of seizure occurrence during the first and second time period.

18. The method of claim 17 further comprising generating a report that indicates the seizure activity data for the first and second time periods.

19. The method of claim 13 wherein the therapy is a pharmacological therapy.

20. The method of claim 19 wherein the neurological condition comprises epilepsy and the pharmacological therapy comprises an anti-epileptic drug (AED).

21. The method of claim 19 wherein changing at least one parameter of the therapy comprises changing at least one of a dosage, dosage frequency, form of the AED, and formulation of the AED.

22. The method of claim 13 wherein the therapy is electrical stimulation.

23. The method of claim 22 wherein the electrical stimulation is peripheral nerve stimulation or brain stimulation.

24. The method of claim 22 wherein changing at least one parameter of the therapy comprises changing at least one of frequency, pulse amplitude, pulse width, pulses per burst, burst frequency, burst/no-burst, and duty cycle.

25. The method of claim 13, wherein the step of commencing the therapy comprises providing a first pharmacological agent for treating epilepsy, and further wherein the step of changing at least one parameter of the therapy comprises providing a second pharmacological agent for treating epilepsy different from the first pharmacological agent.

26. The method of claim 13, wherein said implanting the device comprises injecting the device between at least one layer of the scalp and the skull.

27. The method of claim 13, wherein said implanting the device comprises delivering the device through a cannula to a target area.

28. A method for selecting a therapy for a patient suffering from a neurological or psychiatric condition, the method comprising:
- injecting a monitoring device beneath at least one layer of the patient's scalp;
- monitoring a physiological signal from the patient with the implanted device on an ambulatory basis for a first time period after commencement of the first therapy, wherein said monitoring for the first time period comprises sampling the physiological signal with the monitoring device;
- commencing a therapy;
- monitoring a physiological signal from the patient with the implanted device on an ambulatory basis for a second time period after commencement of the therapy, wherein said monitoring for the second time period comprises sampling the physiological signal with the monitoring device;
- processing the physiological signals from the first time period and second time period; and
- analyzing the processed physiological signals to evaluate efficacy of the therapy.

29. The method of claim 28, wherein:
- the neurological condition comprises epilepsy; and
- said analyzing comprises measuring seizure activity data from the first and second time periods, wherein seizure activity data comprises at least one of a number of clinical seizures during the first time period, a number of sub-clinical seizures during the first time period, seizure duration, seizure patterns, seizure frequency, and time of day of seizure occurrence.

30. The method of claim 28 wherein monitoring the physiological signal comprises:
- wirelessly transmitting a signal encoded with data indicative of the sampled physiological signal from the implanted device to a device that is external to the patient's body; and
- storing the sampled physiological signal in a memory that is external to the patient's body.

31. The method of claim 28 wherein said monitoring during the first time period is performed substantially continuously and said monitoring during the second time period is performed substantially continuously.

32. The method of claim 28 wherein the implanted device is leadless.

33. The method of claim 32 wherein the implanted device is powered by an externally generated radiofrequency signal.

* * * * *